US005834183A

United States Patent [19]

Orr et al.

[11] Patent Number: 5,834,183

[45] Date of Patent: *Nov. 10, 1998

[54] GENE SEQUENCE FOR SPINOCEREBELLAR ATAXIA TYPE 1 AND METHOD FOR DIAGNOSIS

[75] Inventors: Harry T. Orr, Minneapolis; Laura P. W. Ranum, St. Paul; Ming-yi Chung, Minneapolis, all of Minn.; Huda Y. Zoghbi, Houston, Tex.

[73] Assignee: Regents of the University of Minnesota, Minneapolis, Minn.

[ * ] Notice: The term of this patent shall not extend beyond the expiration date of Pat. No. 5,741,645.

[21] Appl. No.: 267,803

[22] Filed: Jun. 28, 1994

Related U.S. Application Data

[63] Continuation-in-part of Ser. No. 84,365, Jun. 29, 1993, abandoned.

[51] Int. Cl.[6] .............................. C12Q 1/68; C12P 19/34; C07H 21/04

[52] U.S. Cl. .......................... 435/6; 435/91.2; 435/172.3; 435/325; 435/252.3; 435/320.1; 536/23.5; 536/23.1; 536/24.31; 536/24.33; 935/4; 935/6; 935/8; 935/9; 935/78

[58] Field of Search .............................. 435/6, 91.2, 325, 435/172.3, 252.3, 320.1; 536/23.5, 23.1, 24.31, 24.33; 935/78, 4, 6, 8, 9

[56] References Cited

U.S. PATENT DOCUMENTS

| | | | |
|---|---|---|---|
| 4,683,194 | 7/1987 | Saiki et al. | 435/6 |
| 4,683,195 | 7/1987 | Mullis et al. | 435/6 |
| 4,800,159 | 1/1989 | Mullis et al. | 435/172.3 |
| 5,023,171 | 6/1991 | Ho et al. | 435/6 |
| 5,552,282 | 9/1996 | Caskey et al. | 435/6 |

FOREIGN PATENT DOCUMENTS

| | | |
|---|---|---|
| WO 91/19140 | 6/1991 | WIPO . |
| WO 92/12262 | 7/1992 | WIPO . |
| WO 92/14840 | 9/1992 | WIPO . |
| WO 92/20825 | 11/1992 | WIPO . |
| WO 94/24279 | 10/1994 | WIPO . |

OTHER PUBLICATIONS

Goldfarb et al. Annals of Neurology (1996) 39, No. 4, pp. 500–506.

Rameya et al, Neurology 1 Aug. 1995) 45, pp. 1587–1594.

The New England Bio Labs Catalog (1990–1991) p. 74.

A. Volz et al., "Regional Mapping of the Gene for Autosomal Dominant Spinocerebellar Ataxia (SCA1) by Localizing the Closely Linked D6S89 Locus to 6p24.2—p23.05", *Cytogenetics and Cell Genetics,* vol. 60, No. 1, 1992, pp. 37–39.

M. Chung, "Positional Cloning and Characterization of the Spinocerebellar Ataxia Type I Gene", *Dissertation Abstract International B,* vol. 54, No. 12, Jun. 1994, p. 6039–B.

H.T. Orr et al., "Expansion of an Unstable Trinucleotide CAG Repeat in Spinocerebellar Ataxia Type L", *Nature Genetics,* vol. 4, No. 3, Jul. 1993, pp. 221–226.

M. Chung et al., "Evidence for a Mechanism Predisposing to Intergenerational CAG Repeat Instability in Spinocerebellar Ataxia Type 1", *Nature Genetics,* vol. 5, No. 3, Nov. 1993, pp. 254–258.

S. Banfi et al., "Mapping and Cloning of the Critical Region for the Spinocerebellar Ataxia Type 1 Gene (SCA1) in a Yeast Artificial Chromosome Contig Spanning 1.2 Mb", *Genomics,* vol. 18, No. 3, Dec. 1993, pp. 627–635.

(List continued on next page.)

*Primary Examiner*—Carla J. Myers

*Attorney, Agent, or Firm*—Mueting, Raasch, Gebhardt & Schwappach, P.A.

[57] ABSTRACT

The present invention provides an isolated DNA molecule of the autosomal dominant spinocerebellar ataxia type 1 gene, which is located within the short arm of chromosome 6. This isolated DNA molecule is preferably located within a 3.36 kb EcoRI fragment, i.e., an EcoRI fragment containing about 3360 base pairs, of the SCA1 gene. The isolated sequences contain a CAG repeat region. The number of CAG trinucleotide repeats (n) is ≦36, preferably n=19–36, for normal individuals. For an affected individual n>36, preferably n≧43.

10 Claims, 22 Drawing Sheets

OTHER PUBLICATIONS

S. Banfi et al., "Identification and Characterization of the Gene Causing Type 1 Spinocerebellar Ataxia", *Nature Genetics,* vol. 7, No. 4, Aug. 1994, pp. 513–520.

L.P.W. Ranum et al., "Molecular and Clinical Correlations in Spinocerebellar Ataxia Type I: Evidence for Familial Effects on the Age of Onset", *Am. J. Hum. Genet.,* vol. 55, No. 2, Aug. 1994, pp. 244–252.

H.M. Albertsen et al., "Construction and characterization of a yeast artificial chromosome library containing seven haploid human genome equivalents," *Proc. Natl. Acad. Sci. USA, 87,* 4256–4260 (1990).

S. Banfi et al., "An easy and rapid method for the detection of chimeric yeast artificial chromosome clones," *Nucleic Acids Res.,* 20, 1814 (1992).

G.P. Bates et al., "Characterization of a yeast artificial chromosome contig spanning the Huntington's disease gene candidate region," *Nature Genetics,* 1,180–187 (1992).

H.J. Bellen et al., "The Drosophila Couch potato protein is expressed in nuclei of peripheral neuronal precursors and shows homology to RNA–binding proteins," *Genes & Development,* 6, 2125–2136 (1992).

M. Benson et al., "The Drosophila zeste protein binds cooperatively to sites in many gene regulatory regions: implications for tranvection and gene regulation," *EMBO J,* 7, 3907–3815 (1988).

C. Breukel et al., "Vector–Alu PCR: a rapid step in mapping cosmids and YACs," *Nucleic Acids Res.,* 18, 3097 (1990).

S.K. Bronson et al., "Isolation and characterization of yeast artificial chromosome clones linking the HLA–B and HLA–C loci," *Proc. Natl. Acad. Sci. USA,* 88, 1676–1680 (1991).

D. Brook et al., "Molecular Basis of Myotonic Dystrophy: Expansion of a Trinucleotide (CTG) Repeat at the 3' End of a Transcript Encoding a Protein Kinase Family Member," *Cell,* 68, 799–808 (1992).

B.H. Brownstein et al., "Isolation of single–copy human genes from a library of yeast artificial chromosome clones, " *Science,* 244, 1348–1351 (1989).

H.G. Brunner et al., "Brief Report: Reverse mutation in Myotonic Dystrophy," *New Engl. J. Med.,* 328, 476–480 (1993).

J. Buxton et al., "Detection of an unstable fragment of DNA specific to individuals with myotonic dystrophy," *Nature,* 355, 547–548 (1992).

P.M. Conneally et al., "Report of the committee on methods of linkage analysis and reporting," *Cytogenet. Cell. Gent., 40,* 356–359 (1985).

A. J. Courey et al., "Synergistic Activation by the Glutamine–Rich Domains of Human Transcription Factor Sp1," *Cell,* 59, 827–836 (1989).

P. Coutinho et al., "Autosomal dominant system degeneration in Portuguese families of the Azores Islands," *Neurology,* 28, 703–709 (1978).

R.D. Currier et al., "Spinocerebellar ataxia: study of a large kindred," *Neurology,* 22, 1040–1043 (1972).

C.A. Feener et al., "Rapid detection of CA polymorphisms in cloned DNA: Application to the 5' region of the dystrophin gene," *Am. J. Hum. Genet.,* 48, 621–627 (1991).

A.P. Feinberg et al., "A technique for radiolabeling DNA restriction endonuclease fragments to high specific activity," *Anal. Biochem., 137,* 266–267 (1984).

Y.–H. Fu et al., "Variation of the CGG Repeat at the Fragile X Site Results in Gentic Instability: Resolution of the Sherman Paradox," *Cell,* 67, 1047–1058 (1991).

Y.–H. Fu et al., "An Unstable Triplet Repeat in a Gene Related to Myotonic Muscular Dystrophy," *Science,* 255, 1256–1258 (1992).

E.D. Green et al., "Systematic screening of yeast artificial–chromosome libraries by use of the polymerase chain reaction," *Proc. Natl. Acad. Sci. USA,* 87, 1213–1217 (1990).

J.L. Haines et al., "Spinocerebellar ataxia in large kindred: age at onset, reproduction, and genetic linkage studies," *Neurology,* 34, 1542–1548 (1984).

H.G. Harley et al., "Expanasion of an unstable DNA region and phenotypic variation in myotonic dystrophy," *Nature, 355,* 545–546 (1992).

H.G. Harley et al., "Unstable DNA sequence in myotonic dystrophy," *Lancet,* 339, 1125–1128 (1992).

D.M. Heery et al., "A simple method for subcloning DNA fragments from gel slices," *Trends Genet.,* 6, 173 (1990).

Huntington's Disease Collaborative Research Group, "A Novel Gene Containing a Trinucleotide Repeat That is Expanded and Unstable on Huntington's Disease Chromosomes," *Cell,* 72, 971–983 (1993).

J.F. Jackson et al., "Spinocerebellar ataxia and HLA linkage: risk prediction by HLA typing," *N. Engl. J. Med.,* 296, 1138–1141 (1977).

G. Joslyn et al., "Identification of delection mutations and three new genes at the familial polposis locus," *Cell,* 66, 601–613 (1991).

B.J.B. Keats et al., "Localization of the gene for spinocerebellar ataxia to the short arm of chromosome 6 in a kindred for which close linkage to HLA is excluded," *Am. J. Hum. Genet.,* 49, 972–977 (1991).

E.J. Kremer et al., "Mapping of DNA Instability at the Fragile X to a Trinucleotide Repeat Sequence p(CCG)n," *Science,* 252, 1711–1714 (1991).

T.J. Kwiatkowski et al., "Rapid identification of yeast artificial chromosome clones by matrix pooling and crude lysate PCR," *Nucleic Acids Res.,* 18, 7191–7192 (1990).

T.J. Kwiatkowski et al., "The gene for autosomal dominant spinocerebellar atacia (SCA1) maps centromeric to D6S89 and shows no recombinant, in nine large kindreds, with a dinucleotide repeat at the AM10 locus," *Am. J. Hum. Genet.,* 53, 371–400 (1993).

A.R. LaSpada et al., "Androgen receptor gene mutations in X–linked spinal and bulbar muscular atrophy," *Nature,* 352, 77–79 (1991).

G.M. Lathrop et al., "Strategies for multilocus linkage analysis in humans," *Proc. Natl. Acad. Sci. USA,* 81, 3443–3446 (1984).

F. LeBorgne–Demarquoy et al., "Two dinucleotide repeat polymorphisms at the D6S202 locus," *Nucleic Acids Res.,* 19, 6060 (1991).

M. Litt et al., "A TG microsatellite VNTR detected by PCR is located on 6p (HGM10 No. D6S89)," *Nucleic Acids Res.,* 18, 4301 (1990).

M. Mahadevan et al., Myotonic Dystrophy Mutation: An Unstable CTG Repeat in the 3' Untranslated Region of the Gene, *Science,* 255, 1253–1255.

D. Marchuk et al., "Construction of T–vectors, a rapid and general system for direct cloning of unmodified PCR products," *Nucleic Acids Res.,* 19, 1154 (1990).

D.L. Nelson et al., "Alu–primed polymerase chain reaction for regional assignment of 110 yeast artificial chromosome clones from the human X chromosome: Identification of clones associated with a disease locus," *Natl. Acad. Sci. USA,* 88, 6157–6161 (1991).

D.L. Nelson et al., "Alu polymerase chain reaction: A method for rapid isolation of human specific sequences from complex DNA sources," *Proc. Natl. Sci. USA,* 86, 6686–6690 (1989).

NIH/CEPH Collaborative Mapping Group, "A comprehensive genetic linkage map of the human genome," *Science,* 258, 67–68 (1992).

H.E. Nino et al., "A family with hereditary ataxia: HLA typing," *Neurology,* 30, 12–20 (1980).

G. Orozco et al., "Dominantly inherited olivopontocerebellar atrophy from eastern Cuba," *J. Neurolog. Sciences,* 93, 37–50 (1989).

H.T. Orr, "Molecular genetics of the SCA1 locus on chromosomes 6P," Abstract of National Institute of Health Grant No. 5R01NS22920–05.

C.A. Quigley et al., "Complete Deletion of the Androgen Receptor Gene: Definition of the Null Phenotype of the Androgen Insensitivity Syndrome and Determination of Carrier Status," *J. Clin. Endo. Metab.,* 74, 927–933 (1992).

L.P.W. Ranum et al., "Localization of the autosomal dominant, HLA–linked spinocerebellar ataxia (SCA1) locus in two kindreds within an 8cM subregion of chromosome 6p," *Am. J. Hum. Genet.,* 49, 31–41 (1991).

L.P.W. Ranum et al., "Dinucleotide repeat polymorphism at the D6S109 locus," *Nucleic Acids Res.,* 19, 1171 (1991).

R.K. Saiki et al., "Enzymatic Amplification of β–Globin Genomic Sequences and Restriction Site Analysis for Diagnosis of Sickle Cell Anemia," *Science,* 230, 1350–1354 (1985).

J. Sambrook et al., *Molecular Cloning, A Laboratory Manual,* 2nd ed. ; Cold Spring Harbor, NY (1989) (title page, copyright page, and contents (pp. v–xxxii)).

S.J. Scharf et al., "Direct Cloning and Sequence Analysis of Enzymatically Amplified Genomic Sequences," *Sciences,* 233, 1076–1078 (1986).

J.W. Schut et al., "Hereditary ataxia: clinical study through six generations," *Arch Neurol. Psychiatry,* 63, 535–567 (1950).

D.C. Schwartz et al., "Separation of yeast chromosome–size DNAs by pulsed field gradient gel electrophoresis," *Cell, 37,* 67–75 (1984).

P.G. Sealy et al., "Removal of repeated sequences from hybridization probes," *Nucleic Acids Res.,* 13, 1905–1922 (1985).

G.A. Silverman et al., "Use of yeast artificial chromosome clones for mapping and walking within human chromosome segment 18q21.3," *Proc. Natl. Acad. Sci. USA,* 86, 7485–7489 (1989).

M. Spadaro et al., "HLA–linked spinocerebellar ataxia: a clinical and genetic study of large Italian kindreds," *Acta Neuerol. Scand.,* 85, 257–265 (1992).

M. Trifiro et al., "The 56/58 kDa androgen–binding protein in male genital skin fibroblasts with a deleted androgen receptor gene," *Molecular and Cellular Endocrinology,* 75, 37–47 (1991).

H. Vaessin et al., "Prospero is Expressed in Neuronal Precursors and Encodes a Nuclear Protein that is involved in the Control of Axonal Outgrowth in Drosophila," *Cell,* 67, 941–953 (1991).

G.J.B. Van Ommen et al., "Restriction analysis of chromosomal DNA in a size range up to two million base pairs by pulsed field graident electrophoresis" in *Human Genetic Diseases, A Practical Approach;* K.E. Davies, ed.; IRL Press, Oxford; pp. 113–133 (1986).

A.J.M.H. Verkerk et al., "Identification of a Gene (FMR–1) Containing a CGG Repeat Coincident with a Breakpoint Cluster Region Exhibiting Length Variation in Fragile X Syndrome," *Cell, 65,* 905–914 (1991).

M.C. Wapenaar et al., "The genes for X–linked ocular albinism (OA1) and microphthalmia with linear skin defects (MLS): cloning and characterization of the critical regions," *Hum. Mol. Genet.,* 2, 947–952 (1993).

J. Weissenbach et al., "A second–generation linkage map of the human genome," *Nature,* 359, 794–801 (1992).

K.A. Wharton et al., "Nucleotide Sequence from the Neurogenic Locus Notch Implies a Gene Product that Shares Homology with Proteins Containing EGF–like Repeats," *Cell,* 43, 567–581 (1985).

H. Yakura et al., "Hereditary ataxia and HLA genotypes," *N. Engl. J. Med.,* 291, 154–155 (1974).

H.Y. Zoghbi, "Molecular Studies of HLA–Linked Spinocerebellar Ataxia," Abstract of National Institute of Health Grant No. 5R01NS27699–05.

H.Y. Zoghbi, "The Spinocerebellar degenerations," in *Current Neurology;* S.H. Appel, ed.; vol. 11, pp. 121–144; Mosby–Year Book, St. Louis (1991).

H.Y. Zoghbi et al., "Deletion and linkage mapping of eight markers from the proximal short arm of chromosome 6," *Genomics,* 6, 352–357 (1990).

H.Y. Zoghbi et al., "Generation of YAC Contigs by Walking," in *YAC Libraries;* D.L. Nelson et al., eds.; W.H. Freeman & Co.: New York, NY; pp. 93–112 (1993).

H.Y. Zoghbi et al., "The gene for autosomal dominant spinocerebellar ataxia (SCA1) maps telomeric to HLA complex and is closely linked to the D6S89 locus in three large kindreds," *Am. J. Hum. Genet.,* 49, 23–30 (1991).

H.Y. Zoghbi et al., "Sixty–five radiationi hybrids for the short arm of human chromosome 6p: Their value as mapping panel and as a source for rapid isolation of new problems using repeat element–mediated PCR," *Genomics,* 9, 713–720 (1991).

H.Y. Zoghbi et al., "Spinocerebellar ataxia: Variable age of onset and linkage to human leukocyte antigen in a large kindred," *Ann. Neurol.,* 23, 580–584 (1988).

H.Y. Zoghbi et al., "Assignment of autosomal dominant spinocerebellar ataxia (SCA1) centromeric to the HLA region of the short arm of chromosome 6, using multilocus linkage analysis," *Am. J. Hum. Genet., 44,* 255–263 (1989).

M.D. Adams et al., "3,400 new expressed sequence tags to identify diversity of transcripts in human brain," *Nature Genetics, 4,* 256–267 (1993).

S. F. Altschul, "Basic Local Alignment Search Tool," *J. Mol. Biol.,* 215, 403–410 (1990).

A.T. Bankier et al., "Random Cloning and Sequencing by the M13/Dideoxynucleotide Chain Termination Method," *Meth. in Enzymol.,* 155, 51–93 (1987).

P. Chomczynski et al., "Single–Step Method of RNA Isolation by Acid Guanidinium Thiocyanate–Phenol–Chloroform Extraction," *Anal. Biochem.,* 162, 156–159 (1987).

Cole et al., "The EBV–Hybridoma Technique and its Application to Human Lung Cancer," *Monoclonal Antibodies and Cancer Therapy;* A.R. Liss Ed.; pp. 77–96 (1985).

Depicker et al., "Nopaline Synthase: Transcript Mapping and DNA Sequence," *J. Mol. Appl. Gen.,* 1, 561–573 (1982).

Fiers et al., “Complete nucleotide sequence of SV40 DNA,” *Nature,* 273, 113–120 (1978).
M. A. Frohman, *PCR Protocols. A Guide to Methods and Applications;* M.A. Innis et al., Eds.; Academic Press: San Diego (1990). Enclosed are the cover page, Copyright page, and Table of Contents (pp. v–x).
Gershoni et al., “Protein Blotting: Principles and Applications,” *Anal. Biochem.,* 131, 1–15 (1983).
R.A. Gibbs et al., “Identification of mutations leading to the Lesch–Nyhan syndrome by automated direct DNA sequencing of in vitro amplified cDNA,” *Proc. Natl. Acad. Sci. USA,* 86, 1919–1923 (1989).
Graham et al., “Characteristics of a Human Cell Line Transformed by DNA from Human Adenovirus Type 5,” *J. Gen. Virol.,* 36, 59–72 (1977).
Graham et al., “A New Technique for the Assay of Infectivity of Human Adenovirus 5 DNA, ” *Virology,* 52, 456–457 (1978).
Groden et al., “Identification and Characterization of the Familial Adenomatous Polyposis *Coli* Gene,” *Cell, 66,* 589–600 (1991).
Hsiao et al., “High–frequency transformation of yeast by plasmids containing the cloned yeast ARG4 gene,” *Proc. Natl. Acad. Sci. USA,* 78, 3829–3833 (1979).
T. C. Johnston et al., “Nucleotide Sequence of the LuxB Gene of *Vibrio harveyi* and the Complete Amino Acid Sequence of the β Subunit of Bacterial Luciferase,” *J. Biol. Chem.,* 261, 4805–4811 (1986).
Jones, “Proteinase Mutants of Saccharomyces Cerevisiae,” *Genetics,* 85, 12 (1977).
Kingsman et al., “Replication in *Saccharomyces cerevisiae* of Plasmid pBR313 Carrying DNA from the Yeast trpl Region,” *Gene,* 7, 141–152 (1979).
Kohler et al., “Derivation of specific antibody–producing tissue cultures and tumor lines by cell fusion,” *Eur. J. Immunol., 6,* 511–519 (1976).
M. Kozak, “The Scanning Model for Translation: An Update,” *J. Cell Biol.,* 108, 229–241 (1989).
Luckow et al., “Trends in the Development of Baculovirus Expression Vectors,” *Bio/Technology,* 6, 47–55 (1988).
Maeda et al., Production of human α–interferon in silkworm using a baculovirus vector, *Nature,* 315, 592–594 (1985).
Maniatis et al., *Molecular Cloning: A Laboratory Manual;* Cold Spring Harbor, NY (1982). Enclosed are the Title Page, Copyright page and Table of Contents (pp. v–x).
Mather, “Establishment and Characterization of Two Distinct Mouse Testicular Epithelial Cell Lines,” *Biol. Reprod.,* 23, 243–251 (1980).
Mather et al., “Culture of Testicular Cells in Hormone––Supplemented Serum–Free Medium,” *Annals. NY Acad. Sci.,* 383, 44–68 (1982).
Maxum et al., “Sequencing End–Laneled DNA with Base–Specific Chemical Cleavages,” *Methods in Enzymology,* 65, 499–591 (1980).
V. Mehra et al., “Efficient mapping of protein antigenic determinants,” *Procl. Natl. Acad. Sci. USA,* 83, 7013–7107 (1986).
Messing et al., “A system for shotgun DNA sequencing,” *Nucl. Acids Res.,* 9, 309 (1981).
Miller et al., “An Insect Baculovirus Host–Vector System for High–Level Expression of Foreign Genes,” *Genetic Engineering,* 8, 277–279 (1986).
Mulligan et al., “Expression of a Bacterial Gene in Mammalian Cells,” *Science,* 209, 1422–1427 (1980).
Pavlakis et al., “Expression of two human growth hormone genes in monkey cells infected by simian virus 40 recombinants,” *Proc. Natl. Acad. Sci. USA,* 78, 7398–7402 (1981).
Stinchcomb et al., “Isolation and characterization of a yeast chromosomal replicator,” *Nature,* 282, 39–321 (1979).
Tschumper et al., “Sequence of a yeast DNA fragment containing a chromosomal replicator and TRP1 gene,” *Gene,* 10, 157–166 (1980).
Urlaub et al., “Isolation of Chinese hamster cell mutants deficient in dihydrofolate reductase activity,” *Proc. Natl. Acad. Sci. USA,* 77, 4216–4220.
Van Solinger et al., “Fustion of yeast Spheroplasts,” *J. Bact.,* 130, 946–947 (1977).
C. Yanisch–Perron et al., “Improved M13 phage vectors and host strains: nucleotide sequences of the M13mp18 and pUC19 vectors,” *Gene,* 33, 103–119 (1985).
H.Y. Zoghbi et al., “Extensive DNA Polymorphism at the Factor XIIIa (F13A) Locus and Linkage to HLA, ” *Am. J. Hum. Genet.,* 42, 877–883 (1988).
Renauld et al., “Expression in Activated $CD4^+$ T cells, Genomic Organization, and Comparison with the Mouse Gene,” *The Journal of Immunology,* 144, (11), 4235–4241 (1990) and Supplement (pp. 1–6).
Sommer et al., “Minimal homology requirements for PCR Primers,” *Nucleic Acids Research,* 17, (16), 6749 (1989).

FIG. 1

```
   1 TTTTGAAACT TGCAGAGAAC AGGATTATTT CTGGCGGCCT CTGCTGAGTT GGCGTGTGTG
  61 TGTGTGTTTG TGTGTGTGTG TATTAGGGAG AGGAAATCGT AGGTCCAGTG TGGACCCAGA
 121 GCTAAGGGGA ATCTTGGAGA GTAGTGGCTC TGGCAGATGA GGATTCAGAA ATCGAGTGCA
 181 AGGACTGTTC TGGACTTTCA CTGCTAACCT GCTTTTTCTC AGTGCCTGGC TCTGAGGGCA
 241 GGGTCCAGCT GGTGTCATGC TCTCCAAGGG CTTCATTTTA TGTTCCAGCC AGGCAAAGGA
 301 GAGGTGAGAA ATGGAACCAA CATTTCTGAA AAGGAAATTT AAGAACTGCA TCATCTGCCC
 361 TTGAAGAAGA AAAGGAGAAA AAAAAACAGG AGAGAGGGTA TTGAGAACAT CTTAGGGGAG
 421 TTGTTAACTC CATTAAAAAA TATATGTGTT ACAGTGTTCA CTTGCCCAGT GTCTTCATAA
 481 TCTTCCTTTA TAATGTGCAG CTGCCACGGC TAGTGTTTTT GTTTTTGTTG TTGTTGTTTT
 541 GTTTCGTTTT TGGAGACAGA GTGTCGCTCT GTTGCCCAGG CTGGAGTACA ATGGTGCAAT
 601 CTCGGCTCAC TGCAACCTCT GCCTCCTGGG TTCAAGCAAT TCTCCTGCCT CAGCCTCTCA
 661 AGTAGCTGGG ACTACAGCCG TGTGCCAGCT AATGTTACAC CAGGCTAAAT TTGTTTTTTA
 721 TTTTTTATTT TTGGTAGAGA CGGGGTTTCA CCATGTTAGC CAGGATGGTC TTAATCTCCT
 781 GACCTCGTGA TCTGCCTGCC TCGGCCTCCC AAAGTGTTGG CTAGTGTTTT CTCTGCTTCA
 841 GTGCTTGGGG TATGATTGGG TTATGGGAGT TCACACCGAG TCCAGGGCCT AGTCTTAATC
 901 TTGCCAAAGA TGTTCTTTCC CCGGTGCTCA TGTTCTGATG TCCTTTCCCT CCTTCCCTTT
 961 CTCCTCCCTT TCCTTTTCCC TTTGTCACTG CCCTCTTCCC TTTCCCAGCA TCCAGAGCTG
1021 CTGTTGGCGG ATTGTACCCA CGGGGAGATG ATTCCTCATG AAGAGCCTGG ATCCCCTACA
1081 GAAATCAAAT GTGACTTTCC GTTTATCAGA CTAAAATCAG AGCCATCCAG AACAGTGAAA
1141 CAGTCACCGT GGAGGGGGGA CGGCGAAAAA TGAAATCCAA CCAAGAGCGG AGCAACGAAT
1201 GCCTGCCTCC CAAGAAGCGC GAGATCCCCG CCACCAGCCG GTCCTCGGAG GAGAAGGCCC
1261 CTACCCTGAC CCAGCGACAA CCACCGGGTG GAGGGCACAG CATTGGCTCC CGGGCAACCC
1321 TGGTGGCCGG GGCCACGGGG GCGGGAGGCA TGGGCCGGCA GGGACCTCGG TGGAGCTTGG
1381 TTTACAACAG GGAATAGGTT TACACAAAGC ATTGTCCACA GGGCTGGACT ACTCCCCGCC
1441 CAGCGCTCCC AGGTCTGTCC CCGTGGCCAC CACGCTGCCT GCCGCGTACG CCACCCCGCA
1501 GCCAGGGACC CCGGTGTCCC CCGTGCAGTA CGCTCACCTG CCGCACACCT TCCAGTTCAT
1561 TGGGTCCTCC CAATACAGTG GAACCTATGC CAGCTTCATC CCATCACAGC TGATCCCCCC
1621 AACCGCCAAC CCCGTCACCA GTGCAGTGGC CTCGGCGCAG GGGCCACCAC TCCATCCCAG
1681 CGCTCCCAGC TGGAGGCCTA TTCCACTCTG CTGGCCAACA TGGGCAGTCT GAGCCAGACG
1741 CCGGGACACA AGGCTGAGCA GCAGCAGCAG CAGCAGCAGC AGCAGCAGCA GCAGCATCAG
1801 CATCAGCAGC AGCAGCAGCA GCAGCAGCAG CAGCAGCAGC AGCAGCAGCA CCTCAGCAGG
1861 GCTCCGGGGC TCATCACCCC GGGTCCCCCC CAACCAGCCC AGCAGAACCA GTACGTCCAC
1921 ATTTCCAGTT CTCCGCAGAA CACCGGCCGC ACCGCCTCTC CTCCGGCCAT CCCCGTCCAC
1981 CTCCACCCCC ACCAGACGAT GATCCCACAC ACGCTCACCC TGGGGCCCCC CTCCCAGGTC
2041 GTCATGCAAT ACGCCGACTC CGGCAGCCAC TTTGTCCCTC GGGAGGCCAC CAAGAAAGCC
2101 GAGAGCAGCC GGCTGCAGCA GGCCATCCAG GCCAAGGAGG TCCTGAACGG TGAGATGGAG
2161 AAGAGCCGGC GGTACGGGGC CCCGTCCTCA GCCGACCTGG GCCTGGGCAA GGCAGGCGGC
2221 AAGTCGGTTC CTCACCCGTA CGAGTCCAGG CACGTGGTGG TCCACCCGAG CCCCTCAGAC
2281 TACAGCAGTC GTGATCCTTC GGGGGTCCGG GCCTCTGTGA TGGTCCTGCC CAACAGCAAC
2341 ACGCCCGCAG CTGACCTGGA GGTGCAACAG GCCACTCATC GTGAAGCCTC CCCTTCTACC
2401 CTCAACGACA AAAGTGGCCT GCATTTAGGG AAGCCTGGCC ACCGGTCCTA CGCGCTCTCA
2461 CCCCACACGG TCATTCAGAC CACACACAGT GCTTCAGAGC CACTCCCGGT GGACTGCCAG
2521 CCACGGCCTT CTACGCAGGG ACTCAACCCC CTGTCATCGG CTACCTGAGC GGCCAGCAGC
2581 AAGCAATCAC CTACGCCGGC AGCCTGCCCC AGCACCTGGT GATCCCCGGC ACACAGCCCC
2641 TGCTCATCCC GGTCGGCAGC ACTGACATGG AAGCGTCGGG GGCAGCCCCG GCCATAGTCA
2701 CGTCATCCCC CCAGTTTGCT GCAGTGCCTC ACACGTTCGT CACCACCGCC CTTCCCAAGA
2761 GCGAGAACTT CAACCCTGAG GCCCTGGTCA CCCAGGCCGC CTACCCAGCC ATGGTGCAGG
2821 CCCAGATCCA CCTGCCTGTG GTGCAGTCCG TGGCCTCCCC GGCGGCGGCT CCCCCTACGC
2881 TGCCTCCCTA CTTCATGAAA GGCTCCATCA TCCAGTTGGC CAACGGGGAG CTAAAGAAGG
2941 TGGAAGACTT AAAACAGAAG ATTTCATCCA GAGTGCAGAG ATAAGCAACG ACCTGAAGAT
3001 CGACTCCAGC ACCGTAGAGA GGATTGAAGA CAGCCATAGC CCGGGCGTGG CCGTGATACA
3061 GTTCGCCGTC GGGGAGCACC GAGCCCAGGT AACGTTAGCC AGGGTGGCAC AGGGATGGGA
3121 CACCATACCG TGATGCCATC ATCATCTCCT GGCAAGACGA ATTGCTTCTA TGAGGCAGGA
3181 TTAAGGGTTC TCGGGTACAC CTAGACCTTA GACTCGGCCT TTCCCAACTG CGTTCTCTAG

3241 AAAAAATAAG CCCCATTTCC CCGTGATCTC TGCTGTGTGT AATGAATTAA CCTCCATGCA
3301 TGGAGAGTGG GGCTAGTTAT GGAGTCCTTG AGACAATCCA GAAACTCACC ACTCTCGTTA
3361 TTTTTT
```

FIG. 2

Patient #1 (CAG)nCACCTCAGCAGGGCTCCGGGGCTCATC; n=56.

CAGCAGCAGCAGCAGCAGCAGCAGCAGCAGCAGCAGCAGCAGCAGCAGCAGCAGCAGCAGCAGCAG
CAGCAGCAGCAGCAGCAGCAGCAGCAGCAGCAGCAGCAGCAGCAGCAGCAGCAGCAGCAGCAGCAG
CAGCAGCAGCAGCAGCAGCAGCAGCAGCAGCAGCAGCACCTCAGCAGGGCTCCGGGGCTCATC

Patient #2 (CAG)nCACCTCAGCAGGGCTCCGGGGCTCATC; n=69.

CAGCAGCAGCAGCAGCAGCAGCAGCAGCAGCAGCAGCAGCAGCAGCAGCAGCAGCAGCAGCAGCAG
CAGCAGCAGCAGCAGCAGCAGCAGCAGCAGCAGCAGCAGCAGCAGCAGCAGCAGCAGCAGCAGCAG
CAGCAGCAGCAGCAGCAGCAGCAGCAGCAGCAGCAGCAGCAGCAGCAGCAGCAGCAGCAGCAGCAG
CAGCAGCAGCACCTCAGCAGGGCTCCGGGGCTCATC

Patient #3 (CAG)nCACCTCAGCAGGGCTCCGGGGCTCATC; n=47.

CAGCAGCAGCAGCAGCAGCAGCAGCAGCAGCAGCAGCAGCAGCAGCAGCAGCAGCAGCAGCAGCAG
CAGCAGCAGCAGCAGCAGCAGCAGCAGCAGCAGCAGCAGCAGCAGCAGCAGCAGCAGCAGCAGCAG
CAGCAGCAGCACCTCAGCAGGGCTCCGGGGCTCATC

Patient #4 (CAG)nCACCTCAGCAGGGCTCCGGGGCTCATC; n=48.

CAGCAGCAGCAGCAGCAGCAGCAGCAGCAGCAGCAGCAGCAGCAGCAGCAGCAGCAGCAGCAGCAG
CAGCAGCAGCAGCAGCAGCAGCAGCAGCAGCAGCAGCAGCAGCAGCAGCAGCAGCAGCAGCAGCAG
CAGCAGCAGCAGCACCTCAGCAGGGCTCCGGGGCTCATC

Patient #5 TGAG(CAG)n; n=50.

TCAGCAGCAGCAGCAGCAGCAGCAGCAGCAGCAGCAGCAGCAGCAGCAGCAGCAGCAGCAGCAGCA
GCAGCAGCAGCAGCAGCAGCAGCAGCAGCAGCAGCAGCAGCAGCAGCAGCAGCAGCAGCAGCAGCA
GCAGCAGCAGCAGCAGCAGCAG

FIG. 3

1 GATCCCCCCA ACCGCCAACC CCGTCACCAG TGCAGTGGCC TCGGCGCAGG

GCT-435

51 GGCCACCACT CCATCCCAGC GCTCCCAGCT GGAGGCCTAT TCCACTCTGC

CAG-b

Rep-2

101 TGGCCAACAT GGGCAGTCTG AGCCAGACGC CGGGACACAA GGCTGAGCAG

151 CAGCAGCAGC AGCAGCAGCA GCAGCAGCAG CAGCATCAGC ATCAGCAGCA

CAG-a

201 GCAGCAGCAG CAGCAGCAGC AGCAGCAGCA GCAGCAGCAC CTCAGCAGGG

GCT-214

251 CTCCGGGGCT CATCACCCCG GGTCCCCCCC ACCAGCCCAG CAGAACCAGT

Rep-1 Pre-2

301 ACGTCCACAT TTCCAGTTCT CCGCAGAACA CCGGCCGCAG CGCCTCTCCT

351 CCGGCCATCC CCGTCCACCT CCACCCCCAC CAGACGATGA TCCCACACAC

401 GCTCACCCTG GGGCCCCCCT CCCAGGTCGT CATGCAATAC GCCGACTCCG

Pre-1

451 GCAGCCACTT TGTCCCTCGG GAGGCCACCA AGAAAGCCGA GAGCAGCCGG

501 CTGCAG

FIG. 15

| Fig. 15a |
| --- |
| Fig. 15b |
| Fig. 15c |
| Fig. 15d |

FIG. 15a

```
   1  CTACTACAGTGGCGGACGTACAGGACCTGTTTCACTGCAGGGGGATCCAAAACAAGCCCCGTGGAGCAACAGCCAGAGCAACAGCAGCTG    90
  91  CAAGACATTGTTTCTCTCCCTCTGCCCCCCCTTCCCCACGCAACCCCAGATCCATTTACACTTTACAGTTTTACCTCACAAAAACTACTA   180
 181  CAAGCACCAAGCTCCCTGATGGAAAGGAGCATCGTGCATCAAGTCACCAGGGTGGTCCATTCAAGCTGCAGATTTGTTTGTCATCCTTGT   270
 271  ACAGCAATCTCCTCCTCCACTGCCACTACAGGGAAGTGCATCACATGTCAGCATACTGGAGCATAGTGAAAGAGTCTATTTTGAAGCTTC   360
 361  AAACTTAGTGCTGCTGCAGACCAGGAACAAGAGAGAAAGAGTGGATTTCAGCCTGCACGGATGGTCTTGAAACACAAATGGTTTTTGGTC   450
 451  TAGGCGTTTTACACTGAGATTCTCCACTGCCACCCTTTCTACTCAAGCAAAATCTTCGTGAAAAGATCTGCTGCAAGGAACTGATAGCTT   540
 541  ATGGTTCTCCATTGTGATGAAAGCACATGGTACAGTTTTCCAAAGAAATTAGACCATTTTCTTCGTGAGAAAGAAATCGACGTGCTGTTT   630
 631  TCATAGGGTATTTCTCACTTCTCTGTGAAAGGAAGAAAGAACACGCCTGAGCCCAAGAGCCCTCAGGAGCCCTCCAGAGCCTGTGGGAAG   720
 721  TCTCCATGGTGAAGTATAGGCTGAGGCTACCTGTGAACAGTACGCAGTGAATGTTCATCCAGAGCTGCTGTTGGCGGATTGTACCCACGG   810
 811  GGAGATGATTCCTCATGAAGAGCCTGGATCCCCTACAGAAATCAAATGTGACTTTCCGTTTATCAGACTAAAATCAGAGCCATCCAGACA   900
 901  GTGAAACAGTCACCGTGGAGGGGGGACGGCGAAAAATGAAATCCAACCAAGAGCGGAGCAACGAATGCCTGCCTCCCAAGAAGCGCGAGA   990
   1                                         M  K  S  N  Q  E  R  S  N  E  C  L  P  P  K  K  R  E  I    19
 991  TCCCCGCCACCAGCCGGTCCTCCGAGGAGAAGGCCCCTACCCTGCCCAGCGACAACCACCGGGTGGAGGGCACAGCATGGCTCCCGGGCA  1080
  20   P  A  T  S  R  S  S  E  E  K  A  P  T  L  P  S  D  N  H  R  V  E  G  T  A  W  L  P  G  N    49
1081  ACCCTGGTGGCCGGGGCCACGGGGGCGGGAGGCATGGGCCGGCAGGGACCTCGGTGGAGCTTGGTTTACAACAGGGAATAGGTTTACACA  1170
  50   P  G  G  R  G  H  G  G  G  R  H  G  P  A  G  T  S  V  E  L  G  L  Q  Q  G  I  G  L  H  K    79
1171  AAGCATTGTCCACAGGGCTGGACTACTCCCCGCCCAGCGCTCCCAGGTCTGTCCCCGTGGCCACCACGCTGCCTGCCGCGTACGCCACCC  1260
  80   A  L  S  T  G  L  D  Y  S  P  P  S  A  P  R  S  V  P  V  A  T  T  L  P  A  A  Y  A  T  P   109
1261  CGCAGCCAGGGACCCCGGTGTCCCCCGTGCAGTACGCTCACCTGCCGCACACCTTCCAGTTCATTGGGTCCTCCCAATACAGTGGAACCT  1350
 110   Q  P  G  T  P  V  S  P  V  Q  Y  A  H  L  P  H  T  F  Q  F  I  G  S  S  Q  Y  S  G  T  Y   139
1351  ATGCCAGCTTCATCCCATCACAGCTGATCCCCCCAACCGCCAACCCCGTCACCAGTGCAGTGGCCTCGGCCGCAGGGGCCACCACTCCAT  1440
 140   A  S  F  I  P  S  Q  L  I  P  P  T  A  N  P  V  T  S  A  V  A  S  A  A  G  A  T  T  P  S   169
1441  CCCAGCGCTCCCAGCTGGAGGCCTATTCCACTCTGCTGGCCAACATGGGCAGTCTGAGCCAGACGCCGGGACACAAGGCTGAGCAGCAGC  1530
 170   Q  R  S  Q  L  E  A  Y  S  T  L  L  A  N  M  G  S  L  S  Q  T  P  G  H  K  A  E  Q  Q  Q   199
1531  AGCAGCAGCAGCAGCAGCAGCAGCAGCAGCATCAGCATCAGCAGCAGCAGCAGCAGCAGCAGCAGCAGCAGCAGCAGCAGCAGCACCTCA  1620
 200   Q  Q  Q  Q  Q  Q  Q  Q  H  Q  H  Q  Q  Q  Q  Q  Q  Q  Q  Q  Q  Q  Q  Q  Q  Q  Q  H  L  S   229
1621  GCAGGGCTCCGGGGCTCATCACCCCGGGGTCCCCCCCACCAGCCCAGCAGAACCAGTACGTCCACATTTCCAGTTCTCCGCAGAACACCG  1710
 230   R  A  P  G  L  I  T  P  G  S  P  P  P  A  Q  Q  N  Q  Y  V  H  I  S  S  S  P  Q  N  T  G   259
1711  GCCGCACCGCCTCTCCTCCGGCCATCCCCGTCCACCTCCACCCCCACCAGACGATGATCCCACACACGCTCACCCTGGGGCCCCCCTCCC  1800
 260   R  T  A  S  P  P  A  I  P  V  H  L  H  P  H  Q  T  M  I  P  H  T  L  T  L  G  P  P  S  Q   289
1801  AGGTCGTCATGCAATACGCCGACTCCGGCAGCCACTTTGTCCCTCGGGAGGCCACCAAGAAAGCTGAGAGCAGCCGGCTGCAGCAGGCCA  1890
 290   V  V  M  Q  Y  A  D  S  G  S  H  F  V  P  R  E  A  T  K  K  A  E  S  S  R  L  Q  Q  A  I   319
1891  TCCAGGCCAAGGAGGTCCTGAACGGTGAGATGGAGAAGAGCCGGCGGTACGGGGCCCCGTCCTCAGCCGACCTGGGCCTGGGCAAGGCAG  1980
 320   Q  A  K  E  V  L  N  G  E  M  E  K  S  R  R  Y  G  A  P  S  S  A  D  L  G  L  G  K  A  G   349
1981  GCGGCAAGTCGGTTCCTCACCCGTACGAGTCCAGGCACGTGGTGGTCCACCCGAGCCCCTCAGACTACAGCAGTCGTGATCCTTCGGGGG  2070
 350   G  K  S  V  P  H  P  Y  E  S  R  H  V  V  V  H  P  S  P  S  D  Y  S  S  R  D  P  S  G  V   379
2071  TCCGGGCCTCTGTGATGGTCCTGCCCAACAGCAACACGCCCGCAGCTGACCTGGAGGTGCAACAGGCCACTCATCGTGAAGCCTCCCCTT  2160
```

FIG. 15b

```
380  R  A  S  V  M  V  L  P  N  S  N  T  P  A  A  D  L  E  V  Q  Q  A  T  H  R  E  A  S  P  S   409
2161 CTACCCTCAACGACAAAAGTGGCCTGCATTTAGGGAAGCCTGGCCACCGGTCCTACGCGCTCTCACCCCACACGGTCATTCAGACCACAC 2250
410  T  L  N  D  K  S  G  L  H  L  G  K  P  G  H  R  S  Y  A  L  S  P  H  T  V  I  Q  T  T  H   439
2251 ACAGTGCTTCAGAGCCACTCCCGGTGGGACTGCCAGCCACGGCCTTCTACGCAGGGACTCAACCCCCTGTCATCGGCTACCTGAGCGGCC 2340
440  S  A  S  E  P  L  P  V  G  L  P  A  T  A  F  Y  A  G  T  Q  P  P  V  I  G  Y  L  S  G  Q   469
2341 AGCAGCAAGCAATCACCTACGCCGGCAGCCTGCCCCAGCACCTGGTGATCCCCGGCACACAGCCCCTGCTCATCCCGGTCGGCAGCACTG 2430
470  Q  Q  A  I  T  Y  A  G  S  L  P  Q  H  L  V  I  P  G  T  Q  P  L  L  I  P  V  G  S  T  D   499
2431 ACATGGAAGCGTCGGGGGCAGCCCCGGCCATAGTCACGTCATCCCCCCAGTTTGCTGCAGTGCCTCACACGTTCGTCACCACCGCCCTTC 2520
500  M  E  A  S  G  A  A  P  A  I  V  T  S  S  P  Q  F  A  A  V  P  H  T  F  V  T  T  A  L  P   529
2521 CCAAGAGCGAGAACTTCAACCCTGAGGCCCTGGTCACCCAGGCCGCCTACCCAGCCATGGTGCAGGCCCAGATCCACCTGCCTGTGGTGC 2610
530  K  S  E  N  F  N  P  E  A  L  V  T  Q  A  A  Y  P  A  M  V  Q  A  Q  I  H  L  P  V  V  Q   559
2611 AGTCCGTGGCCTCCCCGGCGGCGGCTCCCCCTACGCTGCCTCCCTACTTCATGAAAGGCTCCATCATCCAGTTGGCCAACGGGGAGCTAA 2700
560  S  V  A  S  P  A  A  A  P  P  T  L  P  P  Y  F  M  K  G  S  I  I  Q  L  A  N  G  E  L  K   589
2701 AGAAGGTGGAAGACTTAAAAACAGAAGATTTCATCCAGAGTGCAGAGATAAGCAACGACCTGAAGATCGACTCCAGCACCGTAGAGAGGA 2790
590  K  V  E  D  L  K  T  E  D  F  I  Q  S  A  E  I  S  N  D  L  K  I  D  S  S  T  V  E  R  I   619
2791 TTGAAGACAGCCATAGCCCGGGCGTGGCCGTGATACAGTTCGCCGTCGGGGAGCACCGAGCCCAGGTCAGCGTTGAAGTTTTGGTAGAGT 2880
620  E  D  S  H  S  P  G  V  A  V  I  Q  F  A  V  G  E  H  R  A  Q  V  S  V  E  V  L  V  E  Y   649
2881 ATCCTTTTTTTGTGTTTGGACAGGGCTGGTCATCCTGCTGTCCGGAGAGAACCAGCCAGCTCTTTGATTTGCCGTGTTCCAAACTCTCAG 2970
650  P  F  F  V  F  G  Q  G  W  S  S  C  C  P  E  R  T  S  Q  L  F  D  L  P  C  S  K  L  S  V   679
2971 TTGGGGATGTCTGCATCTCGCTTACCCTCAAGAACCTGAAGAACGGCTCTGTTAAAAAGGGCCAGCCCGTGGATCCCGCCAGCGTCCTGC 3060
680  G  D  V  C  I  S  L  T  L  K  N  L  K  N  G  S  V  K  K  G  Q  P  V  D  P  A  S  V  L  L   709
3061 TGAAGCACTCAAAGGCCGACGGCCTGGCGGGCAGCAGACACAGGTATGCCGAGCAGGAAAACGGAATCAACCAGGGGAGTGCCCAGATGC 3150
710  K  H  S  K  A  D  G  L  A  G  S  R  H  R  Y  A  E  Q  E  N  G  I  N  Q  G  S  A  Q  M  L   739
3151 TCTCTGAGAATGGCGAACTGAAGTTTCCAGAGAAAATGGGATTGCCTGCAGCGCCCTTCCTCACCAAAATAGAACCCAGCAAGCCCGCGG 3240
740  S  E  N  G  E  L  K  F  P  E  K  M  G  L  P  A  A  P  F  L  T  K  I  E  P  S  K  P  A  A   769
3241 CAACGAGGAAGAGGAGGTGGTCGGCGCCAGAGAGCCGCAAACTGGAGAAGTCAGAAGACGAACCACCTTTGACTCTTCCTAAGCCTTCTC 3330
770  T  R  K  R  R  W  S  A  P  E  S  R  K  L  E  K  S  E  D  E  P  P  L  T  L  P  K  P  S  L   799
3331 TAATTCCTCAGGAGGTTAAGATTTGCATTGAAGGCCGGTCTAATGTAGGCAAGTAGAGGCAGCGTGGGGGAAAGGAAACGTGGCTCTCCC 3420
800  I  P  Q  E  V  K  I  C  I  E  G  R  S  N  V  G  K  *                                       829
3421 TTATCATTTGTATCCAGATTACTGTACTGTAGGCTAAAATAACACAGTATTTACATGTTATCTTCTTAATTTTAGGTTTCTGTTCTAACC 3510
3511 TTGTCATTAGAGTTACAGCAGGTGTGTCGCAGGAGACTGGTGCATATGCTTTTTCCACGAGTGTCTGTCAGTGAGCGGGCGGGAGGAAGG 3600
3601 GCACAGCAGGAGCGGTCAGGGCTCCAGGCATCCCCGGGGAAGAAAGGAACGGGGCTTCACAGTGCCTGCCTTCTCTAGCGGCACAGAAGC 3690
3691 AGCCGGGGGCGCTGACTCCCGCTAGTGTCAGGAGAAAAGTCCCGTGGGAAGAGTCCTGCAGGGGTGCAGGGTTGCACGCATGTGGGGGTG 3780
3781 CACAGGCGCTGTGGCGGCGAGTGAGGGTCTCTTTTTCTCTGCCTCCCTCTGCCTCACTCTCTTGCTATCGGCATGGGCCGGGGGGGTTCA 3870
3871 GAGCAGTGTCCTCCTGGGGTTCCCACGTGCAAAATCAACATCAGGAACCCAGCTTCAGGGCATCGCGGAGACGCGTCAGATGGCAGATTT 3960
3961 GGAAAGTTAACCATTTAAAAGAACATTTTTCTCTCCAACATATTTTACAATAAAAGCAACTTTTAATTGTATAGATATATATTTCCCCCT 4050
4051 ATGGGGCCTGACTGCACTGATATATATTTTTTTTAAAGAGCAACTGCCACATGCGGGATTTCATTTCTGCTTTTTACTAGTGCAGCGATG 4140
```

FIG. 15c

| | | |
|---|---|---|
| 4141 | TCACCAGGGTGTTGTGGTGGACAGGGAAGCCCCTGCTGTCATGGCCCCACATGGGGTAAGGGGGGTTGGGGGTGGGGGAGAGGGAGAGAG | 4230 |
| 4231 | CGAACACCCACGCTGGTTTCTGTGCAGTGTTAGGAAAACCAATCAGGTTATTGCATTGACTTCACTCCCAAGAGGTAGATGCAAACTGCC | 4320 |
| 4321 | CTTCAGTGAGAGCAACAGAAGCTCTTCACGTTGAGTTTGCGAAATCTTTTTGTCTTTGAACTCTAGTACTGTTTATAGTTCATGACTATG | 4410 |
| 4411 | GACAACTCGGGTGCCACTTTTTTTTTTTTTCAGATTCCAGTGTGACATGAGGAATTAGATTTTGAAGATGAGCATATATTACTATCTTTAA | 4500 |
| 4501 | GCATTTAAAAATACTGTTCACACTTTATTACCAAGCATCTTGGTCTCTCATTCAACAAGTACTGTATCTCACTTTAAACTCTTTGGGGAA | 4590 |
| 4591 | AAAACAAAAACAAAAAAAACTAAGTTGCTTTCTTTTTTTCAACACTGTAACTACATTTCAGCTCTGCAGAATTGCTGAAGAGCAAGATAT | 4680 |
| 4681 | TGAAAGTTTCAATGTGGTTTAAAGGGATGAATGTGAATTATGAACTAGTATGTGACAATAAATGACCACCAAGTACTACCTGACGGGAGG | 4770 |
| 4771 | CACTTTTCACTTTGATGTCTGAGAATCAGTTCAAGGCATATGCAGAGTTGGCAGAGAAACTGAGAGAAAAGGGATGGAGAAGAGAATACT | 4860 |
| 4861 | CATTTTTGTCCAGTGTTTTTCTTTTTAAGATGAACTTTTAAAGAACCTTGCGATTTGCACATATTGAGTTTATAACTTGTGTGATATTCC | 4950 |
| 4951 | TGCAGTTTTTATCCAATAACATTGTGGGAAAGGTTTGGGGGACTGAACGAGCATAAATAAATGTAGCAAAATTTCTTTCTAACCTGCCTA | 5040 |
| 5041 | AACTCTAGGCCATTTTATAAGGTTATGTTCCTTTGAAAATTCATTTTGGTCTTTTTACCACATCTGTCACAAAAAGCCAGGTCTTAGCGG | 5130 |
| 5131 | GCTCTTAGAAACTCTGAGAATTTTCTTCAGATTCATTGAGAGAGTTTTCCATAAAGACATTTATATATGTGAGCAAGATTTTTTTTAAAC | 5220 |
| 5221 | AATTACTTTATTATTGTTGTTATTAATGTTATTTTCAGAATGGCTTTTTTTTTCTATTCAAAATCAAATCGAGATTTAATGTTTGGTACA | 5310 |
| 5311 | AACCCAGAAAGGGTATTTCATAGTTTTTAAACCTTTCATTCCCAGAGATCCGAAATATCATTTGTGGGTTTTGAATGCATCTTTAAAGTG | 5400 |
| 5401 | CTTTAAAAAAAAGTTTTATAAGTAGGGAGAAATTTTTAAATATTCTTACTTGGATGGCTGCAACTAAACTGAACAAATACCTGACTTTTC | 5490 |
| 5491 | TTTTACCCCATTGAAAATAGTACTTTCTTCGTTTCACAAATTAAAAAAAAAATCTGGTATCAACCCACATTTTGGCTGTCTAGTATTCAT | 5580 |
| 5581 | TTACATTTAGGGTTCACCAGGACTAATGATTTTTATAAACCGTTTTCTGGGGTGTACCAAAAACATTTGAATAGGTTTAGAATAGCTAGA | 5670 |
| 5671 | ATAGTTCCTTGACTTTCCTCGAATTTCATTACCCTCTCAGCATGCTTGCAGAGAGCTGGGTGGGCTCATTCTTGCAGTCATACTGCTTAT | 5760 |
| 5761 | TTAGTGCTGTATTTTTTAAACGTTTCTGTTCAGAGAACTTGCTTAATCTTCCATATATTCTGCTCAGGGCACTTGCAATTATTAGGTTTT | 5850 |
| 5851 | GTTTTTCTTTTTGTTTTTTAGCCTTTGATGGTAAGAGGAATACGGGCTGCCACATAGACTTTGTTCTCATTAATATCACTATTTACAACT | 5940 |
| 5941 | CATGTGGACTCAGAAAAACACACACCACCTTTTGGCTTACTTCGAGTATTGAATTGACTGGATCCACTAAACCAACACTAAGATGGGAAA | 6030 |
| 6031 | ACACACATGGTTTGGAGCAATAGGAACATCATCATAATTTTTGTGGTTCTATTTCAGGTATAGGAATTATAAAATAATTGGTTCTTTCTA | 6120 |
| 6121 | AACACTTGTCCCATTTCATTCTCTTGCTTTTTTAGCATGTGCAATACTTTCTGTGCCAATAGAGTCTGACCAGTGTGCTATATAGTTAAA | 6210 |
| 6211 | GCTCATTCCCTTTTGGCTTTTTCCTTGTTTGGTTGATCTTCCCCATTCTGGCCAGAGCAGGGCTGGAGGGAAGGAGCCAGGAGGGAGAGA | 6300 |
| 6301 | GCCTCCCACCTTTCCCCTGCTGCGGATGCTGAGTGCTGGGGCGGGGAGCCTTCAGGAGCCCCGTGCGTCTGCCGCCACGTTGCAGAAAGA | 6390 |
| 6391 | GCCAGCCAAGGAGACCCGGGGGAGGAACCGCAGTGTCCCCTGTCACCACACGGAATAGTGAATGTGGAGTGTGGAGAGGAAGGAGGCAGA | 6480 |
| 6481 | TTCATTTCTAAGACGCACTCTGGAGCCATGTAGCCTGGAGTCAACCCATTTTCCACGGTCTTTTCTGCAAGTGGGCAGGCCCCTCCTCGG | 6570 |
| 6571 | GGTCTGTGTCCTTGAGACTTGGAGCCCTGCCTCTGAGCCTGGACGGGAAGTGTGGCCTGTTGTGTGTGTGCGTTCTGAGCGTGTTGGCCA | 6660 |
| 6661 | GTGGCTGTGGAGGGGACCACCTGCCACCCACGGTCACCACTCCCTTGTGGCAGCTTTCTCTTCAAATAGGAAGAACGCACAGAGGGCAGG | 6750 |
| 6751 | AGCCTCCTGTTTGCAGACGTTGGCGGGCCCCGAGGCTCCCAGAGCAGCCTCTGTCACCGCTTCTGTGTAGCAAACATTAACGATGACAGG | 6840 |
| 6841 | GGTAGAAATTCTTCGGTGCCGTTCAGCTTACAAGGATCAGCCATGTGCCTCTGTACTATGTCCACTTTGCAATATTTACCGACAGCCGTC | 6930 |
| 6931 | TTTTGTTCTTTCTTTCCTGTTTTCCATTTTTAAACTAGTAACAGCAGGCCTTTTGCGTTTACAATGGAACACAATCACCAAGAAATTAGT | 7020 |
| 7021 | CAGGGCGAAAAGAAAAAAATAATACTATTAATAAGAAACCAACAAACAAGAACCTCTCTTTCTAGGGATTTCTAAATATATAAAATGACT | 7110 |
| 7111 | GTTCCTTAGAATGTTTAACTTAAGAATTATTTCAGTTTGTCTGGGCCACACTGGGGCAGAGGGGGGAGGGAGGGATACAGAGATGGATGC | 7200 |
| 7201 | CACTTACCTCAGATCTTTTAAAGTGGAAATCCAAATTGAATTTTCATTTGGACTTTCAGGATAATTTTCTATGTTGGTCAACTTTTCGTT | 7290 |
| 7291 | TTCCCTAACTCACCCAGTTTAGTTTGGGATGATTTGATTTCTGTTGTTGTTGATCCCATTTCTAACTTGGAATTGTGAGCCTCTATGTTT | 7380 |
| 7381 | TCTGTTAGGTGAGTGTGTTGGGTTTTTTCCCCCCACCAGGAAGTGGCAGCATCCCTCCTTCTCCCCTAAAGGGACTCTGCGGAACCTTTC | 7470 |

FIG. 15d

```
7471  ACACCTCTTTCTCAGGGACGGGGCAGGTGTGTGTGTGGTACACTGACGTGTCCAGAAGCAGCACTTTGACTGCTCTGGAGTAGGGTTGTA  7560
7561  CAATTTCAAGGAATGTTTGGATTTCCTGCATCTTGTGGATTACTCCTTAGATACCGCATAGATTGCAATATAATGCTGCATGTTCAAGAT  7650
7651  GAACAGTAGCTCCTAGTAATCATAAAATCCACTCTTTGCACAGTTTGATCTTTACTGAAATATGTTGCCAAAATTTATTTTTGTTGTTGT  7740
7741  AGCTCTGGATTTTGTTTTGTTTTGTTTTTTAAGGAAACGATTGACAATACCCTTTAACATCTGTGACTACTAAGGAAACCTATTTCTTTC  7830
7831  ATAGAGAGAAAAATCTCCAATGCTTTTGAAGACACTAATACCGTGCTATTTCAGATATGGGTGAGGAAGCAGAGCTCTCGGTACCGAAGG  7920
7921  CCGGGCTTCTTGAGCTGTGTTGGTTGTCATGGCTACTGTTTCATGAACCACAAGCAGCTCAACAGACTGGTCTGTTGCCTTCTGAAACCC  8010
8011  TTTGCACTTCAATTTGCACCAGGTGAAAACAGGGCCAGCAGACTCCATGGCCCAATTCGGTTTCTTCGGTGGTGATGTGAAAGGAGAGAA  8100
8101  TTACACTTTTTTTTTTTTTTAAGTGGCGTGGAGGCCTTTGCTTCCACATTTGTTTTAACCCAGAATTTCTGAAATAGAGAATTTAAGAAC  8190
8191  ACATCAAGTAATAAATATACAGAGAATATACTTTTTTATAAAGCACATGCATCTGCTATTGTGTTGGGTTGGTTTCCTCTCTTTTCCACG  8280
8281  GACAGTGTTGTGTTTCTGGCATAGGGAAACTCCAAACAACTTGCACACCTCTACTCCGGAGCTGAGATTTCTTTTACATAGATGACCTCG  8370
8371  CTTCAAATACGTTACCTTACTGATGATAGGATCTTTTCTTGTAGCACTATACCTTGTGGGAATTTTTTTTTAAATGTACACCTGATTTGA  8460
8461  GAAGCTGAAGAAAACAAAATTTTGAAGCACTCACTTTGAGGAGTACAGGTAATGTTTTAAAAAATTGCACAAAAGAAAAATGAATGTCGA  8550
8551  AATGATTCATTCAGTGTTTGAAAGATATGGCTCTGTTGAAACAATGAGTTTCATACTTTGTTTGTAAAAAAAAAAAGCAGAGAAGGGTTG  8640
8641  AAAGTTACATGTTTTTTTGTATATAGAAATTTGTCATGTCTAAATGATCAGATTTGTATGGTTATGGCCTGGAAGAATTACTACGTAAAA  8730
8731  GGCTCTTAAACTATACCTATGCTTATTGTTATTTTTGTTACATATAGCCCTCGTCTGAGGGAGGGGAACTCGGTATTCTGCGATTTGAGA  8820
8821  ATACTGTTCATTCCTATGCTGAAAGTACTTCTCTGAGCTCCCTTCTTAGTCTAAACTCTTAAGCCATTGCAACTTCTTTTTCTTCAGAGA  8910
8911  TGATGTTTGACATTTTCAGCACTTCCTGTTCCTATAAACCCAAAGAATATAATCTTGAACACGAAGTGTTTGTAACAAGGGATCCAGGCT  9000
9001  ACCAATCAAACAGGACTCATTATGGGGACAAAAAAAAAAAAAATTATTTCACCTTCTTTCCCCCCACACCTCATTTAAATGGGGGGAGTA  9090
9091  AAAACATGATTTCAATGTAAATGCCTCATTTTATTTTAGTTTTATTTTGATTTTTATTTAATATAAAGAGGCCAGAATAAATACGGAGCA  9180
9181  TCTTCTCAGAATAGTATTCCTGTCCAAAAATCAAGCCGGACAGTGGAAACTGGACAGCTGTGGGGATATTAAGCACCCCCACTTACAATT  9270
9271  CTTAAATTCAGAATCTCGTCCCCTCCCTTCTCGTTGAAGGCAACTGTTCTGGTAGCTAACTTTCTCCTGTGTAATGGCGGGAGGGAACAC  9360
9361  CGGCTTCAGTTTTTCATGTCCCCATGACTTGCATACAAATGGTTCAACTGTATTAAAATTAAGTGCATTTGGCCAATAGGTAGTATCTAT  9450
9451  ACAATAACAACAATCTCTAAGAATTTCCATAACTTTTCTTATCTGAAAGGACTCAAGTCTTCCACTGCAGATACATTGGAGGCTTCACCC  9540
9541  ACGTTTTCTTTCCCTTTAGTTTGTTTGCTGTCTGGATGGCCAATGAGCCTGTCTCCTTTTCTGTGGCCAATCTGAAGGCCTTCGTTGGAA  9630
9631  GTGTTGTTCACAGTAATCCTTACCAAGATAACATACTGTCCTCCAGAATACCAAGTATTAGGTGACACTAGCTCAAGCTGTTGTCTTCAG  9720
9721  AGCAGTTACCAAGAAGCTCGGTGCACAGGTTTTCTCTGGTTCTTACAGGAACCACCTACTCTTTCAGTTTTCTGGCCCAGGAGTGGGGTA  9810
9811  AATCCTTTAGTTAGTGCATTTGAACTTGGTACCTGTGCATTCAGTTCTGTGAATACTGCCCTTTTTGGCGGGGTTTCCTCATCTCCCCAG  9900
9901  CCTGAACTGCTCAACTCTAAACCCAAATTAGTGTCAGCCGAAAGGAGGTTTCAAGATAGTCCTGTCAGTATTTGTGGTGACCTTCAGATT  9990
9991  AGACAGTCTTCATTTCCAGCCAGTGGAGTCCTGGCTCCAGAGCCATCTCTGAGACTCCGTACTACTGGATGTTTTAATATCAGATCATTA  10080
10081 CCCACCATATGCCTCCCACAGGCCAAGGGAAAACAGACACCAGAACTTGGGTTGAGGGCACTACCAGACTGACATGGCCAGTACAGAGGA  10170
10171 GAACTAGGGAAGGAATGATGTTTTGCACCTTATTGAAAAGAAAATTTTAAGTGCATACATAATAGTTAAGAGCTTTTATTGTGACAGGAG  10260
10261 AACTTTTTTCCATATGCGTGCATACTCTCTGTAATTCCAGTGTAAAATATTGTACTTGCACTAGCTTTTTTAAACAAATATTAAAAAATG  10350
10351 GAAGAATTCATATTCTATTTTCTAATCGTGGTGTGTCTATTTGTAGGATACACTCGAGTCTGTTTATTGAATTTTATGGTCCCTTTCTTT  10440
10441 GATGGTGCTTGCAGGTTTTCTAGGTAGAAATTATTTCATTATTATAATAAAACAATGTTTGATTCAAAATTTGAACAAAATTGTTTTAAA  10530
10531 TAAATTGTCTGTATACCAGTACAAGTTTATTGTTTCAGTATACTCGTACTAATAAAATAACAGTGCCAATTGCAAAAAAAAAAAAAAAAA  10620
10621 AAAAAAAAAAAAAAAAAAAAAAAAAAAAAAAAAAAAAAAA  10660
```

FIG. 17

| | | | | |
|---|---|---|---|---|
| | | EXON 1 | 157<br>TTTACA gtaagtga | |
| gtttctatgcatag | 158<br>GTTTTACC | EXON 2 | 206<br>GGAAAG gtatatgg | |
| ctcgaccattgcag | 207<br>GAGCATCG | EXON 3 | 321<br>TGTCAG gtgagagt | |
| ttgtttgactgcag | 322<br>CATACTGG | EXON 4 | 447<br>TTTTTG gtaagtca | |
| ttttataattacag | 448<br>GTCTAGGC | EXON 5 | 575<br>GTACAG gtaaacat | |
| tttttctattccag | 576<br>TTTTCCAA | EXON 6 | 637<br>CATAGG gtgagtga | |
| tatttccatgctag | 638<br>GTATTTCT | EXON 7 | 775<br>AATGTT gtaagtta | |
| cttccctttcccag | 776<br>CATCCAGA | EXON 8 | 2855<br>GCCCAG gtaacgtt | |
| ccctgtttccacag | 2857<br>GTCAGCGT | EXON 9 | | |
| YYYYYYYYYYNCAG | | CONSENSUS | AG GTRAGT | |

FIG. 18

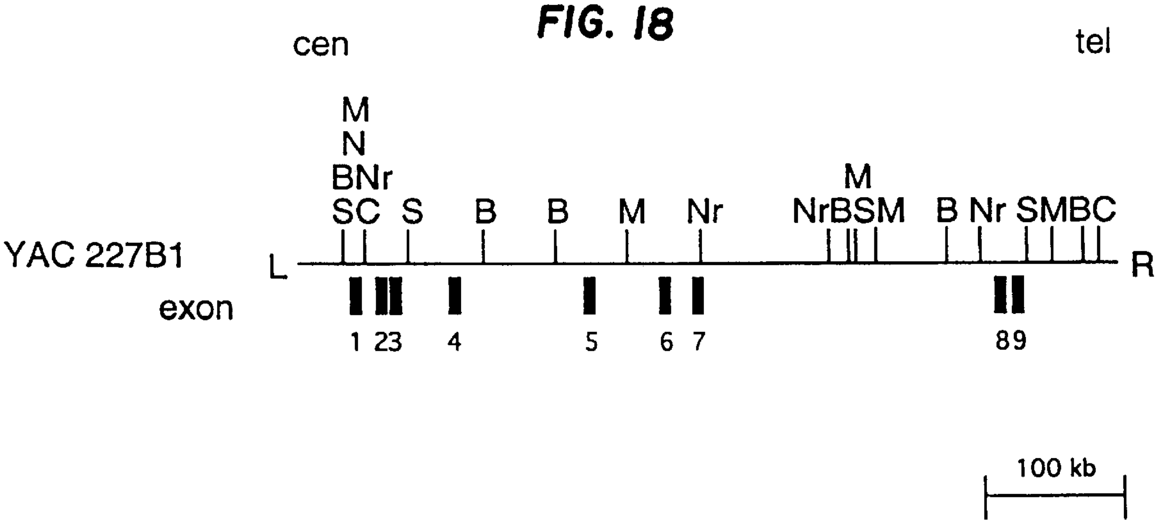

GENE SEQUENCE FOR SPINOCEREBELLAR ATAXIA TYPE 1 AND METHOD FOR DIAGNOSIS

CROSS-REFERENCE TO RELATED APPLICATIONS

This application is a Continuation-In-Part of U.S. application Ser. No. 08/084,365 (filed Jun. 29, 1993) (abandoned), which is incorporated herein by reference.

STATEMENT OF GOVERNMENT RIGHTS

The present invention was made with government support under Grant Nos. NS 22920 and 27699, awarded by the National Institutes of Health. The Government has certain rights in this invention.

BACKGROUND OF THE INVENTION

The spinocerebellar ataxias are a heterogeneous group of degenerative neurological disorders with variable clinical features resulting from degeneration of the cerebellum, brain stem, and spinocerebellar tracts. The clinical symptoms include ataxia, dysarthria, ophthalmoparesis, and variable degrees of motor weakness. The symptoms usually begin during the third or fourth decade of life, however, juvenile onset has been identified. Typically, the disease worsens gradually, often resulting in complete disability and death 10–20 years after the onset of symptoms. Individuals with juvenile onset spinocerebellar ataxias, however, typically have more rapid progression of the phenotype than the late onset cases. A method for diagnosing spinocerebellar ataxias would provide a significant step toward its treatment.

Spinocerebellar ataxia type 1 (SCA1) is an autosomal dominant disorder which is genetically linked to the short arm of chromosome 6 based on linkage to the human major histocompatibility complex (HLA). See, for example, H. Yakura et al., *N. Engl. J. Med.,* 291, 154–155 (1974); and J. F. Jackson et al., *N. Engl. J. Med.,* 296, 1138–1141 (1977). SCA1 has been shown to be tightly linked to the marker D6S89 on the short arm of chromosome 6, telomeric to HLA. See, for example, L. P. W. Ranum et al., *Am. J. Hum. Genet.,* 49, 31–41 (1991); and H. Y. Zoghbi et al., *Am. J. Hum. Genet.,* 49, 23–30 (1991). Recently, two families with dominantly inherited ataxia failed to show detectable linkage with HLA markers but were found to have SCA1 when studied for linkage to D6S89, demonstrating the superiority of the latter marker for study of ataxia families. See, for example B. J. B. Keats et al., *Am. J. Hum. Genet.,* 49, 972–977 (1991). The identification and cloning of the SCA1 gene could provide methods of detection that would be extremely valuable for both family counseling and planning medical treatment.

SUMMARY OF THE INVENTION

The present invention is directed to a portion of an isolated 1.2-Mb region of DNA from the short arm of chromosome 6 containing a highly polymorphic CAG repeat region in the SCA1 gene. This CAG repeat region is unstable (i.e., highly variable within a population) and is expanded in individuals with the autosomal dominant neurodegenerative disorder spinocerebellar ataxia type 1 (i.e., affected individuals generally have more than 36 CAG repeats). Southern and PCR analyses of the CAG repeat region demonstrate correlation between the size of the expanded repeat region and the age-of-onset of the disorder (with larger alleles, i.e., more repeat units, occurring in juvenile cases), and severity of the disorder (with larger alleles, i.e., more repeat units, occurring in the more severe cases).

Specifically, the present invention provides a nucleic acid molecule containing a CAG repeat region of an isolated autosomal dominant spinocerebellar ataxia type 1 gene (herein referred to as "SCA1"), which is located within the short arm of chromosome 6. The SCA1 gene contains a region that encodes a protein herein referred to as "ataxin-1." The nucleic acid molecule of the present invention can be a single or a double-stranded polynucleotide. It can be genomic DNA, cDNA, or mRNA of any size as long as it includes the CAG repeat region of an isolated SCA1 gene. Preferably, the nucleic acid molecule includes the SCA1 coding region and is of about 2.4–11 kb in length. It can be the entire SCA1 gene (whether genomic DNA or a transcript thereof) or any fragment thereof that contains the CAG region of the gene. One such fragment is an EcoRI fragment of the SCA1 gene, i.e., a fragment obtained through digestion with EcoRI endonuclease restriction enzyme, containing about 3360 base pairs having therein a polymorphic CAG repeat region. By polymorphic CAG repeat region it is meant that there are repeating CAG trinucleotides in this portion of the gene that can vary in the number of CAG trinucleotides. The number of trinucleotide repeats can vary from as few as 19, for example, to as many as 81, for example, and larger.

For a normal individual, $n \leqq 36$ in the $(CAG)_n$ region, i.e., n=2–36, and typically n=19–36. This region in a normal allele of the SCA1 gene is optionally interrupted with CAT trinucleotides. Typically, there are no more than about 3 CAT trinucleotides, either individually or in combination, within any $(CAG)_n$ region. The $(CAG)_n$ region of this isolated sequence is unstable, i.e., highly variable within a population, and larger, i.e., expanded, in individuals who have symptoms of the disease, or who are likely to develop symptoms of the disease. For an affected individual, i.e., an individual with an affected allele of the SCA1 gene, $n > 36$ in the $(CAG)_n$ region, and typically $n \geqq 43$. One isolated DNA molecule of the SCA1 gene is about 3360 base pairs in length as shown in FIG. 1. The sequences of a portion of the EcoRI fragment within the SCA1 gene of several affected individuals is shown in FIG. 2 (SEQ ID NO:2), (SEQ ID NO:3), (SEQ ID NO:4), (SEQ ID NO:5), (SEQ ID NO:6). The entire 10,660 nucleotides of the SCA1 gene transcript are shown in FIG. 15 (SEQ ID NO:8) and (SEQ ID NO:9) (the entire SCA1 gene spans about 450 kb of genomic DNA).

The present invention is also directed to isolated oligonucleotides, particularly primers for use in PCR techniques and probes for diagnosing the neurodegenerative disorder SCA1. The oligonucleotides have at least about 11 nucleotides and hybridize to a nucleic acid molecule containing a CAG repeat region of an isolated SCA1 gene. The hybridization can occur to any portion of a nucleic acid molecule containing a CAG repeat region of the SCA1 gene. Preferably, the oligonucleotides hybridize to a 3.36 kb EcoRI fragment of an SCA1 gene having a CAG repeat region. Alternatively stated, each oligonucleotide is substantially complementary (having greater than 65% homology) to a nucleotide sequence having a CAG repeat region, i.e., a $(CAG)_n$ region, preferably to a 3.36-kb EcoRI fragment of the SCA1 gene. If the oligonucleotide is a primer the molecule preferably contains at least about 16 nucleotides and no more than about 35 nucleotides. Furthermore, preferred primers are chosen such that they produce a primed product of about 70–350 base pairs, preferably about 100–300 base pairs. More preferably, the primers are chosen such that nucleotide sequence is complementary to a portion of a strand of an affected or a normal allele within about 150 nucleotides on either side of the $(CAG)_n$ region, including directly adjacent to the $(CAG)_n$ region. Most preferably, the primer is selected from the group consisting of CCGGAGCCCTGCTGAGGT (CAG-a) (SEQ ID NO:26), CCAGACGCCGGGACAC (CAG-b) (SEQ ID NO:27), AACTGGAAATGTGGACGTAC (Rep-1) (SEQ ID NO:28) CAACATGGGCAGTCTGAG (Rep-2) (SEQ ID NO:29), CCACCACTCCATCCCAGC (GCT-435) (SEQ ID NO:30), TGCTGGGCTGGTGGGGGG (GCT-214) (SEQ ID NO:31), CTCTCGGCTTTCTTGGTG (Pre-1) (SEQ ID NO:32), and GTACGTCCACATTTCCAGTT (Pre-2) (SEQ ID NO:33). These primers substantially correspond to those shown in FIG. 3 (SEQ ID NO:7).

They can be used in any combination for sequencing or producing amplified nucleic acid molecules, e.g., DNA molecules, using various PCR techniques. Preferably, for amplification of the DNA molecule characteristic of the SCA1 disorder, Rep-1 and Rep-2 is the primer pair used. As used herein, the term "amplified DNA molecule" refers to DNA molecules that are copies of a portion of DNA and its complementary sequence. The copies correspond in nucleotide sequence to the original DNA sequence and its complementary sequence. The term "complement", as used herein, refers to a DNA sequence that is complementary (having greater than 65% homology) to a specified DNA sequence. The term "primer pair", as used herein, means a set of primers including a 5' upstream primer that hybridizes with the 5' end of the DNA molecule to be amplified and a 3' downstream primer that hybridizes with the complement of the 3' end of the molecule to be amplified.

Using the primers of the present invention, PCR technology can be used in the diagnosis of the neurological disorder SCA1 by detecting a region of greater than about 36 CAG repeating trinucleotides, preferably at least 43 repeating CAG trinucleotides. Generally, this involves treating separate complementary strands of the DNA molecule containing a region of repeating CAG codons with a molar excess of two oligonucleotide primers, extending the primers to form complementary primer extension products which act as templates for synthesizing the desired molecule containing the CAG repeating units, and detecting the molecule so amplified.

An oligonucleotide that can be used as a gene probe for identifying a nucleic acid molecule, e.g., a DNA molecule, containing a CAG repeat region of the SCA1 gene is also provided. The gene probe can be used for distinguishing between the normal and the larger affected alleles of the SCA1 gene. The gene probe can be a portion of a nucleotide sequence of the SCA1 gene itself (e.g., a 3.36-kb EcoRI fragment or portion thereof), complementary to it, or hybridizable to it or the complement. It is of a size suitable for forming a stable duplex, i.e., having at least about 11 nucleotides, preferably having at least about 15 nucleotides, more preferably having at least about 100 nucleotides (for effective Southern blotting), and most preferably having at least about 200 nucleotides. The probe can contain any portion of the $(CAG)_n$ region, although this is not a requirement. It is desirable, however, for the probe to contain a portion of the nucleic acid molecule on either side of the $(CAG)_n$ region. There is generally no maximum size limitation for such probes. In fact, the entire SCA1 gene could be a probe.

The gene probe of the present invention is useable in a method of diagnosing a patient for SCA1. A particularly preferred method of diagnosis involves detecting the presence of a DNA molecule containing a CAG repeat region of the SCA1 gene. Specifically, the method includes the steps of digesting genomic DNA with a restriction endonuclease to obtain DNA fragments; preferably, separating the fragments by size using gel electrophoresis; probing said DNA fragments under hybridizing conditions with a detectably labeled gene probe that hybridizes to a nucleic acid molecule containing a CAG repeat region of an isolated SCA1 gene; detecting probe DNA which has hybridized to said DNA fragments; and analyzing the DNA fragments for a $(CAG)_n$ region characteristic of the normal or affected forms of the SCA1 gene.

The present invention also provides a protein (or portions thereof) encoded by the SCA1 gene and antibodies (polyclonal or monoclonal) produced from the protein or portions thereof. The antibodies can be used in methods of isolating antigenic protein expressed by the SCA1 gene. For example, they can be added to a biological sample containing the antigenic protein to form an antibody-antigen complex, which can be isolated from the sample and exposed to amino acid sequencing of the antigenic protein. This can be done while the protein is still complexed with the antibody.

Thus, the present invention provides methods to determine the presence or absence of an affected form of the SCA1 gene, which can be based on RNA- or DNA-based detection methods (preferably, the methods involve isolating and analyzing genomic DNA) or on protein-based detection methods. These methods include, for example, PCR-based methods, direct nucleic acid sequencing, measuring expression of the SCA1 gene by measuring the amount of mRNA expressed or by measuring the amount of ataxin-1 protein expressed. The methods of the present invention also include determining the size of the repeat region of the nucleic acid or amino acid molecules.

As used herein, the term "isolated (and purified)" means that the nucleic acid molecule, gene, or oligonucleotide is essentially free from the remainder of the human genome and associated cellular or other impurities. This does not mean that the product has to have been extracted from the human genome; rather, the product could be a synthetic or cloned product for example. As used herein, the term "nucleic acid molecule" means any single or double-stranded RNA or DNA molecule, such as mRNA, cDNA, and genomic DNA.

As used herein, the term "SCA1 gene" means the deoxyribopolynucleotide located within the short arm of chromosome 6 between markers D6S89 and D6S274 of about 450 kb (10.5–11 kb transcript) containing an unstable CAG repeat region. This term, therefore, refers to numerous unique genes that are substantially the same except for the content of the CAG repeat region. A representative example of the SCA1 gene transcript for a normal individual is shown in FIG. 15. Included within the scope of this term is any ribo- or deoxyribo-polynucleotide containing zero, one or more nucleotide substitutions that also encodes the protein ataxin-1. Included in the term "SCA1 gene" is any polynucleotide as described in the previous sentence that has different numbers of CAG and/or CAT repeats in the polymorphic CAG repeat region. It is understood also that the term "SCA1 gene" includes both the polypeptide-encoding region and the regions that encode the 5' and 3' untranslated segments of the mRNA for SCA 1. Although the SCA1 gene described herein is described in terms of the human genome, it is envisioned that other mammals, e.g., mice, may also have a very similar gene containing a CAG repeat region that could be used to produce oligonucleotides, for example, that are useful in diagnosing the SCA1 disorder in humans.

As used herein, the term "ataxin-1 " means the gene product of the SCA1 gene, i.e., protein encoded by the open reading frame of the SCA1 gene and any protein substantially equivalent thereto, including all proteins of different lengths (e.g., 20–90 kD, preferably 60–90 kD) encoded by said open reading frame which start at each in-frame ATG translation start site. The term "ataxin-1 " further includes all proteins with essentially the same N-terminal and C-terminal sequences but different numbers of glutamine (Q) and/or histadine (H) repeats (primarily glutamine repeats) in the polymorphic repeat region.

As used herein, the term "polymorphic CAG repeat region" or simply "CAG repeat region" means that region of the SCA1 gene that encodes a string of polyglutamate residues that varies in number from individual allele to individual allele, and which can range in number from 2 to 80 or more. Moreover, the polymorphic CAG repeat regions can contain CAT (encoding histidine) in place of CAG, although CAT is much less common than CAG in this region. It is to be understood that when referring to nucleic acid molecules containing the CAG repeat region, this includes RNA molecules containing the corresponding GUC repeat region.

As used herein, an "affected" gene refers to the allele of the SCA1 gene that, when present in an individual, is the cause of spinocerebellar ataxia type 1, and an "affected" individual has the symptoms of autosomal dominant spinocerebellar ataxia type 1. Individuals with only "normal" SCA1 genes, do not possess the symptoms of SCA1. The term "allele" means a genetic variation associated with a coding region; that is, an alternative form of the gene.

As used herein, "hybridizes" means that the oligonucleotide forms a noncovalent interaction with the stringency target nucleic acid molecule under standard conditions. The hybridizing oligonucleotide may contain nonhybridizing nucleotides that do not interfere with forming the noncovalent interaction, e.g., a restriction enzyme recognition site to facilitate cloning.

BRIEF DESCRIPTION OF THE DRAWINGS

FIG. 1. Sequence (SEQ ID NO:1) of the 3.36 kb EcoRI fragment of the normal SCA1 gene located within the short arm of chromosome 6. It is within this fragment that mutations occur in the CAG repeat region which are associated with autosomal dominant spinocerebellar ataxia type 1.

FIG. 2. Sequence information for five affected individuals in the CAG repeat region, i.e., the CAG trinucleotide repeat, and its flanking regions of the SCA1 gene located within a short arm of chromosome 6 (SEQ ID NO:2), (SEQ ID NO:3), (SEQ ID NO:4), (SEQ ID NO:5), (SEQ ID NO:6).

FIG. 3. Sequence of the CAG trinucleotide repeat and its flanking regions (SEQ ID NO:7). About 500 nucleotides in a single strand of DNA of the 3.36 kb EcoRI fragment of the SCA1 gene shown in FIG. 1 is represented. The locations of PCR primers are shown by solid lines with arrowheads.

FIG. 10*a:* TaqI-digested DNA from a TX-SCA1 kindred. The unaffected spouse has a single fragment at 2830-bp. The affected individual with onset at 25 years of age has the 2830-bp fragment as well as a 2930-bp fragment. The affected child with onset at 4 years inherited the normal 2830-bp from her mother, and has a new fragment of 3000-bp not seen in either parent. FIG. 10*b:* TaqI-digested DNA from individuals from a MN-SCA1 kindred. The unaffected spouse and the unaffected sibling have a 2830-bp fragment. The two affected brothers have the 2830-bp fragment as well as an expanded fragment of 2900-bp in the sib with onset at 25 years and 2970-bp in the sib with onset at 9 years. FIG. 10*c:* BstNI-digested DNA from the TX-SCA1 kindred. Lanes 1–3 are from the same kindred depicted in (A). The normal fragment size is 530-bp, in individuals with onset at 25–30 years (lanes 1 and 4) the fragment expands to 610-bp. In the individual with onset at 15 years of age (lane 7) the fragment size is 640-bp, and in the individual with onset at 4 years (lane 3) the fragment size is 680-bp. The DNA in lane 5 is from a 14 year old child who is asymptomatic.

FIG. 15. The sequence of the SCA1 transcript (SEQ ID NO:8). The sequences of primers 9b, 5F and 5R (bp 129-147, bp 173-191 and bp 538-518 respectively in the 5' to 3' orientation) are underlined. The protein sequence encoded by the DNA is shown below the DNA sequence (SEQ ID NO:9). The CAG repeat region is from about bp 1524 to about bp 1613.

FIG. 17. Intron-exon boundaries of the SCA1 gene (SEQ ID NO:10), (SEQ ID NO:11), (SEQ ID NO:12), (SEQ ID NO:13), (SEQ ID NO:14), (SEQ ID NO:15), (SEQ ID NO:16), (SEQ ID NO:17), (SEQ ID NO:18), (SEQ ID NO:19), (SEQ ID NO:20), (SEQ ID NO:21), (SEQ ID NO:22); (SEQ ID NO:23), (SEQ ID NO:24). Splice acceptor and splice donor sites are indicated in bold letters. The numbers at the beginning and the end of each exon refer to the position in the composite sequence of SCA1 in FIG. 15 (SEQ ID NO:8). Uppercase letters indicate exon sequences, lowercase letters indicate intron sequences. Y=pyrimidine; R=purine; N=undefined.

FIG. 18. Genomic structure of the SCA1 gene. The nine exons of the SCA1 gene (solid rectangles not drawn to scale) were localized based on the restriction map of the SCA1 region by Southern analysis using rare cutter DNA digests from several YAC clones. A representative map using YAC clone 227B1, which encompasses the SCA1 gene, is shown. The restriction map of this YAC has been confirmed by analysis of four overlapping YAC clones in the region. The centromere-telomere orientation is indicated by CEN-TEL, respectively. L=left YAC end; R=right YAC end; B=BssHII; C=CspI; M=MluI; N=NotI; Nr=NruI; S=SacII.

DETAILED DESCRIPTION

Figure 4:
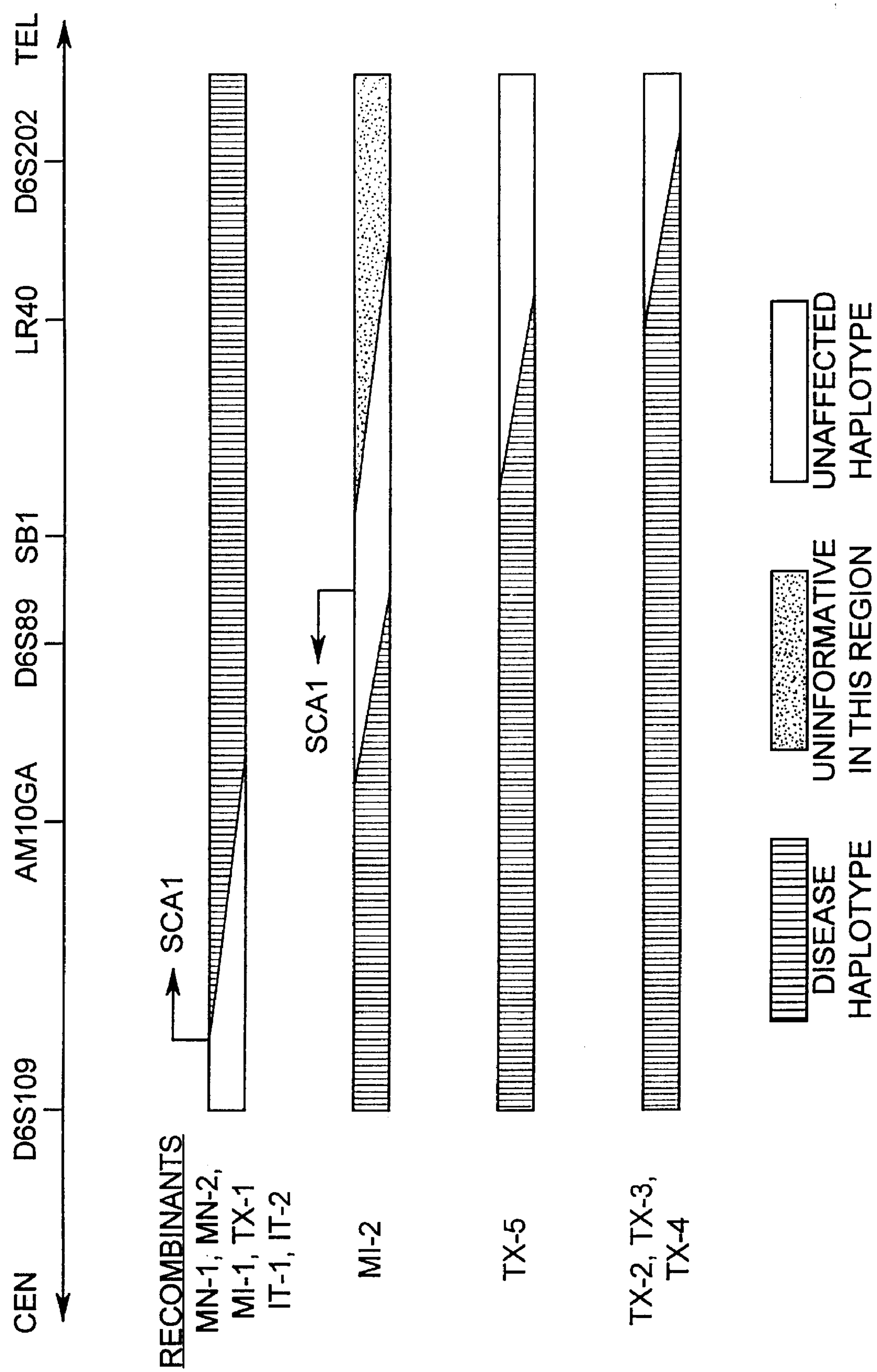
FIG. 4. Summary of SCA1 recombination events that led to the precise mapping of the SCA1 locus. Recombinant disease-carrying chromosomes are shown for the markers shown above. A schematic diagram of the relevant region of 6p22 (not drawn to scale) is shown at the top of the figure. Families are coded as follows: TX=Houston, MN=Minnesota, MI=Michigan, IT=Italy. Each recombination event is given a number following the family code.

Substantial efforts have been made to localize the SCA1 gene using genetic and physical mapping methods. Genetically, SCA1 is flanked on the centromeric side by D6S88 at a rEcombination fraction of approximately 0.08 (based on marker-marker distances using the Centre d'Etude du Polymorphisme Humain (CEPH) reference families) and on the telomeric side by F13A at a recombination fraction of 0. 19. See, L. P. W. Ranum et al., *Am. J. Hum. Genet.,* 49 3 1–41 (1991). Both markers are quite distant and are not practical for use in efforts aimed at cloning the SCA1 gene. The D6S89 marker maps closer to the SCA1 gene.

To localize SCA1 more precisely, five dinucleotide polymorphisms near D6S89 have been identified. A new marker, AM10GA, demonstrates no recombination with SCA1. Linkage analysis and analysis of recombination events confirm that SCA1 maps centromeric to D6S89 with D6S109 as the other flanking marker at the centromeric end and establishes the following order: centromere-D6S109-AM10GA/SCA1-D6S89-LR40-D6S202-telomere. The genetic distance between the two flanking markers D6S109 and D6S89 is about 6.7 cM based on linkage analysis using 40 reference families from the Centre d'Etude du Polymorphisme Humain (CEPH).

A. SCA1 Gene and Method of Diagnosis

The size of the candidate region on the short arm of chromosome 6 containing the SCA1 locus is about 1.2 Mb, and is flanked by D6S274 to the centromeric side and D6S89 to the telomeric side. The SCA1 gene spans 450 kb of genomic DNA and is organized in nine exons (FIG. 15 is representative of the SCA1 gene from a normal individual). The SCA1 transcript (i.e., mRNA or cDNA clone) is about 10.6–11 kb. The gene is transcribed in both normal and affected SCA1 alleles. The structure of the gene is unusual in that it contains seven exons in the 5'-untranslated region, two large exons (2080 bp and 7805 bp) which contain a 2448-bp coding region, and a 7277 bp 3'-untranslated region. The first four non-coding exons undergo extensive alternative splicing in several tissues.

The gene for SCA1 contains a highly polymorphic CAG repeat that is located within a 3.36-kb fragment produced by digestion of the candidate region with the restriction enzyme, EcoRI. The CAG repeat region preferably lies within the coding region and codes for polyglutamine. This region of CAG repeating sequences is unstable and expanded in individuals with SCA1. Southern and PCR analyses of the $(CAG)_n$ repeat demonstrate a correlation between the size of the repeat expansion and the age-at-onset of SCA1 and severity of the disorder. That is, individuals with more repeat units (or longer repeat tracts) tend to have both an early age of onset and a more severe disease coarse. These results demonstrate that SCA1, like fragile X syndrome, myotonic dystrophy, X-linked spinobulbar muscular atrophy, and Huntington disease, displays a mutational mechanism involving expansion of an unstable trinucleotide repeat.

The identification of a trinucleotide repeat expansion associated with SCA1 allows for improved diagnosis of the disease. Thus, in addition to being directed to the gene for SCA1 and the protein encoded thereby, the present invention also relates to methods of diagnosing SCA1. These diagnostic methods can involve any known method for detecting a specific fragment of DNA. These methods can include direct detection of the DNA or indirect through detection of RNA or proteins, for example. For example, Southern or Northern blotting hybridization techniques using labeled probes can be used. Alternatively, PCR techniques can be used with novel primers that amplify the CAG repeating region of the EcoRI fragment. Nucleic acid sequencing can also be used as a direct method of determining the number of CAG repeats.

For example, DNA probes can be used for identifying DNA segments of the affected allele of the SCA1 gene. DNA probes are segments of labeled, single-stranded DNA which will hybridize, or noncovalently bind, with complementary single-stranded DNA derived from the gene sought to be identified. The probe can be labeled with any suitable label known to those skilled in the art, including radioactive and nonradioactive labels. Typical radioactive labels include $^{32}P$, $^{125}I$, $^{35}S$, and the like. Nonradioactive labels include, for example, ligands such as biotin or digoxigenin as well as enzymes such as phosphatase or peroxidases, or the various chemiluminescers such as luciferin, or fluorescent compounds like fluorescein and its derivatives. The probe may also be labeled at both ends with different types of labels for ease of separation, as, for example, by using an isotopic label at one end and a biotin label at the other end.

Using DNA probe analysis, the target DNA can be derived by the enzymatic digestion, fractionation, and denaturation of genomic DNA to yield a complex mixture incorporating the DNA from many different genes, including DNA from the short arm of chromosome 6, which includes the SCA1 locus. A specific DNA gene probe will hybridize only with DNA derived from its target gene or gene fragment, and the resultant complex can be isolated and identified by techniques known in the art.

In general, for detecting the presence of a DNA sequence located within the SCA1 gene, the genomic DNA is digested with a restriction endonuclease to obtain DNA fragments. The source of genomic DNA to be tested can be any biological specimen that contains DNA. Examples include specimen of blood, semen, vaginal swabs, tissue, hair, and body fluids. The restriction endonuclease can be any that will cut the genomic DNA into fragments of double-stranded DNA having a particular nucleotide sequence. The specificities of numerous endonucleases are well known and can be found in a variety of publications, e.g. Maniatis et al.; *Molecular Cloning: A Laboratory Manual;* Cold Spring Harbor Laboratory: New York (1982). That manual is incorporated herein by reference in its entirety. Preferred restriction endonuclease enzymes include EcoRI, TaqI, and BstNI. EcoRI is particularly preferred.

Diagnosis of the disease can alternatively involve the use of the polymerase chain reaction sequence amplification method (PCR) using novel primers. U.S. Pat. No. 4,683,195 (Mullis et al., issued Jul. 28, 1987) describes a process for amplifying, detecting and/or cloning nucleic acid sequences. The method involves treating extracted DNA to form single-stranded complementary strands, treating the separate complementary strands of DNA with two oligonucleotide primers, extending the primers to form complementary extension products that act as templates for synthesizing the desired nucleic acid molecule; and detecting the amplified molecule. More specifically, the method steps of treating the DNA with primers and extending the primers include the steps of: adding a pair of oligonucleotide primers, wherein one primer of the pair is substantially complementary to part of the sequence in the sense strand and the other primer of each pair is substantially complementary to a different part of the same sequence in the complementary antisense strand; annealing the paired primers to the complementary molecule; simultaneously extending the annealed primers from a 340 terminus of each primer to synthesize an extension product complementary to the strands annealed to each primer wherein said extension products after separation from the complement serve as templates for the synthesis of an extension product for the other primer of each pair; and separating said extension products from said templates to produce single-stranded molecules. Variations of the method are described in U.S. Pat. No. 4,683,194 (Saiki et al., issued Jul. 28, 1987). The polymerase chain reaction sequence amplification method is also described by Saiki et al., *Science,* 230, 1350–1354 (1985). The discussion of the these techniques in each of these references is incorporated herein by reference.

The primers are oligonucleotides, either synthetic or naturally occurring, capable of acting as a point of initiating synthesis of a product complementary to the region of the DNA sequence containing the CAG repeating trinucleotides of the SCA1 locus of the short arm of chromosome 6. The primer includes a nucleotide sequence substantially complementary to a portion of a strand of an affected or a normal allele of a fragment (preferably a 3.36 kb EcoRI fragment) of an SCA1 gene having a $(CAG)_n$ region. The primer sequence has at least about 11 nucleotides, preferably at least about 16 nucleotides and no more than about 35 nucleotides. The primers are chosen such that they produce a primed product of about 70–350 base pairs, preferably about 100–300 base pairs. More preferably, the primers are chosen such that nucleotide sequence is substantially complementary to a portion of a strand of an affected or a normal allele within about 150 nucleotides on either side of the $(CAG)_n$ region, including directly adjacent to the $(CAG)_n$ region.

Examples of preferred primers are shown by solid lines with arrowheads in FIG. 3. The primers are thus selected from the group consisting of CCGGAGCCCTGCTGAGGT (CAG-a) (SEQ ID NO:26), CCAGACGCCGGGACAC (CAG-b) (SEQ ID NO:27), AACTGGAAATGTGGACGTAC (Rep-1) (SEQ ID NO:28), CAACATGGGCAGTCTGAG (Rep-2) (SEQ ID NO:29), CCACCACTCCATCCCAGC (GCT-435) (SEQ ID NO:30), TGCTGGGCTGGTGGGGGG (GCT-214) (SEQ ID NO:31), CTCTCGGCTTTCTTGGTG (Pre-1) (SEQ ID NO:32), and GTACGTCCACATTTCCAGTT (Pre-2) (SEQ ID NO:33). These primers can be used in various combinations or with any other primer that can be designed to hybridize to a portion of DNA of a fragment (preferably a 3.36 kb EcoRI fragment) of an SCA1 gene having a CAG repeat region. For example, the primer labeled Rep-2 can be combined with the primer labeled CAG-a, and the primer labeled CAG-b can be combined with the primer labeled Rep-1. More preferably the primers are the sets of primer pairs designed as CAG-a/CAG-b, Rep-1/Rep-2, Rep-1/GCT-435, for example. These primer sets successfully amplify the CAG repeat units of interest using PCR technology. Alternatively, they can be used in various known techniques to sequence the SCA1 gene.

As stated previously, other methods of diagnosis can be used as well. They can be based on the isolation and identification of the repeat region of genomic DNA (CAG repeat region), cDNA (CAG repeat region), mRNA (GUC repeat region), and protein products (glutamine repeat region). These include, for example, using a variety of electrophoresis techniques to detect slight changes in the nucleotide sequence of the SCA1 gene. Further nonlimiting examples include denaturing gradient electrophoresis, single strand conformational polymorphism gels, and nondenaturing gel electrophoresis techniques.

The mapping and cloning of the SCA1 gene allows the definitive diagnosis of one type of the dominantly inherited ataxias using a simple blood test. This represents the first step towards an unequivocal molecular classification of the dominant ataxias. A simple and reliable classification system for the ataxias is important because the clinical symptoms overlap extensively between the SCA1 and the non-SCA1 forms of the disease. Furthermore, a molecular test for the only known SCA1 mutation permits presymptomatic diagnosis of disease in known SCA1 families and allows for the identification of sporadic or isolated CAG repeat expansions where there is no family history of the disease. Thus, the present invention can be used in family counseling, planning medical treatment, and in standard work-ups of patients with ataxia of unknown etiology.

B. Cloning

Cloning of SCA1 DNA into the appropriate replicable vectors allows expression of the gene product, ataxin-1, and makes the SCA1 gene available for further genetic engineering. Expression of ataxin-1 or portions thereof, is useful because these gene products can be used as antigens to produce antibodies, as described in more detail below.

1. Isolation of DNA

DNA containing thc SCA1 gene may be obtained from any cDNA library prepared from tissue believed to possess the SCA1 mRNA and to express it at a detectable level. Preferably, the cDNA library is from human fetal brain or adult cerebellum. Optionally, the SCA1 gene may be obtained from a genomic DNA library or by in vitro oligonucleotide synthesis from the complete nucleotide or amino acid sequence.

Libraries are screened with appropriate probes designed to identify the gene of interest or the protein encoded by it. Preferably, for cDNA libraries, suitable probes include oligonucleotides that consist of known or suspected portions of the SCA1 cDNA from the same or different species; and/or complementary or homologous cDNAs or fragments thereof that consist of the same or a similar gene. Optionally, for cDNA expression libraries (which express the protein), suitable probes include monoclonal or polyclonal antibodies that recognize and specifically bind to the SCA1 gene product, ataxin-1. Appropriate probes for screening genomic DNA libraries include, but are not limited to, oligonucleotides, cDNAs, or fragments thereof that consist of the same or a similar gene, and/or homologous genomic DNAs or fragments thereof. Screening the cDNA or genomic library with the selected probe may be accomplished using standard procedures.

Screening cDNA libraries using synthetic oligonucleotides as probes is a preferred method of practicing this invention. The oligonucleotide sequences selected as probes should be of sufficient length and sufficiently unambiguous to minimize false positives. The actual nucleotide sequence (s) of the probe(s) is usually designed based on regions of the SCA1 gene that have the least codon redundancy. The oligonucleotides may be degenerate at one or more positions, i.e., two or more different nucleotides may be incorporated into an oligonueleotide at a given position, resulting in multiple synthetic oligonucleotides. The use of degenerate oligonucleotides is of particular importance where a library is screened from a species in which preferential codon usage is not known.

The oligonucleotide can be labeled such that it can be detected upon hybridization to DNA in the library being screened. A preferred method of labeling is to use ATP and polynucleotide kinase to radiolabel the 5' end of the oligonucleotide. However, other methods may be used to label the oligonucleotide, including, but not limited to, biotinylation or enzyme labeling.

Of particular interest is the SCA1 nucleic acid that encodes a full-length mRNA transcript, including the complete coding region for the gene product, ataxin-1. Nucleic acid containing the complete coding region can be obtained by screening selected cDNA libraries using the deduced amino acid sequence.

An alternative means to isolate the SCA1 gene is to use PCR methodology. This method requires the use of oligonucleotide primer probes that will hybridize to the SCA1 gene. Strategies for selection of PCR primer oligonucleotides are described below.

2. Insertion of DNA into Vector

The nucleic acid (e.g., cDNA or genomic DNA) containing the SCA1 gene is preferably inserted into a replicable vector for further cloning (amplification of the DNA) or for expression of the gene product, ataxin-1. Many vectors are available, and selection of the appropriate vector will depend on: 1) whether it is to be used for DNA amplification or for DNA expression; 2) the size of the nucleic acid to be inserted into the vector; and 3) the host cell to be transformed with the vector. Most expression vectors are "shuttle" vectors, i.e., they are capable of replication in at least one class of organism but can be transfected into another organism for expression. For example, a vector is cloned in *E. coli* and then the same vector is transfected into yeast or mammalian cells for expression even though it is not capable of replicating independently of the host cell chromosome. Each replicable vector contains various structural components depending on its function (amplification of DNA or expression of DNA) and the host cell with which it is compatible. These components are described in detail below.

Construction of suitable vectors employs standard ligation techniques known in the art. Isolated plasmids or DNA fragments are cleaved, tailored, and religated in the form desired to generate the plasmids required. Typically, the ligation mixtures are used to transform *E. coli* K12 strain 294 (ATCC 31,446) and successful transformants are selected by ampicillin or tetracycline resistance where appropriate. Plasmids from the transformants are prepared, analyzed by restriction endonuclease digestion, and/or sequenced by methods known in the art. See e.g., Messing et al., *Nucl. Acids Res.,* 9, 309 (1981) and Maxam et al., *Methods in Enzymology,* 65, 499 (1980).

Optionally, DNA may also be amplified by direct insertion into the host genome. This is readily accomplished using Bacillus species as hosts, for example, by including in the vector a DNA sequence that is complementary to a sequence found in Bacillus genomic DNA. Transfection of Bacillus with this vector results in homologous recombination with the genome and insertion of SCA1 DNA. However, the recovery of genomic DNA containing the SCA1 gene is more complex than that of an exogenously replicated vector because restriction enzyme digestion is required to excise the SCA1 DNA.

Replicable cloning and expression vector components generally include, but are not limited to, one or more of the following: a signal sequence, an origin of replication, one or more marker genes, an enhancer element, a promoter and a transcription termination sequence.

Vector component: signal sequence. A signal sequence may be used to facilitate extracellular transport of a cloned protein. To this end, the SCA1 gene product, ataxin-1, may be expressed not only directly, but also as a fusion product with a heterologous polypeptide, preferably a signal sequence or other polypeptide having a specific cleavage site at the N-terminus of the cloned protein or polypeptide. The signal sequence may be a component of the vector, or it may be a part of the SCA1 DNA that is inserted into the vector. The heterologous signal sequence selected should be one that is recognized and processed (i.e., cleaved by a signal peptidase) by the host cell. For prokaryotic host cells, a prokaryotic signal sequence may be selected, for example, from the group of the alkaline phosphatase, penicillinase, 1 pp or heat-stable intertoxin II leaders. For yeast secretion the signal sequence used may be, for example, the yeast invertase, alpha factor, or acid phosphatase leaders. In mammalian cell expression, a native signal sequence may be satisfactory, although other mammalian signal sequences may be suitable such as signal sequences from secreted polypeptides of the same or related species, as well as viral secretory leaders, for example, the herpes simplex gD signal.

Vector component: origin of replication. Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast and viruses. The origin of replication from the plasmid pBR322 is suitable for most Gram-negative bacteria, the 2 m plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Vector component: marker gene. Expression and cloning vectors 10 may contain a marker gene, also termed a selection gene or selectable marker. This gene encodes a protein necessary for the survival or growth of transformed host cells grown in a selective culture medium. Host cells not transformed with the vector containing the selection gene will not survive in the culture medium. Typical selection genes encode proteins that: (a) confer resistance to antibiotics or other toxins, e.g., ampicillin, neomycin, methotrexate, streptomycin or tetracycline; (b) complement auxotrophic deficiencies; or (c) supply critical nutrients not available from complex media, e.g., the gene encoding D-alanine racemase for Bacilli. One example of a selection scheme utilizes a drug to arrest growth of a host cell. Those cells that are successfully transformed with a heterologous gene express a protein conferring drug resistance and thus survive the selection regimen.

An example of suitable selectable markers for mammalian cells are those that enable the identification of cells competent to take up the SCA1 nucleic acid, such as dihydrofolate reductase (DHFR) or thymidine kinase. The mammalian cell transformants are placed under selection pressure that only transformants are uniquely adapted to survive by virtue of having taken up the marker. For example, cells transformed with the DHFR selection gene are first identified by culturing all the transformants in a culture medium that contains methotrexate, a competitive antagonist for DHFR. An appropriate host cell when wild-type DHFR is employed is the Chinese hamster ovary (CHO) cell line deficient in DHFR activity, prepared and propagated as described by Urlaub et al., *Proc. Natl. Acad. Sci. USA,* 77, 4216 (1980). The transformed cells are then exposed to increased levels of methotrexate.

This leads to the synthesis of multiple copies of the DHFR gene, and, concomitantly, multiple copies of the other DNA comprising the expression vectors, such as the SCA1 gene. This amplification technique can be used with any otherwise suitable host, e.g., ATCC No. CCL61 CHO-K1, notwithstanding the presence of endogenous DHFR if, for example, a mutant DHFR gene that is highly resistant to methotrexate is employed. Alternatively, host cells (particularly wild-type hosts that contain endogenous DHFR) transformed or co-transformed with SCA1 DNA, wild-type DHFR protein, and another selectable marker such as aminoglycoside 3' phosphotransferase (APH) can be selected by cell growth in a medium containing a selection agent for the selectable marker such as an aminoglycosidic antibiotic, e.g., kanamycin or neomycin. A suitable selection gene for use in yeast is the trp1 gene present in the yeast plasmid YRp7 (Stinchcomb et al., *Nature,* 282, 39 (1979); Kingsman et al., *Gene,* 7, 141 (1979); or Tschumper et al., *Gene,* 10, 157 (1980)). The trpl gene provides a selection marker for a mutant strain of yeast lacking the ability to grow in tryptophan, for example, ATCC NO. 44076 or PEP4-1 (Jones, *Genetics,* 85, 23–33 (1977)). The presence of the trp1 lesion in the yeast host cell genome then provides an effective environment for detecting transformation by growth in the absence of tryptophan. Similarly, Leu2 deficient yeast strains (ATCC 20,622 or 38,626) are complemented by known plasmids bearing the Leu2 gene.

Vector component: promoter. Expression and cloning vectors usually contain a promoter that is recognized by the host organism and is operably linked to the SCA1 nucleic acid. Promoters are untranslated sequences located upstream (5') to the start codon of a structural gene (generally within about 100 to 1000 bp) that control the transcription and translation of a particular nucleic acid sequence, such as the ataxin-1 nucleic acid sequence, to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. In contrast, constitutive promoters produce a constant level of transcription of the cloned DNA segment.

At this time a large number of promoters recognized by a variety of potential host cells are well known in the art. Promoters are removed from their source DNA using a restriction enzyme digestion and inserted into the cloning vector using standard molecular biology techniques. Both the native SCA1 promoter sequence and many heterologous promoters can be used to direct amplification and/or expression of the SCA1 DNA. Heterologous promoters are preferred, as they generally permit greater transcription and higher yields of expressed protein as compared to the native promoter. Well-known promoters suitable for use with prokaryotic hosts include the beta-lactamase and lactose promoter systems, alkaline phosphatase, a tryptophan (trp) promoter system, and hybrid promoters such as the tac promoter. Such promoters can be ligated to SCA1 DNA using linkers or adapters to supply any required restriction sites. Promoters for use in bacterial systems may contain a Shine-Dalgarno sequence for RNA polymerase binding.

Promoter sequences are known for eukaryotes. Virtually all eukaryotic genes have an AT-rich region located approximately 25 to 30 bp upstream from the site where transcription is initiated Another sequence found 70 to 80 bases upstream from the start of transcription of many genes is the CXCAAT region where X may be any nucleotide. At the 3' end of most eukaryotic genes is an AATAAA sequence that may be a signal for addition of the poly A tail to the 3' end of the coding sequence. All these sequences are suitably inserted into eukaryotic expression vectors. Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase and glucokinase. Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3 -phosphate dehydrogenase, and enzymes responsible for maltose and galactose utilization.

SCA1 transcription from vectors in mammalian host cells can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, Hepatitis-B virus and most preferably Simian Virus 40 (SV40) (Fiers et al., *Nature,* 273, 113 (1978); Mulligan et al., *Science,* 209, 1422–1427 (1980); Pavlakis et al., *Proc. Natl., Acad. Sci. USA,* 78, 7398–7402 (1981)). Heterologous mammalian promoters (e.g., the actin promoter or an immunoglobulin promoter) and heat-shock promoters can also be used, as can the promoter normally associated with the SCA1 sequence itself, provided such promoters are compatible with the host cell systems.

Vector component: enhancer element. Transcription of SCA1 DNA by higher eukaryotes can be increased by inserting an enhancer sequence into the vector. Enhancers are cis-acting elements of DNA, usually having about 10 to 300 bp, that act on a promoter to increase its transcription. Enhancers are relatively orientation- and position-independent, having been found 5' and 3' to the transcription unit, within an intron as well as within the coding sequence itself. Many enhancer sequences are now known from mammalian genes (globin, elastase, albumin, alpha-fetoprotein, and insulin). Typically, however, an enhancer from a eukaryotic cell virus will be used. Examples include the SV40 enhancer on the late side of the replication origin, the cytomegalovirus early promoter enhancer, the polyoma enhancer on the late side of the replication origin, and adenovirus enhancers. The enhancer may be spliced into the vector at a position 5' or 3' to the SCA1 gene, but is preferably located at a site 5' of the promoter.

Vector component: transcription termination. Expression vectors used in eukaryotic host cells (yeast, fungi, insect, plant, animal, human or nucleated cells from other multicellular organisms) can also contain sequences necessary for the termination of transcription and for stabilizing the mRNA. Such sequences are commonly available from the 5' and, occasionally, 3' untranslated regions of eukaryotic or viral DNAs or cDNAs. These regions can contain nucleotide segments transcribed as polyadenylated fragments in the untranslated portion of mRNA encoding ataxin-1.

Preferably, the pMAL™-2 vectors (New England Biolabs, Beverly, Mass.) are used to create the expression vector. These vectors provide a convenient method for expressing and purifying ataxin-1 produced from the cloned SCA1 gene. The SCA1 gene is inserted downstream from the malE gene of *E. coli*, which encodes maltose-binding protein (MBP) resulting in the expression of an MBP fusion protein. The method uses the strong "tac" promoter and the malE translation initiation signals to give high-level expression of the cloned sequences, and a one-step purification of the fusion protein using MBP's affinity for maltose. The vectors express the malE gene (with or without its signal sequence) fused to the lacZα gene. Restriction sites between malE and lacZα are available for inserting the coding sequence of interest. Insertion inactivates the β-galactosidase α-fragment activity of the malE-lacZα fusion, which results in a blue to white color change on Xgal plates when the construction is transformed into an α-complementing host such as TB1 (T. C. Johnston et al., *J. Biol. Chem.,* 261, 4805–4811 (1986)) or JM107 (C. Yanisch-Perron et al., *Gene,* 33, 103–119 (1985)). When present, the signal peptide on pre-MBP directs fusion proteins to the periplasm. For fusion proteins that can be successfully exported, this allows folding and disulfide bond formation to take place in the periplasm of *E Coli*, as well as allowing purification of the protein from the periplasm. The vectors carry the $lac^q$ gene, which codes for the Lac repressor protein. This keeps expression from $P_{lac}$ low in the absence of isopropyl β-D-thiogalactopyranoside (IPTG) induction. The pMAL™-2 vectors also contain the sequence coding for the recognition site of the specific protease factor Xa, located just 5' to the polylinker insertion sites. This allows MBP to be cleaved from ataxin-1 after purification. Factor Xa cleaves after its four amino acid recognition sequence, so that few or no vector derived residues are attached to the protein of interest, depending on the site used for cloning.

Also useful are expression vectors that provide for transient expression in mammalian cells of SCA1 DNA. In general, transient expression involves the use of an expression vector that is able to replicate efficiently in a host cell, such that the host cell accumulates many copies of the expression vector and, in turn, synthesizes high levels of a desired polypeptide encoded by the expression vector. Transient expression systems, comprising a suitable expression vector and a host cell, allow for the convenient positive identification of polypeptides encoded by cloned DNAs, as well as for the rapid screening of such polypeptides for desired biological or physiological properties. Thus, transient expression systems are particularly useful in the invention for purposes of identifying analogs and variants of ataxin-1 that have wild-type or variant biological activity.

3. Host Cells

Suitable host cells for cloning or expressing the vectors herein are the prokaryote, yeast, or higher eukaryotic cells described above. Suitable prokaryotes include eubacteria, such as Gram-negative or Gram-positive organisms, for example, *E. coli*, Bacilli such as *B. sublilis,* Pseudomonas species such as *P. aeruginosa, Salmonella typhimurium*, or *Serratia marcsecans*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting. Preferably the host cell should secrete minimal amounts of proteolytic enzymes. Alternatively, in vitro methods of cloning, e.g., PCR or other nucleic acid polymerase reactions, are suitable.

In addition to prokaryotes, eukaryotic microbes such as filamentous fungi or yeast are suitable hosts for SCA1-encoding vectors. *Saccaromyces cerevisiae*, or common baker's yeast, is the most commonly used among lower eukaryotic host microorganisms. However, a number of other genera, species, and strains are commonly available and useful herein, such as *Schizosaccaromyces pombe,* Kluyveromyces hosts such as, e.g., *K lactis, K fragilis, K bulgaricus, K thermotolerans,* and *K marxianus, yarrowia, Pichia pastoris,* Candida, *Trichoderma reesia, Neurospora crassa,* and filamentous fungi such as, e.g., *Neurospora, Penicillium,* Tolypocladium, and *Aspergillus* hosts such as *A. nidulans.*

Suitable host cells for the expression of glycosylated ataxin-1 are derived from multicellular organisms. Such host cells are capable of complex processing and glycosylation activities. In principle, any higher eukaryotic cell culture is workable, whether from vertebrate or invertebrate culture. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. See, e.g., Luckow et al., *Bio/Technology,* 6, 47–55 (1988); Miller et al., *Genetic Engineering,* 8, 277–279 (1986); and Maeda et al., *Nature,* 315, 592–594 (1985). A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoplera frugiperda* cells.

Plant cell cultures of cotton, corn, potato, soybean, petunia, tomato, and tobacco can be utilized as hosts. Typically, plant cells are transfected by incubation with certain strains of the bacterium *Agrobacterium tumefaciens*, which has been previously manipulated to contain the SCA1 DNA. During incubation of the plant cell culture with *A. tumefaciens*, the SCA1 DNA is transferred to the plant cell host such that it is transfected, and will, under appropriate conditions, express the SCA1 DNA. In addition, regulatory and signal sequences compatible with plant cells are available, such as the nopaline synthase promoter and polyadenylation signal sequences. Depicker et al., *J. Mol. Appl. Gen.,* 1, 561 (1982).

Vertebrate cells can also be used as hosts. Propagation of vertebrate cells in culture (tissue culture) has become a routine procedure in recent years. Examples of useful mammalian host cell lines are monkey kidney CV1 line transformed by SV40 (CAS-7, ATCC CRL 1651); human embryonic kidney line (293 or 293 cells subcloned for growth in suspension culture, Graham et al., *J. Gen. Virol.,* 36, 59 (1977)); baby hamster kidney cells (BHK, ATCC CCL 10); Chinese hamster ovary cells/-DHFR (CHO, Urlaub and Chasin, *Proc. Natl. Acad. Sci. USA,* 77, 4216 (1980)); mouse sertoli cells (TM4, Mather, *Biol Reprod.,* 23, 243–251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL 51); TRI cells (Mather et al., *Annals N.Y. Acad. Sci.,* 383, 44–68 (1982)); MRC 5 cells; FS4 cells; and a human hepatoma line (Hep G2).

4. Transfection and transformation

Host cells are transfected and preferably transformed with the above-described expression or cloning vectors of this invention and cultured in conventional nutrient media modified as appropriate for inducing promoters, selecting transformants, or amplifying the genes encoding the desired sequences.

Transfection refers to the taking up of an expression vector by a host cell whether or not any coding sequence arc in fact expressed. Numerous methods of transfection are known to the ordinarily skilled artisan, for example, the calcium phosphate precipitation method and electroporation are commonly used. Successful transfection is generally recognized when any indication of the operation of the vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. Calcium chloride is generally used for prokaryotes or other cells that contain substantial cell-wall barriers. Infection with *Agrobacterium tumefaciens* can be used for transformation of certain plant cells. For mammalian cells without cell walls, the calcium phosphate precipitation method of Graham et al., *Virology,* 52, 456–457 (1978) is preferred. Transformations into yeast are typically carried out according to the method of Van Solingen et al., *J. Bact.,* 130, 946 (1977) and Hsiao et al., *Proc. Natl. Acad. Sci. (USA),* 78 3829 (1979). However, other methods for introducing DNA into cells such as by nuclear injection, electroporation, or protoplast fusion may also be used.

5. Cell Culture

Prokaryotic cells used to produce the SCA1 gene product, ataxin-1, are cultured in suitable media, as described generally in Sambrook et al. The mammalian host cells used to produce the SCA1 gene product may be cultured in a variety of media. Commercially available media such as Hams F10 (Sigma), Minimal Essential Medium (MEM, Sigma), RPMI-1640 (Sigma), and Dulbecco's Modified Eagle's Medium (DMEM, Sigma) are suitable for culturing the host cells. These media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan. The host cells referred to in this disclosure encompass in in vitro culture as well as cells that are within a host animal.

C. Protein

The SCA1 gene encodes a novel protein, ataxin-1, a representative example of which is shown in FIG. 15 with an estimated molecular weight of about 87 kD. It is to be understood that ataxin-1 represents a set of proteins produced from the SCA1 gene with its unstable CAG region. Ataxin-1 can be produced from cell cultures. With the aid of recombinant DNA techniques, synthetic DNA and cDNA coding for ataxin-1 can be introduced into microorganisms which can then be made to produce the peptide. It is also possible to manufacture ataxin-1 synthetically, in a manner such as is known for peptide syntheses.

Ataxin-1 is preferably recovered from the culture medium as a cytosolic polypeptide, although it can also be recovered as a secreted polypeptide when expressed with a secretory signal.

Ataxin-1 can be purified from recombinant cell proteins or polypeptides to obtain preparations that are substantially homogenous as ataxin-1. As a first step, the culture medium or lysate is centrifuged to remove particulate cell debris. The membrane and soluble protein fractions are then separated. The ataxin-1 may then be purified from the soluble protein fraction and from the membrane fraction of the culture lysate, depending on whether the ataxin-1 is membrane bound. If necessary, ataxin-1 is further purified from contaminant soluble proteins and polypeptides, with the following procedures being exemplary of suitable purification procedures: by fractionation on immunoaffinity or ion-exchange columns; ethanol precipitation; reverse phase HPLC; chromatography on silica or on a cation-exchange resin such as DEAE; chromatofocusing; SDS-PAGE; ammonium 20 sulfate precipitation; gel filtration using, for example, Sephadex G-75; ligand affinity chromatography, using, e.g., protein A Sepharose columns to remove contaminants such as IgG.

Ataxin-1 variants in which residues have been deleted, inserted, or substituted are recovered in the same fashion as native ataxin-1, taking account of any substantial changes in properties occasioned by the variation. For example, preparation of an ataxin-1 fusion with another protein or polypeptide, e.g., a bacterial or viral antigen, facilitates purification; an immunoaffinity column containing antibody to the antigen can be used to adsorb the fusion polypeptide. Immunoaffinity columns such as a rabbit polyclonal ataxin-1 column can be employed to absorb the ataxin-1 variant by binding it to at least one remaining immune epitope. Alternatively, the ataxin-1 may be purified by affinity chromatography using a purified ataxin-1-IgG coupled to a (preferably) immobilized resin such as Affi-Gel 10 (Bio-Rad, Richmond, Calif.) or the like, by means well-known in the art. A protease inhibitor such as phenyl methyl sulfonyl fluoride (PMSF) also may be useful to inhibit proteolytic degradation during purification, and antibiotics may be included to prevent the growth of adventitious contaminants.

Covalent modifications of ataxin-1 are included within the scope of this invention. Both native ataxin-1 and amino acid sequence variants of the ataxin-1 may be covalently modified. Covalent modifications included within the scope of this invention are those producing one or more ataxin-1 fragments. Ataxin-1 fragments having any number of amino acid residues may be conveniently prepared by chemical synthesis, by enzymatic or chemical cleavage of the full-length or variant ataxin-1 polypeptide, or by cloning and expressing only portions of the SCA1 gene. Other types of covalent modifications of ataxin-1 or fragments thereof are introduced into the molecule by reacting targeted amino acid residues of the ataxin-1 or fragments thereof with a derivatizing agent capable of reacting with selected side chains or the N- or C-terminal residues.

For example, cysteinyl residues most commonly are reacted with αhaloacetates (and corresponding amines), such as iodoacetic acid or iodoacetamide, to give carboxymethyl or carboxyamidomethyl derivatives. Cysteinyl residues also are derivatized by reaction with bromotrifluoroacetone, α-bromo-β-(5-imidozoyl) propionic acid, iodoacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate p-bromophenacyl. Lysinyl and amino terminal residues are derivatized with succinic or other carboxylic acid anhydrides and imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate. Arginyl residues are modified by reaction with phenylglyoxal, 2,3-butanedione, 1,2-cyclohexanedione, and ninhydrin, among others.

Specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepared labeled proteins for use in radioimmunoassay, the chloramine T method described above being suitable.

Carboxyl side groups (aspartyl or glutamyl) are selectively modified by reaction with carbodiimides (R—N═C═N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking ataxin-1 to a water-insoluble support matrix or surface for use in the method for purifying anti-ataxin-1 antibodies, and vice versa. Commonly used crosslinking agents include, e.g., 1,1-bis(diazoacetyl)-2-phenylethane, glutaraldehyde, and N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio] propiomidate yield photoactivatable intermediates that arc capable of forming crosslinks in the presence of light. Alternatively, reactive water-insoluble matrices such as cyanogen bromide-activated carbohydrates and the reactive substrates are employed for protein immobilization.

Glutaminyl and asparaginyl residues are frequently deamidated to the corresponding glutamyl and aspartyl residues, respectively. These residues are deamidated under neutral or basic conditions. The deamidated form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains, acetylation of the N-terminal amine, amidation of any C-terminal carboxyl group, and glycosylation of any suitable residue.

D. Antibodies

The present invention also relates to polyclonal or monoclonal antibodies raised against ataxin-1 or ataxin-1 fragments (preferably fragments having 8–40 amino acids, more preferably 10–20 amino acids, that form the surface of the folded protein), or variants thereof, and to diagnostic methods based on the use of such antibodies, including but not limited to Western blotting and ELISA (enzyme-linked immunosorbant assay).

Polyclonal antibodies to the SCA1 polypeptide generally are raised in animals by multiple subcutaneous (sc) or intraperitoneal (ip) injections of ataxin-1, ataxin-1 fragments, or variants thereof, and an adjuvant. The polypeptide can be a cloned gene product or a synthetic molecule. Preferably, it corresponds to a position in the protein sequence that is on the surface of the folded protein and is thus likely to be antigenic. It may be useful to conjugate the SCA1 polypeptide (including fragments containing a specific amino acid sequence) to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehye, succinic anhydride, $SOC1_2$, or $R^1N{=}C{=}NR$, where R and $R^1$ are different alkyl groups. Conjugates also can be made in recombinant cell culture as protein fusions. Also, aggregating agents such as alum are used to enhance the immune response.

The route and schedule of immunizing a host animal or removing and culturing antibody-producing cells are variable and are generally in keeping with established and conventional techniques for antibody stimulation and production. While mice are frequently employed as the host animal, it is contemplated that any mammalian subject including human subjects or antibody-producing cells obtained therefrom can be manipulated according to the processes of this invention to serve as the basis for production of mammalian, including human, hybrid cell lines. Preferably, rabbits are used to raise antibodies against ataxin-1.

Animals are typically immunized against the immunogenic conjugates or derivatives by combining about 10 μg to about 1 mg of ataxin-1 with about 2–3 volumes of Freund's complete adjuvant and injecting the solution intradermally at multiple sites. About one month later the animals are boosted with bout 1/5 to about 1/10 the original amount of conjugate in Freund's complete adjuvant (or other suitable adjuvant) by subcutaneous injection at multiple sites. about 7 to 14 days later animals are bled and the serum is assayed for anti-ataxin-1 polypeptide titer.

Serum antibodies (IgG) are purified via protein purification protocols that are well known in the art. Antibody/antigen reactivity is analyzed using Western blotting, wherein suspected antigens are blotted to a nitrocellulose filter, exposed to potential antibodies and allowed to hybridize under defined conditions. See Gershoni et al., *Anal. Biochem.,* 131, 1–15 (1983). The protein antigens can then be sequenced using standard sequencing methods directly from the antibody/antigen complexes on the nitrocellulose support.

Monoclonal antibodies are prepared by recovering immune cells-typically spleen cells or lymphocytes from lymph node tissue-from immunized animals (usually mice) and immortalizing the cells in conventional fashion, e.g., by fusion with myeloma cells. The hybridoma technique described originally by Kohler et al., *Eur. J. Immunol.,* 6, 511 (1976) has been widely applied to produce hybrid cell lines that secrete high levels of monoclonal antibodies against many specific antigens. It is possible to fuse cells of one species with another. However, it is preferable that the source of the immunized antibody-producing cells and the myeloma be from the same species. While mouse monoclonal antibodies are routinely used, the present invention is not so limited. In fact, although mouse monoclonal antibodies are typically used, human antibodies may be used and may prove to be preferable. Such antibodies can be obtained by using human hybridomas. Cote et al.; *Monoclonal Antibodies and Cancer Therapy*; A. R. Liss, Ed.; p. 77 (1985).

The secreted antibody is recovered from tissue culture supernatant by conventional methods such as precipitation, ion exchange chromatography, affinity chromatography, or the like. The antibodies described herein are also recovered from hybridoma cell cultures by conventional methods for purification of IgG or IgM, as the case may be, that heretofore have been used to purify these immunoglobulins from pooled plasma, e.g., ethanol or polyethylene glycol precipitation procedures. The purified antibodies are sterile filtered, and optionally are conjugated to a detectable marker such as an enzyme or spin label for use in diagnostic assays of the ataxin-1 in test samples.

Techniques for creating recombinant DNA versions of the antigen-binding regions of antibody molecules (known as Fab fragments), which bypass the generation of monoclonal antibodies, are encompassed within the practice of this invention. Antibody-specific messenger RNA molecules are extracted from immune system cells taken from an immunized animal, transcribed into complementary DNA (cDNA), and the cDNA is cloned into a bacterial expression system.

The anti-ataxin-1 antibody preparations of the present invention are specific to ataxin-1 and do not react immunochemically with other substances in a manner that would interfere with a given use. For example, they can be used to screen for the presence of ataxin-1 in tissue extracts to determine tissue-specific expression levels of ataxin-.

The present invention also encompasses an immunochemical assay that involves subjecting antibodies directed against ataxin-1 to reaction with the ataxin-1 present in a sample to thus form an (ataxin-1anti-ataxin-1) immune complex, the formation and amount of which are measures-qualitative and quantitative, respectively-of the ataxin-1 presence in the sample. The addition of other reagents capable of biospecifically reacting with constituents of the protein/antibody complex, such as anti-antibodies provided with analytically detectable groups, facilitates detection and quantification of ataxin-1 in biological samples, and is especially useful for quantitating the level of ataxin-1 in biological samples. Ataxin-1 anti-ataxin-1 complexes can also be subjected to amino acid sequencing using methods well known in the art to determine the length of a polyglutamine region and thereby provide information about likelihood of affliction with spinocerebellar ataxia and likely age of onset. Competitive inhibition and non-competitive methods, precipitation methods, heterogeneous and homogeneous methods, various methods named according to the analytically detectable group employed, immunoelectrophoresis, particle agglutination, immunodiffusion and immunohistochemical methods employing labeled antibodies may all be used in connection with the immune assay described above.

The invention has been described with reference to various specific and preferred embodiments and will be further described by reference to the following detailed examples. It is understood, however, that there are many extensions, variations, and modifications on the basic theme of the present invention beyond that shown in the examples and detailed description, which are within the spirit and scope of the present invention.

EXPERIMENTAL SECTION

I. The Gene for SCA1 Maps Centromeric to D6S89

To confirm the position of SCA1 with respect to D6S89 and to identify closer flanking markers, two dinucleotide repeat polymorphisms D6S109 and D6S202 were used. Using YAC clones isolated in the D6S89 region, three additional dinucleotide repeat polymorphisms were identified, one of which (AM10GA) showed no recombination with SCA1 and confirmed that D6S89 is telomeric to SCA1. The dinucleotide repeat at D6S109 revealed six recombination events with SCA1 and determined D6S109 to be the other flanking marker at the centromeric end. Linkage analysis, physical mapping data as discussed below, and analysis of recombination events demonstrated that the order of markers is as follows: Centomere-D6S109-AM10GA/SCA1-D6S89-SB1-LR40-D6S202-Telomere.

A. Materials and Methods

1. SCA1 Kindreds

Nine large SCA1 families were used in the present study. Clinical findings and linkage data demonstrating that these families segregated SCA1 have been previously reported. See, J. F. Jackson et al., *N. Engl. J. Med.,* 296, 1138–1141 (1977); B. J. B. Keats et al., *Am. J. Hum. Genet.,* 49, 972–977 (1991); L. P. W. Ranum et al., *Am. J. Hum. Genet.,* 49, 31–41 (1991); and H. Y. Zoghbi et al., *Am. J. Hum. Genet.,* 49, 23–30 (1991). Analysis of polymorphisms at the loci D6S109, AM10GA, SB1, LR40, and D6S202 was performed on individuals from these kindreds.

The Houston (TX-SCA1) kindred included 106 individuals, of whom 57 (25 affected) were genotyped. See, H. Y. Zoghbi et al., *Ann. Neurol.,* 23, 580–584 (1988). Patients symptomatic at the time of exam, as well as asymptomatic individuals who had both a symptomatic child and a symptomatic parent, were classified as "affected." In this kindred, a deceased individual previously assigned as affected (from family history data) was reassigned an unknown status after review of medical records. This reassignment eliminated what was previously thought to be a recombination event between SCA1 and D6S89 in the TX-SCA1 kindred. To maximize the amount of information available for linkage analysis, the two chromosomes 6 in somatic cell hybrids for 15 affected individuals and one unaffected individual from the TX-SCA1 kindred were separated. See, H. Y. Zoghbi et al., *Am. J. Hum. Genet.,* 44, 255–263 (1989). The Louisiana (LA-SCA1) kindred included 50 individuals of whom 26 (8 affected) were genotyped. See, B. J. B. Keats et al., *Am. J. Hum. Genet.,* 49, 972–977 (1991). The Minnesota (MN-SCA1) kindred included 175 individuals, of whom 106 (17 affected) were genotyped. See, J. L. Haines et al., *Neurology,* 34, 1542–1548 (1984); and L. P. W. Ranum et al., *Am. J. Hum. Genet.,* 49, 31–41 (1991). The Michigan (MI-SCA1) kindred included 201 individuals, of whom 127 (25 affected) were genotyped. See, H. E. Nino et al., *Neurology,* 30, 12–20 (1980). The Mississippi (MS-SCA1) kindred included 84 individuals, of whom 37 (17 affected) were genotyped. See, J. F. Jackson et al., *N. Engl. J. Med.,* 296, 1138–1141 (1977).

Four Italian families segregating SCA1 were analyzed; their clinical phenotype and HLA linkage data were reported previously. See, M. Spadaro et al., *Acta Neurol. Scand.,* 85, 257–265 (1992). Three families originated in the Calabria Region (Southern Italy): family IT-P with 135 members of whom 80 (21 affected) were genotyped; for computational reasons, the family was subdivided into 3 different pedigrees (RM, VI, and FB) and only one of the 3 consanguinity loops was considered; family IT-NS, with 43 members of whom 27 (7 affected) were typed; family IT-NS with 51 members of whom 16 (3 affected) were typed. The fourth family, IT-MR, originated from Latium and consisted of 17 individuals of whom 10 (4 affected) were genotyped.

2. CEPH Families

The 40 CEPH reference families were genotyped at the D9S109, LR40 and D6S202 loci in order to provide a large number of informative meioses for marker-marker linkage analyses. Markers AM10GA and SB1 flank D6S89, having been isolated from a yeast artificial chromosome (YAC) contig built bidirectionally from D6S89 (see below). A subset of 18 CEPH families which defined 26 recombinants between D6S109 and D6S89 was genotyped at AM10GA and SB1 in order to determine the order of AM10GA, D6S89 and SB1 with respect to D6S109.

3. Cloning of Sequences Containing Dinucleotide Repeats

The identification and description of polymorphic dinucleotide repeats at the D6S109 and D6S202 loci have been previously reported. See, L. P. W. Ranum et al., *Nucleic Acids Res.,* 19, 1171 (1991); and F. LeBorgne-Demarquoy et al., *Nucleic Acids Res.,* 19, 6060 (1991).

DNA fragments containing dinucleotide repeats were cloned at LR40 and SB1 from yeast artificial chromosome (YAC) clones at the LR40 and FLB1 loci, respectively (see below). DNA from each YAC clone was amplified in a 50 $\mu l$ reaction containing 20 ng DNA, a single Alu primer (see below), 50 mM KC1, 10 mM Tris-C1 pH 8.3, 1.25 mM $MgC1_2$, 200 or 250 $\mu M$ dNTPs, 0.01% (w/v) gelatin, and 1.25 units Thermus aquaticus DNA polymerase (Taq polymerase—Perkin Elmer, Norwalk, Conn.). For amplification of FLB1 YAC DNA, a primer complementary to the 5' end of the Alu consensus sequence (Oncor Laboratories, Gaithersberg, Md.), designated SAL1, was used=5'-

AGGAGTGAGCCACCGCACCCAGCC-3' (SEQ ID No:34)at a final concentration of 0.6 μM. For amplification of LR40 YAC DNA, 0.2 μM primer PDJ34 was used. See, C. Breukel et al., *Nucleic Acids Res.,* 18, 3097 (1990). Samples were overlaid with mineral oil, denatured at 94° C. for 5 minutes, then subjected to 30 cycles of 1 minute 94° C. denaturation, 1 minute 55° C. annealing, and 5 minutes 72° C. extension. The last extension step was lengthened to 10 minutes. Electrophoresis of 15 μl of PCR products was performed on a 1.5% agarose gel, which was Southern blotted and hybridized with a probe prepared by random-hexamer-primed labelling of synthetic poly(dG-dT)-poly (dA-dC) (Pharmacia, Piscataway, N.J.) using [α-$^{32}$P]dCTP, as described by A. P. Feinberg et al., *Anal. Biochem.,* 137. 266–267 (1984). Fragments hybridizing with the dinucleotide repeat probe were identified and were subsequently purified by electrophoresis on a low-melt agarose gel. Fragments were excised and reamplified by PCR as above.

For LR40, reamplified DNA was repurified by low-melt gel electrophoresis, and DNA extracted from excised bands by passage through a glasswool spin column as described by D. M. Heery et al., *Trends Genet.,* 6, 173 (1990). A purified 1.2-kb fragment was cloned into pBluescript plasmid modified as a "T-vector" as described by D. Marchuck et al., *Nucleic Acids Res.,* 19, 1154 (1990). From this clone, a 0.6-kb HincII restriction fragment containing a GT repeat was subcloned into pBluescript plasmid, and sequenced on an Applied Biosystems, Inc. (Foster City, Calif.) automated sequencer.

For SB1, a reamplified 1-kb fragment was ethanol precipitated and blunt-end cloned into pBluescript plasmid. Plasmid DNA was isolated and PCR amplified in one reaction with M13 Reverse primer plus BamGT primer (5'-CCCGGATCCTGTGTGTGTGTGTGTGTG-3') (SEQ ID No:35) and in a second reaction M13 Universal primer and BamCA primer (5'-CCCGGATCCACACACACACACACACAC-3'). (SEQ ID NO:36) See, C. A. Feener et al., *Am. J. Hum. Genet.,* 48, 621–627 (1991). PCR conditions were as above except primers were used at 1 μM concentration; 2.5 units Taq polymerase and approximately 30 ng DNA were used per reaction, with final reaction volumes of 100 μl, and an annealing temperature of 50° C. Products were precipitated, resuspended, and digested with BamH1 (product of Universal primer reaction) or BamH1 and HincII (product of Reverse primer reaction). These two fragments were cloned into pBluescript plasmid and sequenced as above.

Dinucleotide repeats were cloned at AM10 from a YAC containing this locus. A λFixII library was constructed using DNA from this yeast clone, and human clones were identified by filter hybridization using human placental DNA as a probe. A gridded array of these human clones was grown, and filters containing DNA from these clones were hybridized with a $^{32}$P-labelled poly(dG-dT)-poly(dA-dC3) probe as described above. DNA was prepared from positive clones, digested with various restriction enzymes, and analyzed by agarose gel electrophoresis. Southern blotting and hybridization were carried out with the poly(dG-dT)-poly(dA-dC) probe. A 1-kb fragment hybridizing with the dinucleotide repeat probe was identified, clones into M13, and sequenced.

4. PCR Analysis

Primer sequences and concentrations, and PCR cycle times used for amplification of dinucleotide repeat sequences from human genomic DNA are presented in Table 1. For the LR40 polymorphism, primer set "A" was used for analysis of the TX-SCA1, LA-SCA1, and MS-SCA1 kindreds, while primer set "B" was used for all other kindreds. Buffer compositions were as follows: 50 mM KC1, 10 mM Tris-C1 pH 8.3, 1.25 mM $MgC1_2$ (1.5 mM $MgC1_2$ for AM10GA), 250 μM dNTPs (200 μM dNTPs for AM10GA), 0.01% (w/v) gelatin, and 0.5–0.625 unit Taq polymerase. For the LR40 analysis, 2% formamide was included in the PCR buffer. When primer set B was used for LR40 analysis, 125 μM dNTPs, 1.5 mM $MgC1_2$, and 1 unit Taq polymerase were used. All reaction volumes were 25 μl and contained 40 ng genomic DNA. Four microliters of each reaction was mixed with 2 μl formamide loading buffer, denatured at 90°–100° C. for 3 minutes, cooled on ice, and 2–4 μl was used for electrophoresis on a 4% or 6% polyacrylamide/7.65 M urea sequencing gel for 2–3 hours at 1100 V. PCR assay conditions have been reported previously for D6S202 and D6S109. See, L. P. W. Ranum et al., *Nucleic Acids Res.,* 19, 1171 (1991); and F. LeBorgne-Demarquoy et al., *Nucleic Acids Res.,* 19, 6060 (1991).

TABLE 1

Primers and PCR conditions for amplification of dinucleotide repeat sequences

| Marker/Type | Primers[a] | PCR Steps | PCR Cycles |
|---|---|---|---|
| AM10GA/$(GA)_n$ | AAGTCAGCCTCTACTCTTTGTTGA (SEQ ID NO: 37)<br>CTTGGAGCAGTCTGTAGGGAG (SEQ ID NO: 38) | 94° C. for 30 sec.<br>55° C. for 30 sec.<br>72° C. for 30 sec. | 30 |
| SB1/$(GT)_n$ | TGAAGTGATGTGCTCTGTTC (SEQ ID NO: 39)<br>AAAGGGGTAGAGGAAATGAG (SEQ ID NO: 40) | 94° C. for 60 sec.<br>60° C. for 60 sec.<br>72° C. for 60 sec. | 30 |
| LR40/$(GT)_n$ set A | AGGAGAGGGGTCATGAGTTG (SEQ ID NO: 41)<br>GGCTCATGAATACATTACATGAAG (SEQ ID NO: 42) | 94° C. for 60 sec.<br>58° C. for 60 sec.<br>72° C. for 60 sec. | 25 |
| LR40/$(GT)_n$ set B | CTCATTCACCTTAGAGACAAATGGATAG (SEQ ID NO: 43)<br>ATGGTATAGGGATTTTNCCAAACCTG (SEQ ID NO: 44) | 94° C. for 60 sec.<br>60° C. for 60 sec.<br>72° C. for 45 sec. | 27 |

[a]Primers are shown as 5' to 3' sequence. The first primer of each pair was end-labelled with γ-$^{32}$P ATP and polynucleotide kinase. Primer concentrations were 1 nM.

5. SCA1 Linkage Analysis

The D6S109, AM10GA, D6S89, SB1, LR40 and D6S202 markers were analyzed for linkage to SCA1 using the computer program LINKAGE version 5.1 which includes the MLINK, ILINK, LINKMAP, CLODSCORE and CMAP programs. See, G. M. Lathrop et al., *Proc. Natl. Acad. Sci. USA,* 81, 3443–3446 (1984). Age dependent penetrance classes were assigned independently for each of the families included in the analysis. Marker alleles were recoded to reduce the number of alleles segregating in a family to four, five or six alleles to simplify the analysis. The allele frequencies for the various markers were based on the frequencies of the alleles among the spouses in each family and were determined separately for the two American black kindreds, for the Italian kindreds, and for the Caucasian kindreds from Minnesota, Michigan, and Mississippi, with the following exception-the allele frequencies for D6S109 in the MI and MN kindreds were based on the frequencies of the alleles in the CEPH families.

Maximum LOD scores for the various markers were calculated with the MLINK program by running each of the analyses separately for the various families, at theta values with increments of 0.0005 to 0.001, and then adding the values of each of the kindreds. The analyses were done separately to ensure that the allele frequencies for the various markers were representative for each of the ethnically diverse families. As a control, the recombination fractions at the maximum lod scores ($Z_{max}$) between each marker and SCA1 were calculated using the ILINK program after the allele frequencies for each marker were set equal to one another. In all cases the recombination frequencies were the same and $Z_{max}$ values were very similar to those reported in Table 5 below.

6. CEPH Linkage Analysis

Forty CEPH families were typed for the GT repeat markers D6S109, D6S202 and LR40. The original alleles were recoded to five alleles. The SB1 and AM10 markers were typed in a subset of the CEPH panel which defined 26 recombinants from 18 different families between D6S109 and D6S89. The CLODSCORE program was used for the two-point analyses and CMAP was used for the three-and four-point analyses. For the three-point and four-point analyses, the interval between the mapped markers was fixed based on the two point $\theta_m=\theta_f$ results. The likelihood of the location of the test locus (SCA1) was calculated at 10 different positions within each interval. The test for sex difference in the $\Theta$ values was performed using a $\chi^2$ statistic, with $\chi^2=2(1n10)[Z(\theta_m,\theta_f)-Z(\theta=\theta_m=\theta_f)]$, where $Z(\theta_m, \theta_f)$ is the overall $Z_{max}$ for arbitrary $\theta_m$ and $\theta_f$, while $Z(\theta=\theta_m=\theta_f)$ is the $Z_{max}$ constrained to $\theta_m=\theta_f$. Under homogeneity (H1), $\chi^2$ approximates a $\chi^2$ with 1 d.f. Rejection of homogeneity occurs when $\chi^2>3.84$.

B. Results

1. Dinucleotide Repeat Cloning and Sequencing and Analysis

Dinucleotide repeats SB1 and LR40 were amplified directly from YAC clones by Alu-primed PCR and the dinucleotide repeat containing fragments were identified by hybridization. The PCR products were cloned either directly or by further amplification using tailed poly(GT) or poly (CA) primers paired with an Alu primer. In addition, two dinucleotide repeats were subcloned from a lambda phage clone from a library constructed from a YAC at the AM10 locus.

Dinucleotide repeats from the SB1, LR40, and AM10 loci were sequenced. At LR40, the cloned repeat sequence was $(CA)_{16}TA(CA)_{10}$ (SEQ ID NO:45). The AM10 fragment contained two repeat sequences separated by 45 bp of nonrepeat sequence. The first repeat, designated AM10GA, was $(GA)_2ATGACA(GA)_{11}$(SEQ ID NO:46). The second repeat, designated AM10GT, was not used in this study because upon analysis of the TX-SCA1 kindred it yielded the same information as the AM10GA repeat. The AM10GT repeat consists of $(GA)_2AA(GA)_6GTGA(GT)_{16}AT(GT)_5$ (SEQ ID NO:47). Primer information for AM10GT is available through the Genome Data Base. At SB1, the repeat tract was not sequenced; only flanking sequence was determined.

As there are differences in allele distributions of markers among the different races, allele frequencies are reported here separately for the CEPH kindreds (Caucasian) and the TX-SCA1 kindred (American black) (Table 2). CEPH allele frequencies were based on 72 independent chromosomes for SB1, 82 independent chromosomes for AM10,and on the full set of 40 families for D6S109 and LR40. TX-SCA1 allele frequencies were based on 45 independent chromosomes for LR40, 43 independent chromosomes for SB1, 45 independent chromosomes for AM10, and 42 independent chromosomes for D6S109.

TABLE 2

Allele frequencies of new markers

| | D6S109[b] | AM10GA | | SB1 | | LR40 | | D6S202[b] |
|---|---|---|---|---|---|---|---|---|
| Allele[a] | TXSCA1 | TXSCA1 | CEPH | TXSCA1 | CEPH | TXSCA1 | CEPH | TXSCA1 |
| $A_0$ | — | — | 0.012 | 0.070 | — | — | — | — |
| $A_1$ | 0.048 | 0.022 | 0.024 | 0.163 | 0.027 | 0.244 | 0.022 | 0.05 |
| $A_2$ | 0.024 | 0.289 | 0.220 | 0.186 | 0.166 | 0.045 | 0.043 | 0.11 |
| $A_3$ | 0.119 | — | 0.024 | 0.070 | 0.333 | 0.111 | 0.065 | 0.11 |
| $A_4$ | 0.024 | 0.333 | 0.232 | 0.023 | — | 0.133 | 0.033 | 0.13 |
| $A_5$ | 0.071 | 0.267 | 0.488 | 0.186 | 0.097 | 0.111 | 0.272 | 0.11 |
| $A_6$ | 0.261 | — | — | 0.093 | 0.111 | — | 0.098 | 0.03 |
| $A_7$ | 0.024 | 0.089 | — | 0.093 | 0.153 | 0.022 | 0.054 | 0.22 |
| $A_8$ | 0.095 | — | — | 0.093 | 0.083 | 0.045 | 0.076 | 0.13 |
| $A_9$ | 0.143 | — | — | — | 0.014 | 0.089 | 0.054 | 0.08 |
| $A_{10}$ | — | — | — | — | — | 0.022 | 0.065 | 0.03 |
| $A_{11}$ | 0.048 | — | — | 0.023 | — | 0.133 | 0.011 | — |
| $A_{12}$ | 0.048 | — | — | — | — | 0.045 | 0.054 | — |
| $A_{13}$ | 0.048 | — | — | — | 0.014 | — | 0.097 | — |

TABLE 2-continued

Allele frequencies of new markers

| | D6S109[b] | AM10GA | | SB1 | | LR40 | | D6S202[b] |
|---|---|---|---|---|---|---|---|---|
| Allele[a] | TXSCA1 | TXSCA1 | CEPH | TXSCA1 | CEPH | TXSCA1 | CEPH | TXSCA1 |
| $A_{14}$ | 0.071 | — | — | — | — | — | 0.033 | — |
| $A_{15}$ | — | — | — | — | — | — | 0.023 | — |

[a]Alleles are numbered such that the largest allele is assigned the lowest number and each successive allele is two bp smaller. For D6S109, $A_1$ = 215 bp, for Am10GA, $A_0$ = 123 bp, for SB1, $A_0$ = 220 bp, for LR40, TXSCA1 $A_1$ = 241 bp, (primer set A, Table 1), CEPH $A_1$ = 267 bp (primer set B, Table 1), for D6S202, $A_1$ = 154 bp.

[b]CEPH data published for D6109 (L. P. W. Ranum et al., Am. J. Hum. Genet. 49, 31–41 (1991) and D6S202 (F. LeBorgne-Demarquoy et al., Nucl. Acids Res. 19, 6060 (1991).

2. Genetic Linkage Data a. CEPH families. In order to establish a well-defined genetic map for the SCA1 region, newly isolated DNA markers were mapped using the CEPH reference families. Results of pairwise linkage analyses in CEPH kindreds are shown in Table 3. No recombination was observed between AM10GA and D6S89 ($\theta$=0.00, $Z_{max}$=15.1) using a subset of the CEPH panel which defined 26 recombinants between D6S109 and D6S89. The markers D6S109 and LR40 are close to D6S89, with recombination fractions of 0.067 ($Z_{max}$=71.4) and 0.04 ($Z_{max}$=84.5) respectively.

Selected multipoint analyses were performed to position the newly isolated markers D6S109, LR40, D6S202 with respect to markers previously mapped using the CEPH panel. The CMAP program was used for three- and four-point linkage analyses to position D6S109 relative to D6S88 and D6S89 and to position LR40 and D6S202 relative to each other and to D6S89 and F13A. For the three-point analyses, the D6S88-D6S89 interval was fixed based on the two-point recombination fraction in CEPH and the lod score was calculated at various recombination fractions. The order D6S88-D6S109-D6S89 is favored over the next most likely order by odds of $4\times10^3$:1 (Table 4). For the four-point analyses, both the D6S89-D6S202-F13A and the D6S89-LR40-F13A intervals were fixed based on the two-point recombination fractions; lod scores were then calculated for LR40 and D6S202 at various $\theta$ values on the respective fixed maps. The order D6S89-LR40-D6S202-F13A is favored over the next most likely order in both analyses; odds in favor were 400:1 when the position of LR40 was varied and were $1\times10^6$ to 1 when D6S202 was varied (Table 4).

The order of AM10GA and D6S89 could not be determined using the D6S109/D6S89 CEPH recombinants. However, the order AM10GA-D6S89-SB1 was deduced by characterization of overlapping yeast artificial chromosome clones containing these markers (see below). Furthermore, one end of this contig is present in a well characterized radiation-reduced hybrid known to contain D6S109 and other centromeric markers, indicating the order D6S109-AM10GA-D6S89-SB1.

TABLE 3

Pairwise linkage results in CEPH

| Marker Pair | $\theta_m = \theta_f$ | $Z_{max}$ | $\theta_m$ | $\theta_f$ | $Z_{max}$ | $\chi^2$ |
|---|---|---|---|---|---|---|
| HLA and D6S88 | 0.128 | 26.4 | 0.103 | 0.168 | 26.8 | 1.86 |
| D6S109 | 0.126 | 48.4 | 0.062 | 0.176 | 51.0 | 12.1* |
| AM10 | 0.608 | 0.0440 | 0.301 | 0.500 | 0.246 | 0.929 |
| D6S89 | 0.158 | 43.3 | 0.091 | 0.225 | 46.6 | 15.2* |
| SB1 | 0.574 | 0.0190 | 0.299 | 0.500 | 0.400 | 0.381 |

TABLE 3-continued

Pairwise linkage results in CEPH

| Marker Pair | $\theta_m = \theta_f$ | $Z_{max}$ | $\theta_m$ | $\theta_f$ | $Z_{max}$ | $\chi^2$ |
|---|---|---|---|---|---|---|
| LR40 | 0.213 | 25.5 | 0.116 | 0.306 | 30.0 | 20.8* |
| HZ30 | 0.251 | 21.6 | 0.191 | 0.318 | 23.6 | 8.95* |
| F13A | 0.291 | 8.81 | 0.255 | 0.326 | 9.14 | 1.52 |
| D6S88 and D6S109 | 0.017 | 48.6 | 0.024 | 0.009 | 48.8 | 0.846 |
| AM10 | 0.654 | 0.0290 | 0.499 | 0.696 | 0.047 | 0.0820 |
| D6S89 | 0.086 | 36.1 | 0.076 | 0.098 | 36.2 | 0.0750 |
| SB1 | 0.203 | 1.09 | 0.136 | 0.687 | 1.36 | 1.27 |
| LR40 | 0.088 | 31.1 | 0.078 | 0.104 | 31.2 | 0.350 |
| HZ30 | 0.135 | 30.4 | 0.124 | 0.152 | 30.4 | 0.340 |
| F13A | 0.180 | 10.2 | 0.158 | 0.217 | 10.3 | 0.626 |
| D6S109 and AM10 | 0.730 | 0.933 | 0.170 | 0.502 | 1.67 | 3.39 |
| D6S89 | 0.067 | 71.4 | 0.035 | 0.090 | 72.5 | 5.15* |
| SB1 | 0.742 | 1.95 | 0.113 | 0.501 | 4.32 | 10.9* |
| LR40 | 0.109 | 50.6 | 0.050 | 0.152 | 52.9 | 10.5* |
| HZ30 | 0.162 | 36.6 | 0.147 | 0.174 | 36.7 | 0.515 |
| F13A | 0.207 | 14.4 | 0.211 | 0.204 | 14.4 | 0.0368 |
| AM10 and D6S89 | 0.000 | 15.1 | 0.000 | 0.000 | 15.1 | 0.000 |
| SB1 | 0.000 | 13.2 | 0.000 | 0.000 | 13.2 | 0.000 |
| LR40 | 0.021 | 8.74 | 0.000 | 0.050 | 9.11 | 1.74 |
| HZ30 | 0.000 | 13.8 | 0.000 | 0.000 | 13.8 | 0.000 |
| F13A | 0.135 | 3.48 | 0.042 | 0.253 | 4.39 | 4.16* |
| D6S89 and SB1 | 0.000 | 25.0 | 0.000 | 0.000 | 25.0 | 0.000 |
| LR40 | 0.040 | 84.5 | 0.030 | 0.049 | 84.7 | 0.925 |
| HZ30 | 0.078 | 76.0 | 0.075 | 0.077 | 76.0 | 0.0230 |
| F13A | 0.151 | 30.7 | 0.139 | 0.160 | 30.7 | 0.248 |
| SB1 and LR40 | 0.033 | 14.4 | 0.022 | 0.044 | 14.5 | 0.350 |
| HZ30 | 0.026 | 17.5 | 0.032 | 0.020 | 17.5 | 0.0300 |
| F13A | 0.136 | 4.80 | 0.119 | 0.155 | 4.84 | 0.170 |
| LR40 and HZ30 | 0.079 | 64.8 | 0.092 | 0.050 | 65.0 | 1.09 |
| F13A | 0.131 | 29.1 | 0.121 | 0.140 | 29.2 | 0.189 |
| HZ30 and F13A | 38.4 | 0.109 | 0.122 | 0.106 | 38.4 | 0.0092 |

*Indicates statistically significant differences were observed in the recombination fractions when the assumption of homogeneity ($\theta_m = \theta_f$) was rejected; that is the likelihood that $\chi^2 > 3.84$ with 1 degree of freedom should occur by chance in $P < 0.05$.

TABLE 4

Three and four point linkage analyses in the CEPH families

| Order | $Z_{max}$ | Relative Odds | Odds in favor |
|---|---|---|---|
| D6S109-D6S88-D6S89 | 90.6 | $2 \times 10^8$ | |
| D6S88-D6S109-D6S89 | 94.2 | $8 \times 10^{11}$ | $4 \times 10^3$ |
| D6S88-D6S89-D6S109 | 82.3 | 1 | |
| LR40-D6S89-D6S202-F13A | 96.1 | $1 \times 10^{34}$ | |
| D6S89-LR40-D6S202-F13A | 98.6 | $4 \times 10^{36}$ | 400:1 |
| D6S89-D6S202-LR40-F13A | 73.9 | $8 \times 10^{11}$ | |
| D6S89-D6S202-F13A-LR40 | 62.0 | 1 | |
| D6S202-D6S89-LR40-F13A | 89.5 | $1 \times 10^{32}$ | |
| D6S89-D6S202-LR40-F13A | 57.5 | 1 | |

TABLE 4-continued

Three and four point linkage analyses in the CEPH families

| Order | $Z_{max}$ | Relative Odds | Odds in favor |
|---|---|---|---|
| D6S89-LR40-D6S202-F13A | 95.5 | $1 \times 10^{38}$ | $10^6$:1 |
| D6S89-LR40-F13A-D6S202 | 77.6 | $1 \times 10^{20}$ | |

b. SCA1 kindreds. Results of pairwise linkage analyses in SCA1 kindreds are shown in Table 5. AM10GA, D6S89, and SB1 are all closely linked to SCA1. No recombination was observed between AM10GA and SCA1; the lod score is 42.1 at a recombination fraction of 0.00. The recombination fraction between D6S89 and SCA1 is 0.004 (lod score of 67.6). The recombination fraction between SB1 and SCA1 is 0.007 (lod score of 39.5). D6S109, LR40 and D6S202 are linked to SCA1 as well, but at greater distances (recombination fractions of 0.04, 0.03, and 0.08 respectively). Based on genetic mapping in nine large kindreds, the SCA1 locus is very close to D6S89 and AM10GA, with a $Z_{max}-1$ support interval less than or equal to 0.02 in both cases.

SCA1—one recombination event between SCA1 and LR40 and three recombination events between SCA1 and D6S202. These events are depicted in FIG. 4 (all recombination events depicted in FIG. 4 are in affected individuals).

II. Mapping and Cloning the Critical Region for the SCA1 Gene

A 2.5-Mb yeast artificial chromosome (YAC) contig was developed with the ultimate goal of defining and cloning the region likely to contain the SCA1 gene (SCA1 critical region).

A. Materials and Methods

1. Cell lines

I-7 is a human-hamster hybrid cell line which contains the short arm of chromosome 6 as its only human chromosome. See, H. Y. Zoghbi et al., *Genomics,* 6, 352–357 (1990). R86, R78, R72, R54 and R17 are radiation reduced hybrid cell lines retaining various portions of 6p22–p23. See, H. Y. Zoghbi et al., *Genomics,* 9, 713–720 (1991). R54 retains markers known to be telomeric to D6589, such as D6S202 and F13A.

2. Generation of new DNA markers and Sequence-Tagged Sites (STSs)

DNA from a radiation reduced hybrid retaining D6S89 (R86) and DNAs from four radiation hybrids (R78, R72, R54 and R17) which do not retain D6S89 but retain markers immediately flanking D6S89 were used in comparative Alu-PCR to isolate region-specific DNA markers. See, D. L. Nelson et al., *Proc. Natl. Acad. Sci. USA,* 86, 6686–6690 (1989); and H. Y. Zoghbi et al., *Genomics,* 9, 713–720 (1991). In addition, R78 was useful in eliminating markers derived from the centromeric region of 6p. H. Y. Zoghbi et al., *Genomics,* 9, 713–720 (1991). Alu-PCR was carried out using Alu primers 559 and 517 individually (D. L. Nelson et al., *Proc. Natl. Acad. Sci. USA,* 86, 6686–6690 (1989)) as well as PDJ 34 (C. Breukel et al., *Nucleic Acids Res.,* 18, 3097 (1990)). Alu-PCR fragments found to be present in R86 but absent in R78, R72, R54 and R17 were identified and were cloned into EcoRV-digested pBluescript IIKS+ plasmid (Stratagene, La Jolla, Calif.) which was modified using the T-vector protocol. See, D. Marchuk et al., *Nucleic Acids Res.,* 19, 1154 (1990). Cloned fragments were sequenced on an Applied Biosystems, Inc. (Foster City, Calif.) automated sequencer to establish STSs.

TABLE 5

Pairwise lod scores for SCA1 and dinucleotide repeat markers

| | Recombination fraction | | | | | | | | | Support |
|---|---|---|---|---|---|---|---|---|---|---|
| | 0 | 0.001 | 0.05 | 0.1 | 0.2 | 0.3 | 0.4 | Z[a] | θ[a] | Interval[b] |
| SCA1:D6S109 | −∞ | 22.68 | 33.81 | 32.03 | 25.19 | 16.56 | 7.24 | 33.82 | 0.04 | 0.02 to 0.09 |
| SCA1:AM10GA | 42.14 | 42.06 | 38.48 | 34.51 | 25.86 | 16.63 | 7.30 | 42.14 | 0.00 | 0.00 to 0.02 |
| SCA1:D6S89 | −∞ | 67.35 | 62.78 | 56.39 | 42.51 | 27.56 | 12.09 | 67.58 | 0.004 | 0.00 to 0.02 |
| SCA1:SB | −∞ | 39.02 | 37.33 | 33.92 | 26.16 | 17.53 | 8.33 | 39.46 | 0.007 | 0.00 to 0.03 |
| SCA1:LR40 | −∞ | 27.80 | 31.77 | 29.73 | 23.61 | 16.11 | 7.77 | 32.08 | 0.03 | 0.001 to 0.07 |
| SCA1:D6S202 | −∞ | 4.41 | 25.80 | 26.47 | 22.12 | 14.77 | 6.51 | 26.61 | 0.08 | 0.04 to 0.14 |

[a]Z = maximum lod score, θ = recombination fraction at maximum lod score.
[b]$Z_{max} - 1$ = support interval for θ (Cytogenet Cell Genet 40, 356–359 (1985)).

3. Analysis of Key Recombinants

One recombination event between D6S89 and SCA1 has been confirmed in an affected individual. The patient, individual MI-2 in FIG. 4, was also recombinant at SB1, although uninformative at LR40 and D6S202. He carried a disease haplotype at the HLA, D6S109 and AM10 loci, demonstrating that SCA1 is centromeric to D6S89, as indicated by the rightmost arrow in FIG. 4. To eliminate the possibility of sample mix-up, the patient's DNA was reextracted from a hair sample and retyped for D6S109, D6S89, D6S202, LR40, AM10GA, and SB1. The results from the hair sample matched those from the cell line originally established from the patient's blood. The patient's medical records were carefully reexamined and it was confirmed that he did indeed have ataxia. In addition, his haplotypes were consistent with those of a sister and a daughter.

D6S109 lies centromeric to D6S89; six recombination events have been observed between D6S109 and SCA1, as shown in FIG. 4. At this point, D6S109 is the centromeric marker closest to SCA1. The arrows in FIG. 4 denote the maximum region common to all affected chromosomes, and therefore the maximum possible region containing the SCA1 gene, which extends from D6S89 to D6S109.

No additional marker-SCA1 recombination events have been observed between D6S89 and SB1. Markers further telomeric to SB1 show additional recombination with 3. Isolation and Characterization of YAC Clones The Washington University YAC library (B. H. Brownstein et al., *Science,* 244, 1348–1351 (1989)), and the CEPH YAC library (H. M. Albertsen, et al., *Proc. Natl. Acad. Sci. USA,* 87, 4256–4260 (1990)), were screened using a PCR-based method. See, E. D. Green et al., *Proc. Natl. Acad. Sci. USA,* 87, 1213–1217 (1990); and T. J. Kwiatkowski et al.,

*Nucleic Acids Res.,* 18, 7191–7192 (1990). PCR amplifications were carried out in 25–50 ml final volume with 50 mM KC1, 10 mM Tris-HC1 pH 8.3, 1.25 mM $MgC1_2$, 0.01% (w/v) gelatin, 250 μM of each dNTP; 1.25 units of Amplitaq polymerase (Perkin-Elmer, Norwalk, Conn.) and 1 μM of each primer. PCR cycle conditions are specified in Table 6.

TABLE 6

STSs and YACs in 6p22–p23

| Probe | Primer set | YACs[a] | Annealing temp.[b] |
|---|---|---|---|
| D6S89 | cttgttcatctgccttgtgc (SEQ ID NO: 48) acctaagcgactgcctaaac (SEQ ID NO: 49) | B126G2, B134D5, B134B3, B214D3, C5C12, 191D8, 299B3, 379C2, 468D12, 124G2, 511H11 | 55° C. |
| AM10 (D6S335) | ttaaggaagtgttcacatcaggg (SEQ ID NO: 50) aattgtgcttatgtcactggg (SEQ ID NO: 51) | A23C3, A183C6, A250D5, B238F12, A91D2 | 55° C. |
| A250D5-L (D6S337) | aattctggagaggatgt (SEQ ID NO: 52) tggttcttttttggtag (SEQ ID NO: 53) | 195B5, 242C5, 475A6, 30F12 | 44° C. |
| 64U | catcgtgttgtgtggtgaag (SEQ ID NO: 54) ctcagacgctaaactcaagg (SEQ ID NO: 55) | 492H3, 172B5, 227B1, 261H7 | 50° C. |
| D6S288 | atgatccgtggtagtggc (SEQ ID NO: 56) aggacctgttactgacgcc (SEQ ID NO: 57) | 60H7, 351B10 | 55° C. |
| D6S274 | ctcatctgttgaatggggat (SEQ ID NO: 58) cttaaatgctatgccttccg (SEQ ID NO: 59) | 486F9, 149H3, 42A5, 283B2, 320E12 | 55° C. |
| FLB1 (6S339) | tgcaaatccctcagttcact (SEQ ID NO: 60) tgcttgactttgccatgttc (SEQ ID NO: 61) | 140H2, 270D3, 274D12, 401D6, 57G3, 168F1 | 50° C. |
| AM12 (D6S336) | atacccatacggatttgagg (SEQ ID NO: 62) gcaacactatcaggctaagaatg (SEQ ID NO: 63) | A71B3, 228A1, 193B3, 90A12, 539C11, 53G12, 35E8 | 55° C. 55° C. |
| 53G12-L | caaataccagcaactcaccagc (SEQ ID NO: 64) ggttccttcagcatcctacattc (SEQ ID NO: 65) | 3G6, 82G12, 98G5, 135F6, 198C8, 330G1 | 58° C. |

[a]YACs in this study are from the CEPH and Washington University libraries. I.D. numbers identify the library source (Washington University I.D. numbers are preceded by a letter). Several YACs were identified with more than one STS; for such information, please refer to Table 2.

[b]PCR conditions were 94° C. for 4 minutes followed by 35–40 cycles of 94° C. denaturation for 1 minute, annealing at the specified temperature for 1 minute, and 72° C. extension for 2 minutes. A final extension step of 7 minutes at 72° C. was used. PCR buffer and primer concentrations are as described in the text; for the 53G12-L STS a final concentration of 2% formamide was used in the PCR reaction.

YACs in this study are from the CEPH and Washington University libraries. I.D. numbers identify the library source (Washington University I.D. numbers are preceded by a letter). Several YACs were identified with more than one STS; for such information, please refer to Table 2.

PCR conditions were 94° C. for 4 minutes followed by 35–40 cycles of 94° C. denaturation for 1 minute, annealing at the specified temperature for 1 minute, and 72° C. extension for 2 minutes. A final extension step of 7 minutes at 72° C. was used. PCR buffer and primer concentrations are as described in the text; for the 53G12-L STS a final concentration of 2% formamide was used in the PCR reaction.

Yeast DNA-agarose blocks were prepared as described by D. C. Schwartz et al., *Cell,* 37, 67–75 (1984); and G. J. B. van Ommen et al. in *Human Genetic Diseases-A Practical Approach*; K. E. Davies, ed.; pp. 113–117; IRL Press, Oxford (1986). All the YAC clones were analyzed by pulsed-field gel electrophoresis (PFGE) to determine the insert size and to confirm that a single YAC was present in a specific colony. YAC inserts were sized by electrophoresing yeast DNA through a 1% Fastlane agarose (FMC, Rockland, Me.) gel in 0.5× TAE (20 mM Tris-acetate/0.5 mM EDTA). For rapid detection of possible overlaps between YAC clones isolated at different STSs, the labelled Alu-PCR products of new YACs were hybridized to filters containing Alu-PCR products of individual YACs in the region. Most of the YAC clones were tested for chimerism using the Alu-PCR dot blot method described by S. Banfi et al., *Nucleic Acids Res.,* 20, 1814 (1992). The Alu-PCR products from YAC clones were hybridized to a dot-blot containing the Alu-PCR products from monochromosomal or highly reduced hybrids representing each of the 24 different human chromosomes as previously described by S. Banfi et al., *Nucleic Acids Res.,* 20, 1814 (1992). In addition a dot-blot containing Alu-PCR products from radiation reduced hybrids representing different segments of 6p was used to insure that a YAC does not contain two non-contiguous segments from 6p. Ends of YAC clones were isolated either by inverse-PCR as previously described by G. Joslyn et al., *Cell,* 66, 601–613 (1991) or by Alu-vector PCR as described by D. L. Nelson et al., *Proc. Natl. Acad. Sci. USA,* 88, 6157–6161 (1991). Alu-vector PCR was carried out using Alu-primers PDJ34 and SAL1, as described by C. Breukel et al., *Nucleic Acids Res.,* 18, 3097 (1990); and the pYAC4 vector primers described by M. C. Wapenaar et al., *Hum. Mol. Genet.,* 2, 947–952 (1993) and analogous vectors described by G. P. Bates et al., *Nature Genetics,* 1, 180–187 (1992). All YAC ends were regionally mapped by hybridization to Southern blots containing EcoRI-digested DNAs from the YAC clones and from the hybrid cell lines: I-7, R86, and R72.

4. Cosmid Library Preparation from YACs

Cosmid libraries were prepared from four YAC clones; 227B1, 195B5, A250D5, and 379C2. Genomic DNA from YACs was partially digested with MboI and cloned into cosmid vector superCos 1 (Stratagene, La Jolla, Calif.) following the manufacturer's recommendations. Clones containing human inserts were identified using radiolabeled sheared human DNA as a probe.

5. Long Range Restriction Analysis

YAC plugs were digested to completion using rare-cutter restriction enzymes as described by M. C. Wapenaar et al., *Hum. Mol. Genet.,* 2, 947–952 (1993) and analogously by G. A. Silverman et al., *Proc. Natl. Acad. Sci. USA,* 86, 7485–7489 (1989). Enzymes were purchased from New England Biolabs (Beverly, Mass.) and Boehringer Manheim Biochemicals (Indianapolis, Ind.) and were used as recommended by the manufacturer. All PFGE analyses were performed on a Bio-Rad CHEF apparatus under conditions that separate DNA fragments in the 50 kb to 600 kb range. The gels were stained with ethidium bromide, and either acid nicked or subjected to 200,000 mJ of UV energy in a UV Stratalinker 1800 (Stratagene, La Jolla, Calif.). The gels were denatured in 0.4 N NaOH and transferred to Sure Blot hybridization membrane (Oncor, Gaithersburg, Md.) in either 10×SSC (1.5 M NaC1/150 mM NaCitrate) or 0.4 N NaOH according to the manufacturer's recommendations. Hybridizations of the filters were carried out using the probes listed in Table 6 and FIG. 6. Also pBR322 BamHI/PruII fragments of 2.5 kb and 1.6 kb specific for the left (TRP/CEN) and right (URA) pYAC4 vector arms respectively, were used. Probes were radiolabelled using the random priming technique described by A. P. Feinberg et al., *Anal. Biochem.,* 137, 266–267 (1984); repetitive sequences were blocked using sheared human placental DNA as previously described by P. G. Sealy et al., *Nucleic Acids Res.,* 13, 1905–1922 (1.985).

6. Dinucleotide Repeat Analysis

Primer sequences and PCR cycle conditions are presented in Table 6. Buffer conditions were the same as for Alu-PCR. All reaction volumes were 25 $\mu$l and contained 40 ng of genomic DNA. One primer of each pair was labelled at the 5' end with [$\gamma$-$^{32}$P]dATP. Four microliters of each reaction was mixed with 2 $\mu$l formamide loading buffer, denatured at 90°–100° C. for 3 minutes, cooled on ice and 4–6 $\mu$l was used for electrophoresis on a 4% polyacrylamide/7.65 M urea sequencing gel.

B. Results

1. Generation of Sequence Tagged Sites in 6p22–p23 and YAC Screening

Comparative analysis of the Alu-PCR products from the radiation hybrid, which retains D6S89 (R86) and from the four radiation hybrids deleted for D6S89 but retaining markers which flank D6S89 (R78, R72, R54 and R17) allowed the identification of three new DNA fragments that were present in R86 but absent in the other four. These three DNA fragments termed, AM10, AM12 and FLB1 were isolated and mapped using a 6p somatic cell hybrid panel and the radiation reduced hybrid panel (H. Y. Zoghbi et al., *Genomics,* 9, 713–720 (1991)) to confirm their regional localization. All three mapped to 6p and to R86 confirming their close proximity to the D6S89 locus. These three Alu-PCR fragments were subcloned and sequenced to establish sequenced tagged sites (STSs). STSs at AM10, AM12, FLB1 and D6S89 were used to screen the Washington University and the CEPH YAC libraries (H. M. Albertsen, et al., *Proc. Natl. Acad. Sci. USA,* 87, 4256–4260 (1990); and B. H. Brownstein et al., *Science,* 244, 1348–1351 (1989)). YACs isolated at these four STSs were analyzed for overlap. Insert termini from the YACs representing contig ends were isolated, subcloned and were sequenced to establish new STSs for further YAC walking. In one case an STS was established by using a subclone from a cosmid derived from a cosmid library generated for YAC 195B5.

Recently several highly informative dinucleotide repeat markers have been identified and mapped genetically by J. Weissenbach et al., *Nature,* 359 794–801 (1992). As discussed above, two markers, D6S274 and D6S288 were found to map within the SCA1 critical region and were subsequently used to screen the YAC libraries. Using the STSs listed in Table 6, YAC clones were isolated.

2. Characterization of YAC Clones

The sizes of the YAC inserts were determined by pulsed-field gel electrophoresis (PFGE); insert sizes ranged from 75–850 kb. Given the high frequency of insert chimerism, an Alu-PCR based hybridization strategy for rapid detection of chimerism, as described by S. Banfi et al., *Nucleic Acids Res.,* 20, 1814 (1992) was used. Thirty of the YAC clones were tested using this approach and eight (27%) were found to be chimeric. Insert ends isolated from YACs determined to be non-chimeric by the dot blot hybridization approach mapped to 6p22–p23 with the exception of the two ends from 198C8 which proved to map to other chromosomes.

Two approaches were used, inverse-PCR (G. Joslyn et al., *Cell,* 66, 601–613 (1991)) and Alu-PCR (analogous to that described by D.L. Nelson et al., *Proc. Nati. Acad. Sci. USA,* 86, 6686–6690 (1989)) to isolate YAC ends. In total, 34 YAC ends were isolated; inverse-PCR yielded 26 ends and Alu-vector PCR yielded 8 ends. To isolate the left end of the 195B5 YAC we screened a cosmid library prepared from this YAC using pYAC4 left end sequences (S. K. Bronson et al., *Proc. Nati. Acad. Sci. USA,* 88, 1676–1680 (1991)) as a probe. This approach was taken because inverse-PCR yielded an end which was predominantly an Alu-containing sequence and Alu-PCR failed in yielding an end. Cosmid clone A32 was found to contain the left end of 195B5 and a subclone, 64U, was used to establish an STS for further YAC library screenings.

In order to confirm the 6p22–p23 regional origin of all YAC ends or subclones, these fragments were used as probes against Southern blots containing EcoRI-digested DNAs from a somatic cell hybrid retaining 6p (I-7), from radiation reduced hybrids known to retain fragments of 6p (H. Y. Zoghbi et al., *Genomics,* 9, 713–720 (1991)) and from the YAC clones at a particular STS.

3. Probe Content Mapping of YACs

In order to define the degree of overlap between the clones and to detect possible rearrangements such as internal deletions of the YACs, a probe content mapping strategy was used based on: 1) PCR analysis of all the clones using all the STSs in the region including both the ones described in Table 6, and those at highly informative dinucleotide repeats such as AM10-GA and SB1; and 2) hybridization of Southern blots containing EcoRI-digested DNAs from YACs in the relevant region, with densely-spaced DNA probes derived from YAC ends, cosmids subclones of YACs, or Alu-PCR fragments from YACs. The results of this analysis for a representative subset of the YACs (32 clones) are summarized in Table 7. Thirty-nine YAC clones form an uninterrupted YAC contig from D6S274 to 82G12-R (right end of YAC clone 82G12). Other than an internal deletion in one YAC 351B10) no other deletions were detected within the resolution of this analysis; furthermore the extent of chimerism for some YAC clones (such as 270D12 and 140H2) was determined. The centromere-telomere orientation of the YAC contig on 6p was determined using both genetic data as well as physical mapping data. Using dinucleotide repeats analysis at D6S109, AM10GA, D6S89, and SB1 in the key individual with recombination event between D6S89 and SCA1 revealed that the recombination event occurred between AM10GA and D6S89. Given that D6S109 is centromeric to D6S89, the recombination analysis suggests that AM10GA is centromeric to D6S89. The centromere-telomere position of SB1 with respect to D6S89 could not be determined genetically.

TABLE 7

Characterization of YACs using 6p22–p23 STSs and YAC fragments

| YAC | Size (kb) | Chimerism | D6S274 | 60H7Lg | D6S288 | 64U | AS5005-L | AM10-GA | AM10 | 168F1-R | C5C12-R |
|---|---|---|---|---|---|---|---|---|---|---|---|
| 149H3 | 345 | N | + | + | − | − | − | | | | |
| 60H7 | 580 | N | + | + | + | − | − | | | | |
| 351B10 | 330 | N | + | − | + | − | − | | | | |
| 227B1 | 560 | N | + | + | + | + | − | | | | |
| 172B5 | 345 | Y | − | − | + | + | − | | | | |
| 195B5 | 365 | N | − | | − | + | + | − | − | | − |
| 475A6 | 365 | N | | | | − | + | − | − | | − |
| 242C5 | 340 | N | | | | − | + | + | + | | − |
| A250D5 | 250 | N | | | | − | + | + | + | − | − |
| A23C3 | 530 | Y | | | | − | − | − | + | − | − |
| A18306 | 120 | N | | | | − | − | − | + | − | − |
| B238F12 | 390 | Y | | | | − | − | + | + | − | − |
| A91D2 | 325 | N | | | | − | − | − | + | − | − |
| 191D8 | 650 | N | | | | | | − | + | + | + |
| 379C2 | 575 | N | | | | | | − | + | + | + |
| C5C12 | 75 | N | | | | | | − | − | − | + |
| B214D3 | 200 | N | | | | | | | − | | − |
| 299B3 | 375 | N | | | | | | − | − | + | + |
| 468D12 | 280 | N | | | | | | | − | + | + |
| 168F1 | 400 | N | | | | | | | − | + | + |
| 270D3 | 650 | Y | | | | | | | − | − | + |
| 274D12 | 240 | N | | | | | | | − | − | − |
| 140H2 | 440 | Y | | | | | | | − | − | − |
| 57G3 | 400 | N | | | | | | | − | − | − |
| 401D6 | 340 | N | | | | | | | − | − | − |
| 193B3 | 850 | Y | | | | | | | | | |
| 228A1 | 350 | Y | | | | | | | | | |
| 90A12 | 650 | Y | | | | | | | | | |
| 35E8 | 400 | N | | | | | | | | | |
| 53G12 | 370 | N | | | | | | | | | |
| 135F6 | 400 | N | | | | | | | | | |
| 82G12 | 380 | N | | | | | | | | | |

| YAC | Size (kb) | D6S89 | B214D3-R | FLB1 | 53G12-R | 401D6-R | AM12 | 135F6-L | 53G12-L | 135F6-R | 83G12-R |
|---|---|---|---|---|---|---|---|---|---|---|---|
| 149H3 | 345 | | | | | | | | | | |
| 60H7 | 580 | | | | | | | | | | |
| 351B10 | 330 | | | | | | | | | | |
| 227B1 | 560 | | | | | | | | | | |
| 172B5 | 345 | | | | | | | | | | |
| 195B5 | 365 | | | | | | | | | | |
| 475A6 | 365 | | | | | | | | | | |
| 242C5 | 340 | | | | | | | | | | |
| A250D5 | 250 | − | − | − | | | | | | | |
| A23C3 | 530 | − | − | − | | | | | | | |
| A18306 | 120 | − | − | − | | | | | | | |
| B238F12 | 390 | − | − | − | | | | | | | |
| A91D2 | 325 | − | − | − | | | | | | | |
| 191D8 | 650 | + | + | − | | | | | | | |
| 379C2 | 575 | + | + | − | | | | | | | |
| C5C12 | 75 | + | − | − | | | | | | | |
| B214D3 | 200 | + | + | − | | | | | | | |
| 299B3 | 375 | + | + | + | | | | | | | |
| 468D12 | 280 | + | + | − | | | | | | | |
| 168F1 | 400 | + | | + | + | − | − | | | | |
| 270D3 | 650 | − | + | + | + | − | − | | | | |
| 274D12 | 240 | − | + | + | + | − | − | | | | |
| 140H2 | 440 | − | − | + | + | − | − | | | | |
| 57G3 | 400 | − | | + | + | + | − | | | | |
| 401D6 | 340 | − | + | + | + | + | − | | | | |
| 193B3 | 850 | | | − | − | + | + | − | − | − | − |
| 228A1 | 350 | | | − | − | + | + | − | − | − | − |
| 90A12 | 650 | | | − | − | + | + | − | − | − | − |
| 35E8 | 400 | | | − | + | + | + | + | + | − | − |
| 53G12 | 370 | | | − | + | + | + | + | + | − | − |
| 135F6 | 400 | | | | | | | + | + | + | − |
| 82G12 | 380 | | | | | | | − | + | + | + |

Note. (+) = present, (−) = absent; Y/N = chimerism is/not detected. YAC ends are identified by YAC names followed by L or R for left or right.

Figure 5A:
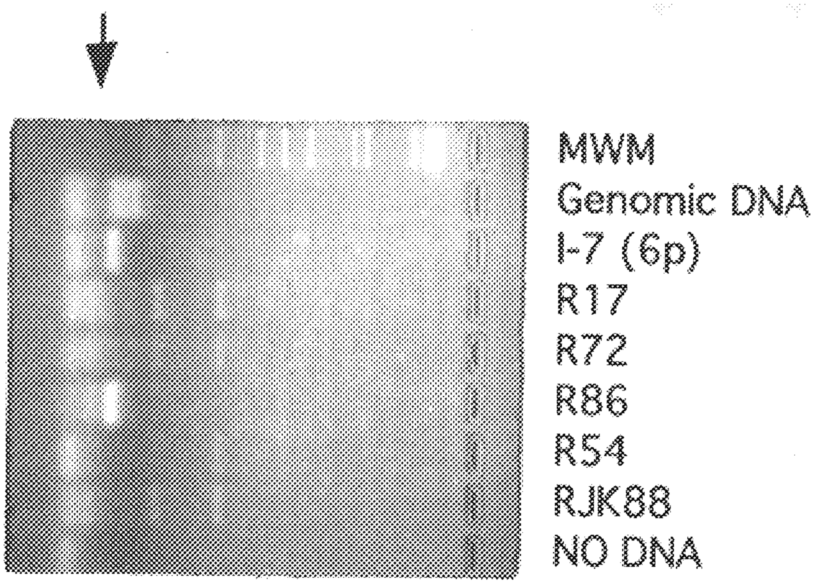
FIGS. 5A and 5B. Regional localization of 6p22–p23 STSs by PCR analysis of radiation reduced hybrids. Two panels (a and b) demonstrate the regional localization of D6S274, D6S288, and AM10GA. In each panel PCR amplification results are shown for genomic DNA, the I-7 cell line which retains 6p, the radiation reduced hybrids R17, R72, R86, and R54, and RJK88 hamster DNA. A blank control (c) is shown for every panel. R86 has been previously shown to retain D6S89; R17 and R72 are known to contain D6S88 and D6S108, two DNA markers which map centromeric to D6S89. An amplification product is seen in I-7, R17, R72, and R86 for D6S274 and D6S288, whereas the amplification product for AM10GA is only seen in I-7 and R86 confirming that D6S274 and D6S288 map centromeric to AM10GA and D6S89.
Figure 5B:
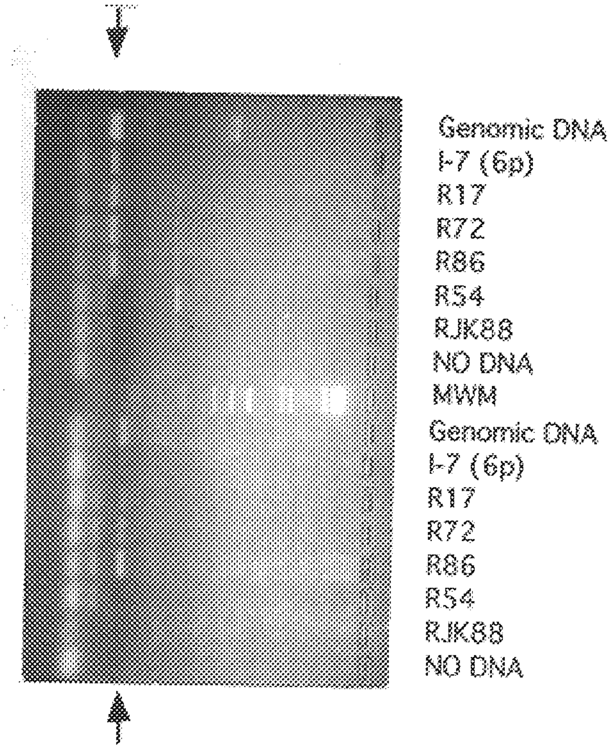

Physical mapping, using both radiation hybrids and YACs, was carried out to resolve the centromere-telomere order of the loci. The radiation reduced hybrids R17 and R72 are known to contain markers centromeric to D6S89; these markers include D6S108 and D6S88 which map centromeric to D6S109. See, H. Y. Zoghbi et al., *Genomics,* 9, 713–720 (1991). R72 also retains D6S109, but a small gap in R17 was revealed as this radiation hybrid did not retain D6S109, but was positive for an end isolated from a YAC at the D6S109 locus. Analysis of the radiation reduced hybrids revealed that D6S274 and D6S288 are present in R17, R72 and R86, whereas AM10GA, D6S89, and SB1 are present only in R86 (FIG. 5). Furthermore, STS content mapping with D6S260 and D6S289, two dinucleotide repeats that are telomeric to D6S288 (J. Weissenbach et al., *Nature,* 359 794–801 (1992) ), revealed that D6S260 is present in the same YACs as D6S89 and SB1 (379C2 and 168FI), and that D6S289 is present in 57G3 and 35E8 two YACs derived using the FLB1 and AM12 STS respectively. These data, confirm that the order of the loci as well as the centromere-telomere orientation of the YAC contig presented in FIG. 6 is correct.

Figure 6:
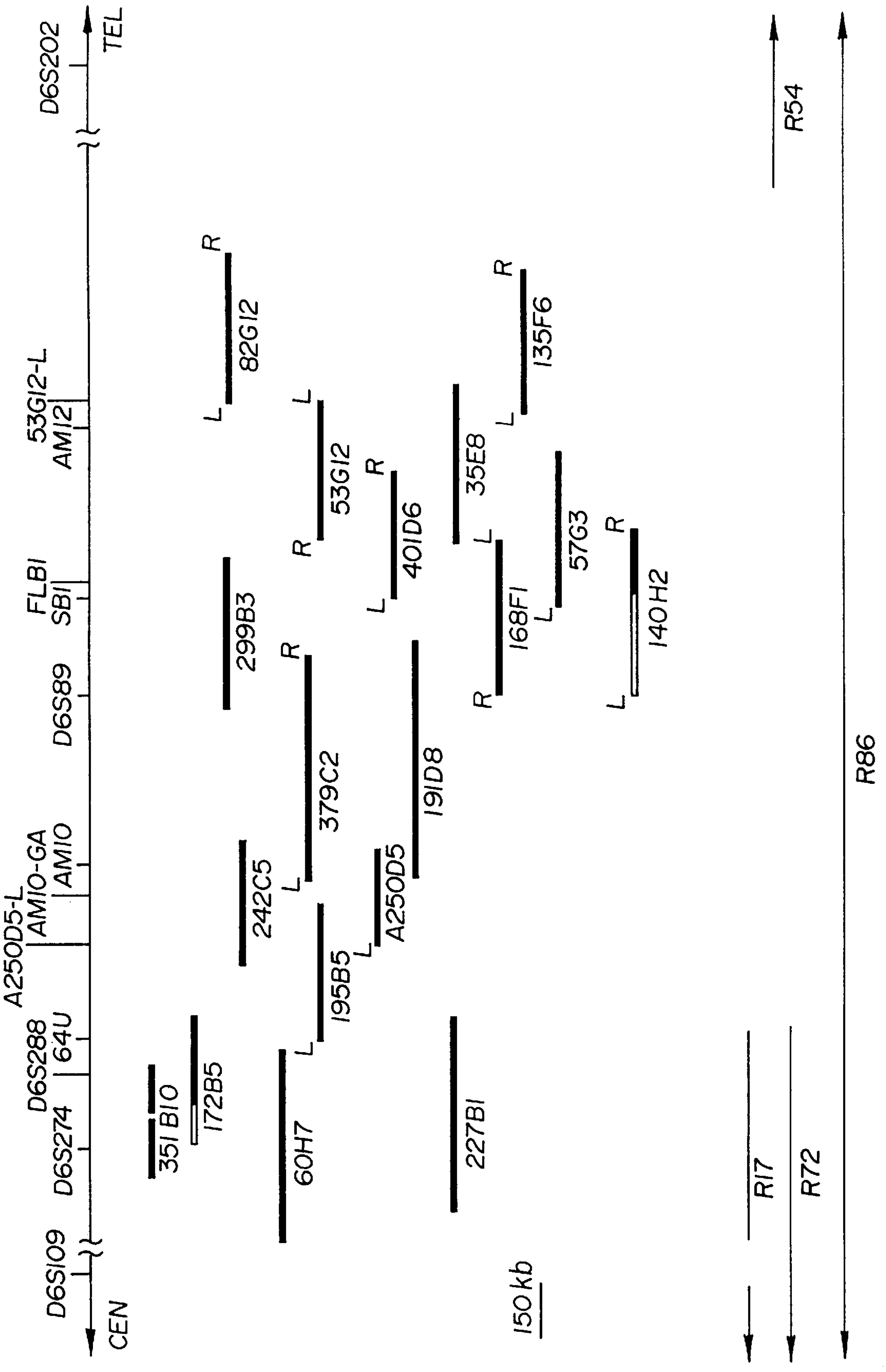
FIG. 6. A schematic diagram of 6p22–p23 region showing the new markers and the YAC contig. At the bottom of the diagram, the radiation hybrid reduced panel used for regional mapping is shown. YAC clones are represented as dark lines, open segments indicate a noncontiguous region of DNA. The discontinuity shown in YAC clone 351B10 indicate that this YAC has an internal deletion. All of the ends of the YAC clones that were isolated are designated by an "L" for the left end or an "R" for the right end.

FIG. 6 shows a selected subset of YAC clones which span the entire contig from D6S274 to 82G12-R. A minimal number of 8 YACs spans this region. The positions of the STSs which were used to isolate the YACs are also shown. Based on the size of the YACs and the degree of overlap, this contig is estimated to span 2.5 Mb of genomic DNA in 6p22–p23 with D6S89 located approximately in the middle.

4. Delineating the SCA1 Critical Region

Figure 7:
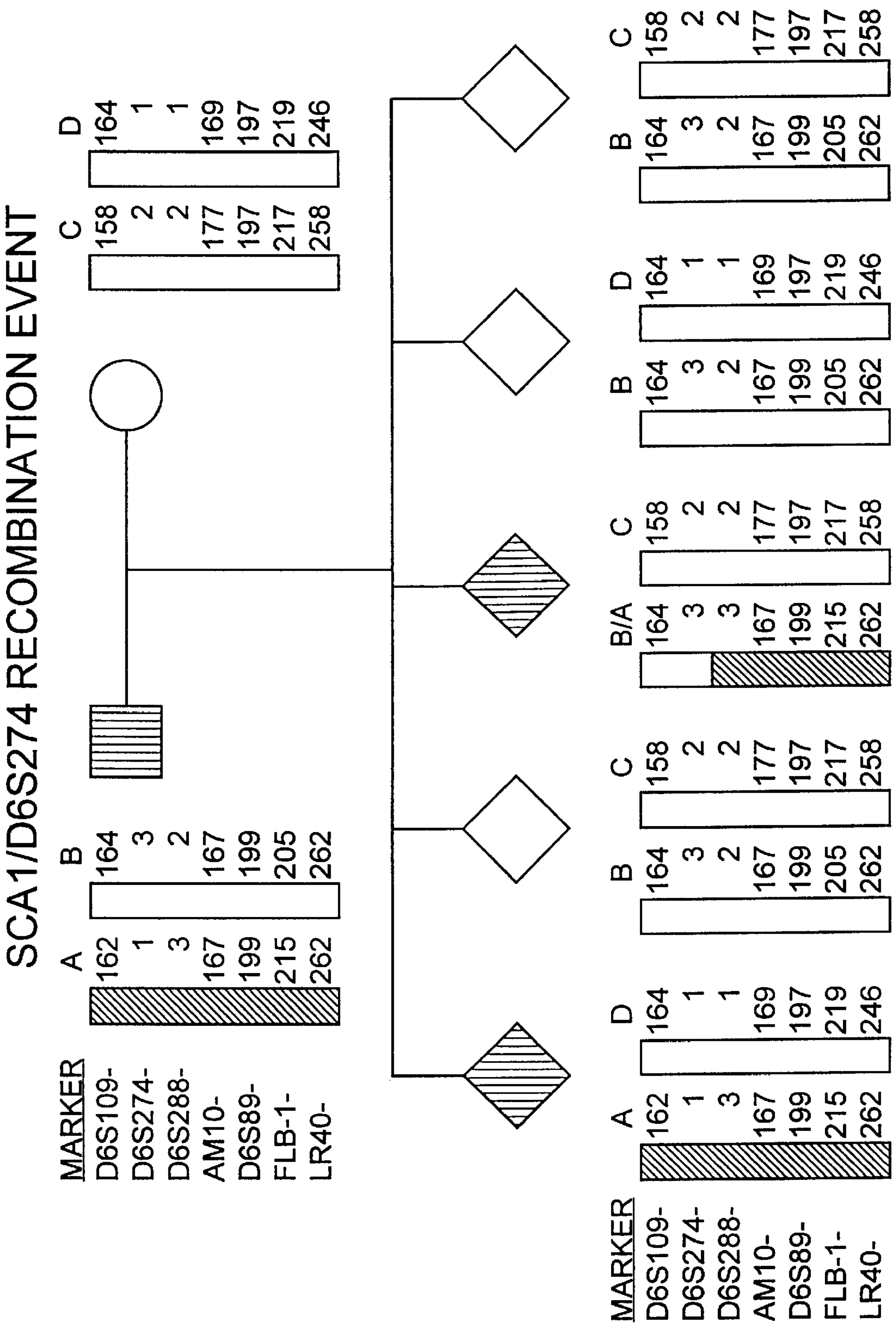
FIG. 7. Genotypic data for 6p22–p23 dinucleotide repeat markers are shown for a reduced pedigree from the MN-SCA1 kindred. This figure summarizes a second recombination event that led to the precise mapping of the SCA1 locus.
Figure 8:
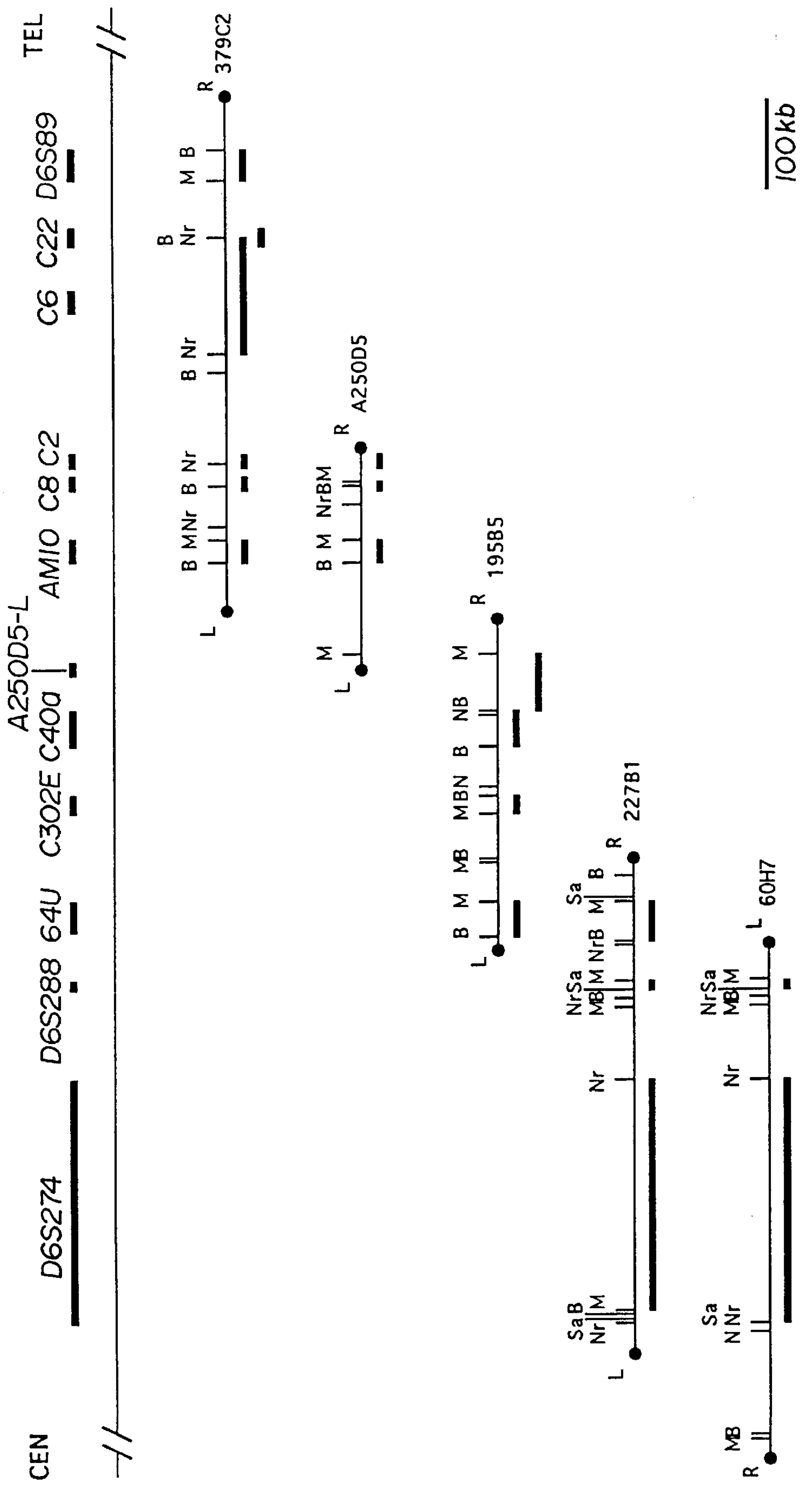
FIG. 8. Long-range restriction maps of YACs, 227B1, 60H7, 195B5, A250D5, and 379C2. YACs 351B10, 172B5, 172B5, and 168F1 were also used in the restriction analysis (data not shown). The restriction sites are marked as N, NotI; B, BssHII; Nr, NruI; M, MIuI, S, SacII, and Sa, SalI. A summary map of the SCA1 gene region with the position of the DNA markers used as probes (boxes) is shown. The centromere-telomere orientation is indicated by cen/tel respectively.

Genetic studies using recently identified dinucleotide repeats (AM10GA and SB1) showed that SCA1 maps centromeric to the D6S89 locus very close to AM10GA (peak load score of 42.1 at a recombination frequency of zero) in nine large SCA1 kindreds (Example 1, above). Thus D6S89 is the closest flanking marker at the telomeric end. Previously, the closest flanking marker at the centromeric end was D6S109, a dinucleotide repeat estimated to be 6.7 cM centromeric to D6S89. To identify a closer flanking marker at the centromeric end, we mapped D6S260, D6S274, D6S288 and D6S289, four dinucleotide repeat-containing markers known to map 6p22–p23 (J. Weissenbach et al., *Nature,* 359 794–801 (1992)). The regional mapping of these markers was done using radiation reduced hybrids and the YAC clones isolated from this region. These data revealed that D6S274 and D6S288 map centromeric to AM10GA as evident by amplification of DNA from radiation hybrids R17 and R72 which are known to be centromeric to AM10GA. Genotypical analysis of the DNAs from individuals with key recombination events between D6S109 and D6S89 as well as from affected and normal individuals (to establish chromosomal phase) from the five SCA1 kindreds (MN-SCA1, MI-SCA1, TX-SCA1, M-SCA1 and MS-SCA) was carried out. This analysis revealed no recombination between D6S288 and SCA1. A single recombination event between D6S274 and D6S288 was detected in individual MN-1 from the MN-SCA1 kindred (FIG. 7); this individual was one of the six individuals identified above as having a recombination event between SCA1 and D6S109. This analysis allowed us to identify D6S274 as the closest flanking marker at the centromeric end. These data combined with that discussed above determined that the SCA1 critical region maps between D6S274 and D6S89. This candidate region (1.2 Mb) is cloned in a minimum of four overlapping and non-chimeric YACs as shown in FIG. 8.

5. Long-Range Restriction Mapping

In order to have an estimate of the size of the YAC contig in the SCA1 critical region we performed long-range restriction analysis on YACs from this region. The YACs used for this analysis included: 227B1, 60H7, 351B10, 172B5, 195B5, A250D5, 379C2, and 168FI. The following rare-cutter restriction enzymes were used: NotI, BssHII, NruI, MluI, and SacII. Restriction fragments separated by PFGE and transferred onto nylon membranes, were detected by sequential hybridizations of the filter to several DNA probes which included: DNA probes specific for the left and right arm of the pYAC4 vector; insert termini for internal YAC clones; internal probes and cosmid subclones; and an Alu-specific probe. The position and names of all the probes used in the long-range restriction analysis is shown in FIG. 8. Based on this analysis the internal deletion for YAC 351B10 was confirmed. The extent of overlap between the YAC clones was determined. The size of the critical SCA1 region was estimated to be 1.2 Mb. Internal deletions and/or other rearrangements could not be excluded for the areas where a single YAC was analyzed by restriction enzyme analysis. These include approximately a 220 kb region within YAC 195B5 and a 335 kb region within YAC 379C2.

III. Expansion of an Unstable Trinucleotide Repeat in SCA1

A. Methods

1. Screening for Trinucleotide Repeats

Genomic DNA from YACs was partially digested with MboI and cloned into cosmid vector super CosI (Stratagene) following the manufacturer's protocol. Clones containing human inserts were identified by hybridization with radiolabeled human DNA and were arrayed on a gridded plate. Filter lifts of cosmid clones from YAC227B1 were screened for the presence of trinucleotide repeats by hybridization to [$\gamma$-$^{32}$P] end-labelled (GCT), oligonucleotide. In a parallel experiment, a mixture of 10 oligonucleotides representing the various permutations of trinucleotide repeats were end-labelled and hybridized to a Southern transfer of EcoRI-digested cosmids from YACs 195B5 and A250D5. Hybridizations were done in a solution of 1 M NaCl, 1% sodium dodecyl sulfate (SDS) and 10% (w/v) dextran sulphate. Filters were washed in 2×SSC (1×SSC is 0.15 M sodium chloride and 0.015 M sodium citrate), and 0.1% SDS at room temperature for 15 minutes, followed by a 15 minute wash at room temperature in a solution prewarmed to 67° C. Both strategies identified several positive clones, 22 of which were overlapping and contained the same 3.36-kb EcoRI fragment which hybridized to the $(GCT)_7$ (SEQ ID NO:66)probe and ultimately proved to have the CAG repeat by sequence analysis.

2. Genomic Digests and Southern Blots

Genomic DNAs were digested with TaqI (Boehringer Mannheim, Indianapolis, Ind.) or BstNI (New England Biolabs, Beverly, Mass.) according to the manufacturers recommendations. Southern blotting was done following standard protocols.

3. DNA Sequencing

To determine the DNA sequence in the region containing and flanking he CAG trinucleotide repeats, clone pGCT-7, containing the 3.36 kb-EcoRI fragment, was subcloned. A 400-bp fragment with CAG trinucleotide repeats was generated from pGCT-7 by Sau3AI digestion and subcloned into the BamHI site of pBluescriptKS-(Stratagene, La Jolla, Calf.) (clone pGCT-7.s1). In addition, pGCT-7 was digested with PstI to remove 1.3 kb of DNA and recircularized for transformation (clone pGCT-7.p2). The position of the trinucleotide repeats was determined by PCR using $(GCT)_7$ (SEQ ID NO:66) oligonucleotide and one of the flanking sequencing primers as PCR primers. Initial results indicated that the CAG trinucleotide repeats were on the reverse primer strand, about 1.3 kb from the reverse primer, that is, 400 bp from the PstI site. DNA sequencing was performed by di-deoxynucleotide chain-termination method using Sequenase and ΔTaq Cycle-Sequencing kit (United States Biochemical, Cleveland, Ohio). Both universal (−40) and reverse primers were used for clone pGCT-7.s1, while only universal (−40) primer was used for sequencing pGCT-7.p2.

4.RT-PCR and Northern Analysis

Total RNA was extracted from lymphoblastoid cells using guanidinium thiocyanate followed by centrifugation in a cesium chloride gradient. Poly(A)$^-$RNA was selected using Dynabeads oligo(dT)$_{25}$ from Dynal (Great Neck, N.Y.). First strand cDNA synthesis was carried out using MMLV reverse transcriptase (BRL, Gaithersberg, Md.). RT-PCR was carried out using hot start PCR with three cycles of: 97° C. for 1 minute, 59° C. for 1 minute, and 72° C. for 1 minute for the Pre1 and Pre2 primer set. Following that 33 cycles of 94° C. for 1 minute, 57° C. for 1 minute, and 72° C. for 1 minute were carried out. For the Rep1 and Rep2 primer pair the same PCR cycling conditions were followed at lower annealing temperatures of 57° C. and 55° C. respectively. The RT-PCR products were analyzed on 6% Nusieve agarose gel. The northern blot containing various human tissues was purchased from Clonetech (Palo Alto, Calif.).

5. PCR Analysis

Fifty ng of genomic DNA was mixed with 5 pmol of each primer (CAG-a/GAG-b or Rep-1/Rep-2) in a total volume of 20 μl containing 1.5 mM $MgCl_{2,\ 300}$ μM dNTPs (1.25 mM $MgCl_2$ and 250 μM dNTPs for Rep-1/Rep-2 primers), 50 mM KC1, 10mM Tris-HC1 pH 8.3, and 1 unit of Amplitaq (Perkin Elmer, Norwalk, Conn.). For the CAG-a/CAG-b primer pair [α-$^{32}$P]dCTP was incorporated in the PCR reaction, for Rep-1/Rep-2 primer pair the Rep-1 primer was labeled at the 5' end with [γ-$^{32}$P]dATP. Formamide was used at a final concentration of 2% when using the Rep-1/Rep-2 primer pair. Samples, overlaid with mineral oil, were denatured at 94° C. for 4 minutes followed by 30 cycles of denaturation (94° C., 1 minute), annealing (55° C., 1 minute), and extension (72° C., 2 minutes). Six microliters (μl) of each PCR reaction was mixed with 4 μl formamide loading buffer, denatured at 90° C. for 2 minutes, and electrophoresed through a 6% polyacrylamide/7.65 M urea DNA sequencing gel. Allele sizes were determined by comparing migration relative to an M13 sequencing ladder.

B. Results

1. Cloning of the CAG Repeat Region in SCA1

Figure 9:
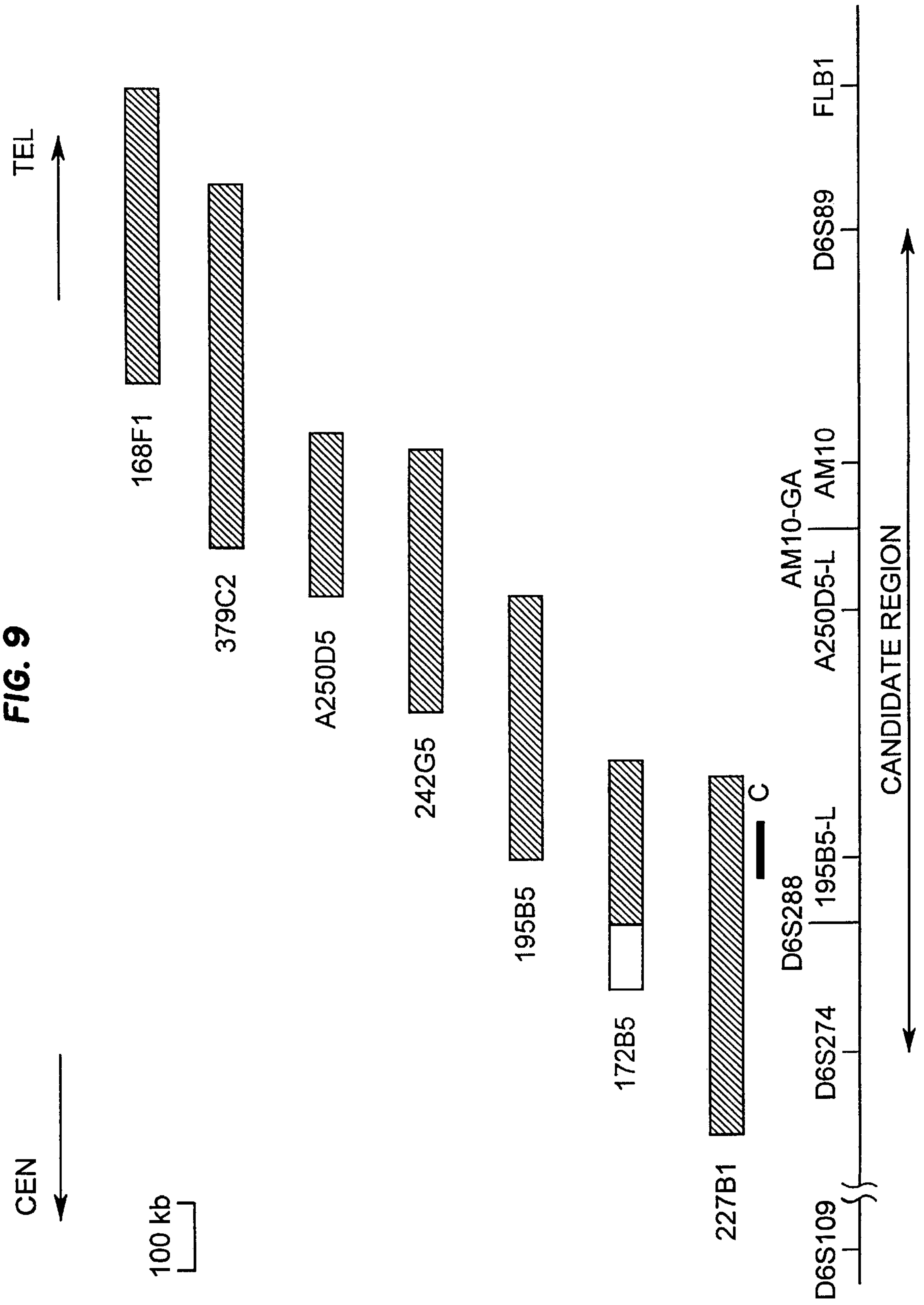
FIG. 9. Physical map of the SCA1 region. The positions of various genetic markers and sequence tagged sites (STSs) relative to the overlapping YAC clones are shown. AM10 and FLB1 are STSs developed using a radiation reduced hybrid retaining chromosome 6p22–p23, A205D5-L and 195B5-L are STSs from insert termini of YACs A250D5 and 195B5. D6S89, D6S109, D6S288 and D6S274, and AM10-GA are dinucleotide repeat markers used in the genetic analysis of SCA1 families. The SCA1 candidate region is flanked by the D6S274 and D6S89 markers which identify the closest recombination events. The YAC clones shown here are indicated by the cross-hatched markings. YAC 172B5 has two non-contiguous segments of DNA as indicated by the open bar for the non-6p segment. The YACs are designated according to St. Louis and CEPH libraries. The position of the cosmid contig (C) which contains the overlapping cosmids which are $(CAG)_n$ positive is indicated by a solid black bar. The overlap between the YACs was determined by long-range restriction analysis. Orientation is indicated as centromeric (Cen) and telomeric (Tel).

As discussed above, in efforts to clone the SCA1 gene, key recombination events were analyzed using several dinuclcotide repeat polymorphisms mapping to 6p22–p23 to identify the minimal region likely to contain the SCA1 gene. This analysis revealed that there were no recombination events between SCA1 and the centromeric marker D6S288 in five large kindreds or between SCA1 and the telomeric marker AM10GA in nine large kindreds. A single recombination event was detected between D6S274 and D6S288 identifying the closest flanking marker at the centromeric end to be D6S274. At the telomeric end, a single recombination event was detected between AM10GA and D6S89 and identified the latter as the flanking marker. A yeast artificial chromosome (YAC) contig extending from D6S274 to D6S89 and spanning the entire SCA1 candidate region was developed. A subset of the YAC clones encompassing this region is shown in FIG. 9. Long-range restriction analysis determined the size of the SCA1 candidate region to be approximately 1.2 Mb. Cosmid libraries were constructed from YACs 227B1, 195B5, A250D5, and 379C2. Arrays of cosmid clones containing human inserts were hybridized with an oligonucleotide consisting of tandemly repeated CAG, as well as with oligonucleotides containing other trinucleotide repeats. Several hybridizing cosmid clones were identified, 23 of which were positive for the CAG repeat and mapped to the region between D6S288 and AM10GA (FIG. 9). All 22 of these clones shared a common 3.36-kb EcoRI fragment that specifically hybridized to the CAG repeat.

2. Variability of the CAG Repeat Using Southern Analysis

Figure 10A:
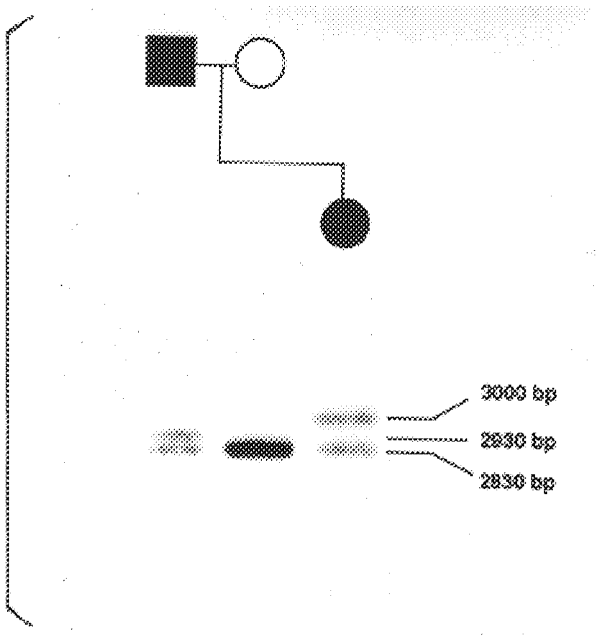
FIGS. 10A and 10B and 10C. Southern blot analysis of leukocyte DNA using the 3.36-kb EcoRI fragment which contains the repeat as a probe.
Figure 10B:
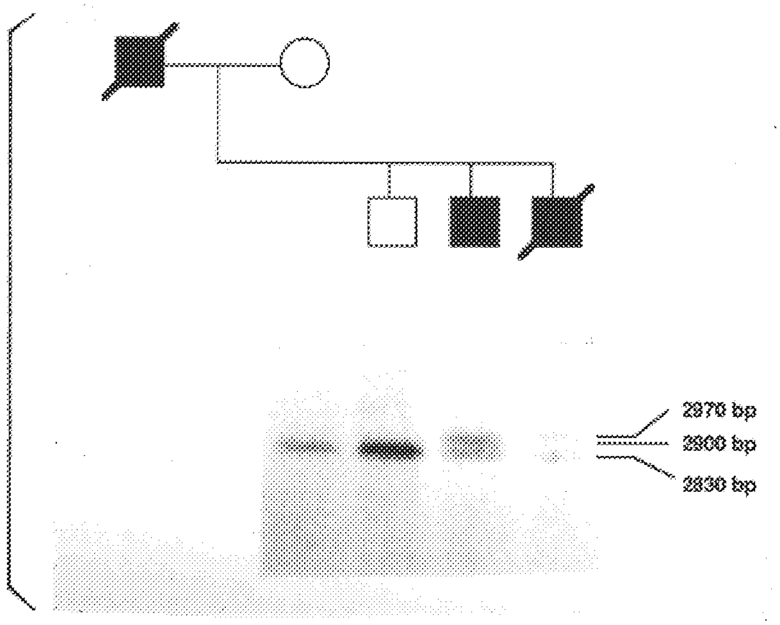

To test the genetic stability of this repeat in SCA1, we used Southern blotting analysis to examine families with juvenile onset SCA1. A two-generation reduced pedigree from the TX-SCA1 family is shown in FIG. 10*a*. Paternal transmission of SCA1 with an expansion of a TaqI fragment was noted. A 2830-bp fragment was detected in DNA from the unaffected spouse and on the normal chromosome from SCA1 patients, whereas a 2930-bp fragment was found in DNA from the affected father (onset at 25 years) and a 3000-bp fragment was detected in DNA from his affected child with an onset at 4 years. In a second SCA1 kindred, family MN-SCA1 (FIG. 10*b*), two offspring inherited SCA1 from their father and differed in their age at onset (25 years and 9 years). These individuals also differ in the size of the amplified TaqI fragment they inherited from their affected father, 2900-bp and 2970-bp, respectively.

Figure 10C:
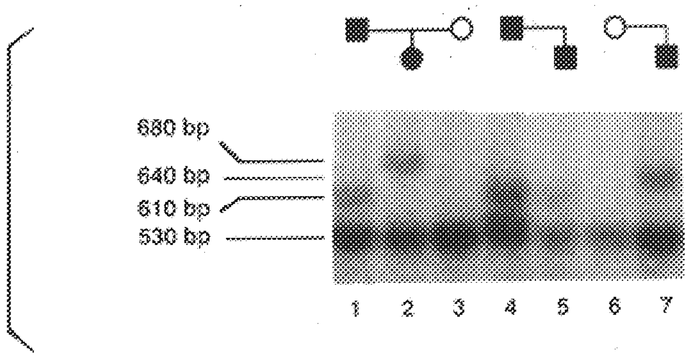

Enlargement of the $(CAG)_n$-containing fragment on SCA1 chromosomes from the same TX-SCA1 juvenile onset family was also demonstrated by Southern analysis following BstNI digestion. The BstNI fragment is 530-bp on normal chromosomes, is 610-bp in the SCA1 affected father, and is 680-bp in the affected juvenile onset offspring (FIG. 10*c*). In each of these families, nonpaternity was excluded by genotypic analysis with a large number (greater than 10) of dinucleotide repeat markers. In addition, the size of the $(CAG)_n$-containing TaqI fragment in DNA from 30 unaffected spouses was compared to the sizes of the repeat containing TaqI fragment in DNA from 62 individuals affected with late-onset SCA1. The affected individuals are from five different SCA1 families: LA-SCA1, MI-SCA1, MN-SCA1, MS-SCA1, and TX-SCA1. In all 30 unaffected spouses fragment sizes were approximately 2830-bp and no expansions or reductions were detected with transmission to offspring. In contrast, DNA from 58 of the 62 SCA1 affected individuals contained detectably expanded TaqI fragments ranging in size from 2860-bp to 3000-bp in addition to the 2830-bp fragment. The DNAs from the remaining four individuals were found to have an expansion when analyzed by polymerase chain reaction (PCR). The expanded fragment always segregated with disease, and in some cases the fragment expanded further in successive generations. In the juvenile cases the expanded restriction fragment was larger than that in the affected parent (uniformly the father in the cases analyzed) supporting the conclusion that a DNA sequence expansion is the mutational basis of SCA1.

3. Genomic DNA Analysis of Repeat Regions To identify the region involved in the DNA expansion, a 500-bp $(CAG)_n$-containing subclone of the 3.36-kb EcoRI fragment was sequenced, as was the entire 3.36-kb fragment (FIG. 1) (SEQ ID NO:1). This normal allele demonstrated 30 CAG repeat units. In two of the repeat units (position 13 and 15) a T was present instead of a G.

The expansion of the trinucleotide repeat was observed in all affected individuals examined by PCR from five different kindreds representing at least two ethnic backgrounds, American Black and Caucasian. Genotypic analysis using DNA markers that are very closely linked to SCA1 (D6S274, D6S288, AM10GA, D6S89 and SB1) revealed that there are four haplotypes segregating with disease among the five families analyzed.

4. The Trinucleotide Repeat is Transcribed

To test whether the CAG repeat lies within a gene, reverse transcription-PCR (RT-PCR) was performed using primers immediately flanking the repeat (Rep1 and Rep2) as well as primers which amplify a sequence immediately adjacent to the repeat (Pre1 and Pre2). The RT-PCR analysis confirms that the CAG repeat is present in mRNA from lymphoblasts. Furthermore, northern blot analysis of human poly(A)$^{-}$RNA from various tissues, using a 1.1 kb subclone (C208-1.1) from the 3.36-kb EcoRI fragment as a probe, identified a 10 kb transcript which is expressed in brain, skeletal muscle, placenta and to a lesser extent in kidney, lung and heart. The expression of this transcript is considerable in skeletal muscle. When the 3.36-kb EcoRI fragment was used as a probe on the northern blot the same size transcript was detected.

5. PCR Analysis of the CAG Repeat

To confirm that the CAG repeats were involved in the observed length variation, we analyzed the size of PCR-amplified fragments in 45 unaffected spouses and 31 SCA1 affected individuals using synthetic oligonucleotides that flank the CAG repeat. One pair of primers (CAG-a/CAG-b) was located within 9-bp of the repeats and identified length variation indicating that the CAG repeats are the basis of the variation.

Figure 11A:
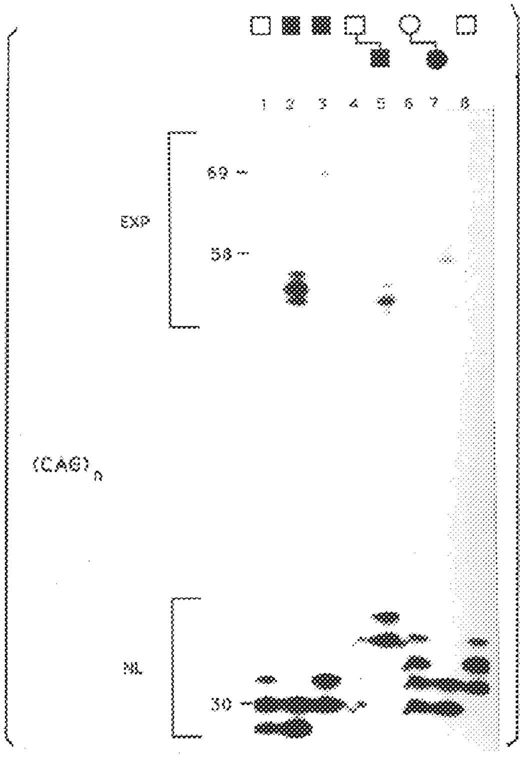
FIGS. 11A and 11B. Analysis of the PCR-amplified products containing the trinucleotide repeat tract in normal and SCA1 individuals. The CAG-a/CAG-b primer pair was used in panel (a) whereas the Rep-1/Rep-2 primer pair was used in panel (b). The individuals in lanes 1, 2 and 3 in panel (a) are brothers. The range for the normal (NL) and expanded (EXP) $(CAG)_n$ repeat units is indicated.
Figure 11B:
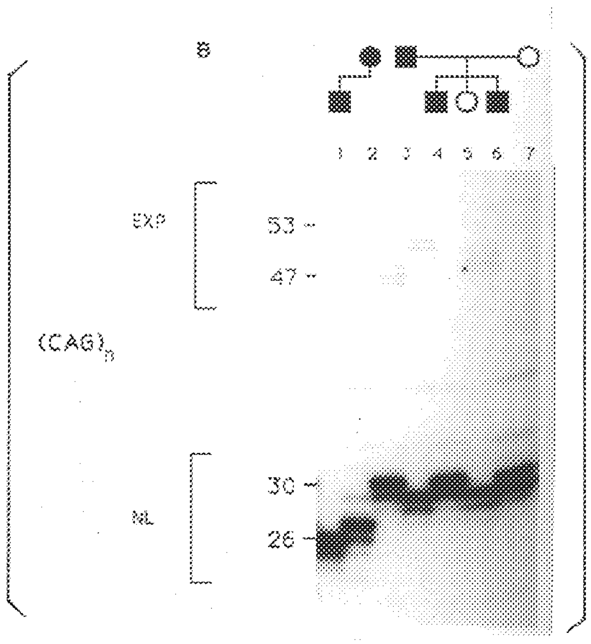
Figure 12:
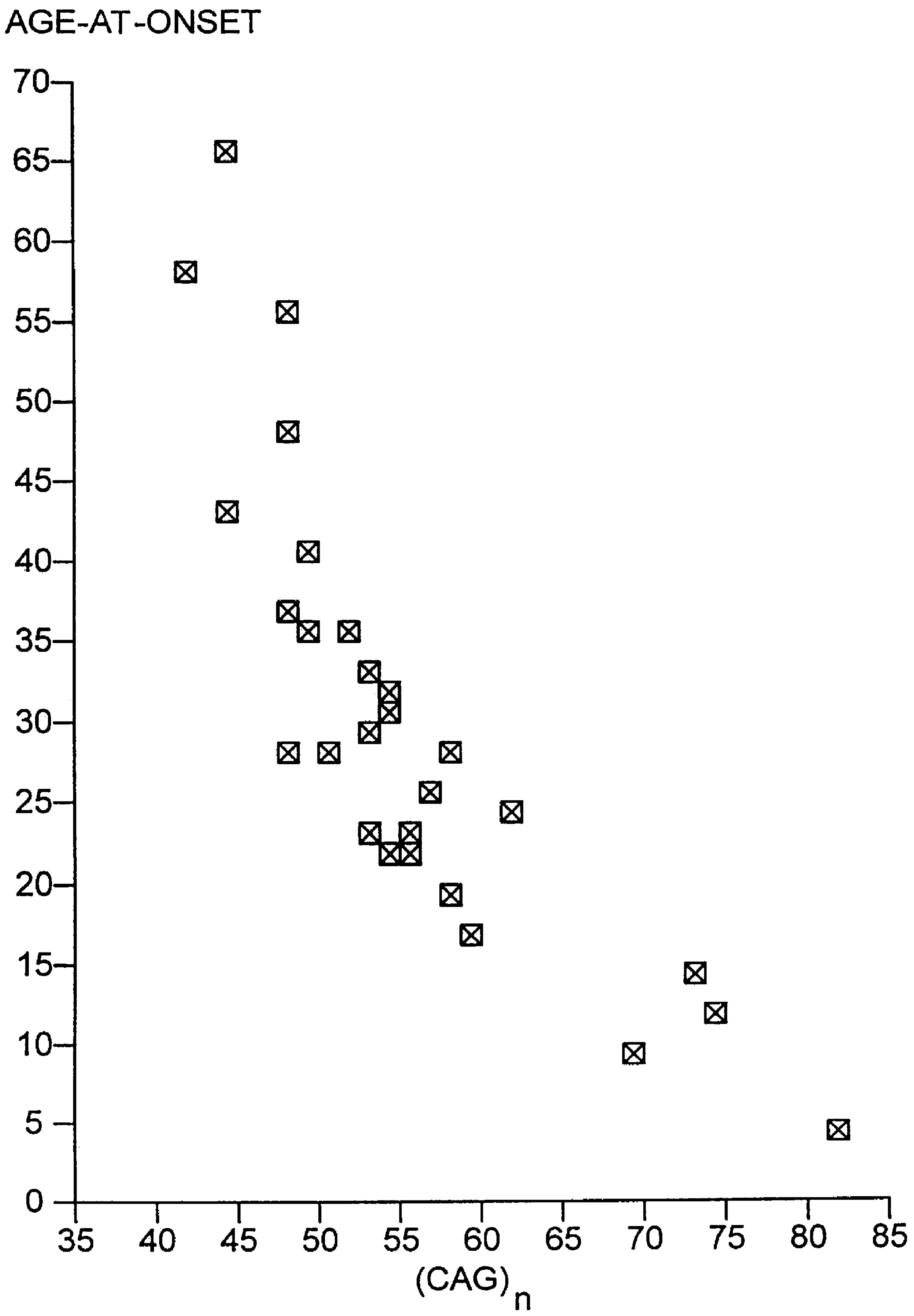
FIG. 12. A scatter plot for the age-at-onset in years versus the number of the $(CAG)_n$ repeat units is shown to demonstrate the correlation between the age-at-onset and the size of the expansion. A linear correlation coefficient of −0.845 was obtained. In addition a curvilinear correlation coefficient was calculated given the non-linear pattern of the plot. The curvilinear correlation coefficient is −0.936.

Normal individuals displayed 11 alleles ranging from 25 to 36 repeat units (Table 8). Heterozygosity in normal individuals was 84%. Examination of this sequence in 31 individuals affected with SCA1 demonstrated that each was a heterozygote with one allele within the size range seen in the normal individuals and a second expanded allele within a range of 43 to 81 repeat units (FIG. 11). Late onset SCA1 individuals showed at least 43 repeats, while 59–81 units were found in the juvenile cases. FIG. 12 depicts correlation between the age-at-onset and the number of the repeat units. A linear correlation coefficient (r) of −0.845 was obtained indicating that 71.4% ($r^2$) of the variation in the age-at-onset can be accounted for by the number of $(CAG)_n$ repeat units. The largest trinucleotide repeat expansion was noted in SCA1 patients with juvenile onset who typically had a more rapid course. It is of interest that all of these patients were offspring of affected males, which is reminiscent of Huntington disease where there is preponderance of male transmission in juvenile cases.

Sequence analysis of the fragment containing the CAG repeat indicated that there are several extended open reading frames. Translation of the repeat in one of these frames (389-bp) would encode polyglutamine.

TABLE 8

Comparison of the number of CAG repeat units on normal and SCA1 chromosomes

| Number of | Normal Chromosomes | | SCA1 Chromosomes | |
|---|---|---|---|---|
| Repeats | Number | Frequency | Number | Frequency |
| ≧60 | 0 | 0 | 4 | 0.13 |
| 50–59 | 0 | 0 | 17 | 0.55 |
| 43–49 | 0 | 0 | 10 | 0.32 |
| 37–42 | 0 | 0 | 0 | 0 |
| 35–36 | 1 | 0.01 | 0 | 0 |
| 30–34 | 49 | 0.55 | 0 | 0 |
| ≦29 | 40 | 0.44 | 0 | 0 |
| TOTAL | 90 | 1.00 | 31 | 1.00 |

IV. Isolation of SCA1 cDNA

A. Methods

1. Screening of cDNA Libraries.

Figure 13:
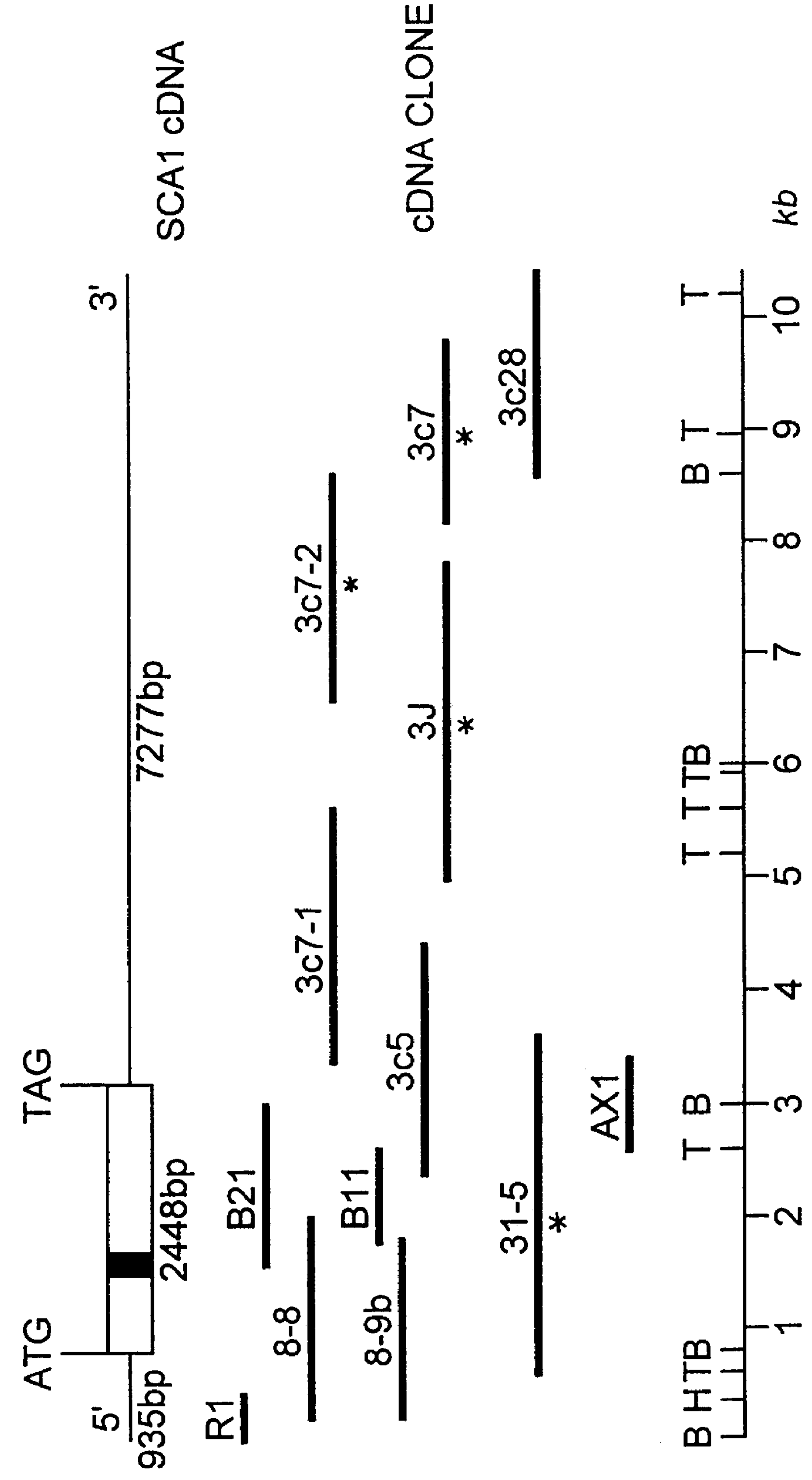
FIG. 13. Schematic representation of the SCA1 cDNA contig. A subset of overlapping phage cDNA clones (black bars) and 5' -RACE-PCR product (R1) spanning 10.66 kb of the SCA1 transcript is shown. cDNA clone 31-5 contains the entire coding region for the SCA1 gene product, ataxin-1. On top, a schematic shows the structure of the SCA1 transcript; the sizes of the coding region (rectangle) as well as the 5'UTR and the 3'UTR (thin lines) are indicated. The position of the CAG repeat within the coding region is also shown. An asterisk indicates the clones used as probes to screen the cDNA libraries. At the bottom the positions of BamHi (B), HindIII (H), and TaqI (T) restriction sites are shown.

Three cDNA libraries were screened: a human fetal brain library from Stratagene (La Jolla, Calif.), a human fetal brain library constructed in λ-Zap II with the inserts cloned into the Not1 restriction site (provided by Dr. Cheng Chi Lee at Baylor College of Medicine), and an adult cerebellar cDNA library from Clonetech (Palo Alto, Calif.). The libraries were plated on 150 cm plates at a density of 50,000 pfu per plate using bacterial strain LE392 (ATCC number 33572). Hybond-N filters (Amersham, Arlington Heights, Ill.) were used to carry out plaque lifts. The fragments used as probes in the first screening included a mixture of two polymerase chain reaction (PCR) products obtained by using the primers Rep1 and Rep2 (FIG. 3) immediately flanking the repeat and the primers Pre1 and Pre2 (FIG. 3) (SEQ ID NO:2), (SEQ ID NO:3), (SEQ ID NO:4), (SEQ ID NO:5), (SEQ ID NO:6) which amplify a sequence immediately adjacent to the repeat, and a 1.1 kb subclone of the 3.36-kb EcoRI fragment (FIG. 1) (SEQ ID NO:1). The 1.1 kb fragment (C208-1.1) is located 540 bp 3' to the CAG repeat. A 9-kb EcoRI genomic fragment derived from the same cosmids containing the CAG repeat was also used in this screening. Subsequent rounds of screening were carried out on the same libraries using as probes cDNA clones 31-5, 3J, 3c7-2 and 3c7 (FIG. 13). Genomic and cDNA probes were labeled using the random priming technique described in A. P. Feinberg et al., *Anal. Biochem.,* 137, 266–267 (1984). Repetitive sequences were blocked as described in P. G. Sealy et al., *Nucl. Acids Res.,* 13, 1905–1922 (1985). Briefly, the probes were reassociated with a large excess of shear human placental DNA. The nonrepetitive regions remained single-stranded and no separation of the single-stranded fragments from the reassociated fragments was necessary in order to allow the signal from low copy number components to be detected in subsequent transfer hybridizations. Hybridization of the filters was then carried out following standard protocols as described in H. Y. Zoghbi, et al., *Am. J. Hum. Genet.,* 42, 877–883 (1988).

2. DNA Sequencing and Sequence Analysis.

Shotgun libraries were constructed in M13 as described in A. T. Bankier, et al., *Meth. Enzvmol.,* 155, 55–93 (1987) for each of the following cDNA clones: 8-8, 31-5, 3c5, 3c7-1, 3J, 3c7-2, 3c7 (FIG. 13). Twenty to thirty M13 subclones were sequenced for each CDNA clone using an Applied Biosystem, ABI 370A, automated fluorescent sequencer, as described in R. Gibbs, et al., *Proc. Natl. Acad. Sci. U.S.A.,* 86, 1919–1923 (1989). Some cDNA clones (8-9*b,* 8-9*a,* AX1, B21, B11, 3c28) were partially sequenced manually using a Sequenase sequencing kit (USB, Cleveland, Ohio) on double-stranded templates, according to the manufacturer's recommendations. The sequence coverage in terms of numbers of cDNA/genomic clones analyzed was 3-4X in the coding and 5'UTR and 2X in the 3 'UTR. All RT-PCR, 5'-RACE-PCR and inverse-PCR products were sequenced manually after subcloning into SmaI-digested pBluescript SK-plasmid (Stratagene, La Jolla, Calif.) modified using the T-vector protocol as described in D. Marchuk et al., *Nucl. Acids Res.,* 19, 1154 (1990). Use of this protocol facilitates cloning. Briefly, Taq polymerase ordinarily causes a template-independent addition of adenosine at the 3' end of the PCR product, making blunt end ligations difficult. In the T-vector protocol, a thymidine is added to the 3' end of a digested plasmid. The result is a one-base sticky end complementary to the 3' adenosine in the PCR product, which greatly increases cloning efficiency.

Data base searches were carried out using the GCG software package (Genetics Computer Group, Madison, Wis.) and the BLAST network service from the National Center for Bioteclnology Information (S. F. Altschul, et al., *J. Mol. Biol.,* 215, 403–410 (1990)). The sequence of the SCA1 transcript has been deposited in Gcnbank, accession number X79204.

3. Northern Blot, RT-PCR and Genomic PCR Analyses.

The northern blot of poly-$(A)^+$ RNA from various human tissues and the poly-$(A)^+$ RNA from adult human cerebellum were purchased from Cloneteclh (Palo Alto, Calif). Poly-$(A)^+$ RNA from human lymphoblastoid cells was prepared by first extracting total RNA using guanidinium thiocyanate, followed by centrifugation in a cesium chloride gradient (P. Chomczynski et al., *Anal. Biochem.,* 162, 156–159 (1987)). Poly-$(A)^+$ RNA was selected using Dynabeads oligo $(dT)_{25}$ from Dynal (Great Neck, N.Y.). First strand randomly primed cDNA synthesis was carried out using MMLV (murine maloney leukemia virus) reverse transcriptase (BRL, Gaithersberg, Md.). This was conducted in a 20 $\mu$l reaction mixture containing 3 $\mu$g RNA, first strand buffer (50 mM Tris-HC1, pH 8.3, 75 mM KC1, 3 mM Mg $C1_2$), (BRL, Gaithersberg, Md.), 10 mM dithiothreitol (BRL, Gaithersberg, Md.), 1 $\mu$M 3' end primer, 0.5 units RNasin (Promega, Madison, Wis.), 5.0 units MMLV reverse transcriptase (BRL, Gaithersberg, Md.), 250 $\mu$M each deoxynucleotide triphospate: dGTP, dATP, dCTP, dTTP. The mixture was incubated for 20 minutes at 37° C. then put on ice. A 10 $\mu$l aliquot was used for the PCR reaction. First strand randomly primed cDNA from human brain, liver and adrenal were provided by Dr. G. Borsani (Baylor College of Medicine).

RT-PCR for detection of alternative splicing was carried out with primers 9b and 5R and with primers 5F and 5R (FIG. 15) (SEQ ID NO:8) (SEQ ID NO:9) under the following conditions: an initial denaturation step at 94° C. for 5' followed by 30 cycles of 94° C. for 1 minute, 60° C. for 1 minute and 72° C. for 2 minutes. The reaction mixture contained 10 $\mu$l cDNA, PCR buffer (50 mM KCL, 10 mM Tris-HC1, pH 8.3, 1.25 mM $MgCl_2$), 1 $\mu$M of the relevant 3' primer (primer 5R), 2% formamide and 1.25 units Amplitaq enzyme (Perkin Elmer, Norwalk, Conn.).

RT-PCR on lymphoblastoid cell lines with primers Rep1 and Rep2 for detection of expression of SCA1 mRNA was carried out using "hot start" PCR with three cycles of: 97° C. for 1 minute, 57° C. for 1 minute and 72° C. for 1 minute. Following that 33 cycles of 94° C. for 1 minute, 55° C. for 1 minute and 72° C. for 1 minute were carried out. Twenty microliters of the PCR reactions was then resolved on a 2% agarose gel (2 g Ultrapure agarose (BRL, Gaithersberg, Md.) in 40 mM Tris-acetate, 1 mM EDTA, pH 8.0) and blotted onto Sureblot membrane (Oncor, Gaithersburg, Md.). The filter was hybridized with a $(GCT)_7$ (SEQ ID NO:66) oligonucleotide end-labeled with $\gamma$-$^{32}$P-ATP. Hybridizations were done in a solution of 1 M NaCl, 1% sodium dodecyl sulfate (SDS) (Sigma Chemical Company, St. Louis, Mo.) and 10% (w/v) dextran sulphate (Sigma Chemical Company, St. Louis, Mo.). Filters were washed in 2×SSC (1×SSC is 0.15 M sodium chloride and 0.015 M sodium citrate), and 0.1% SDS at room temperature for 15 minutes, followed by a 15 minute wash at room temperature in a solution pre-warmed to 67° C.

B. Results

Figure 14:
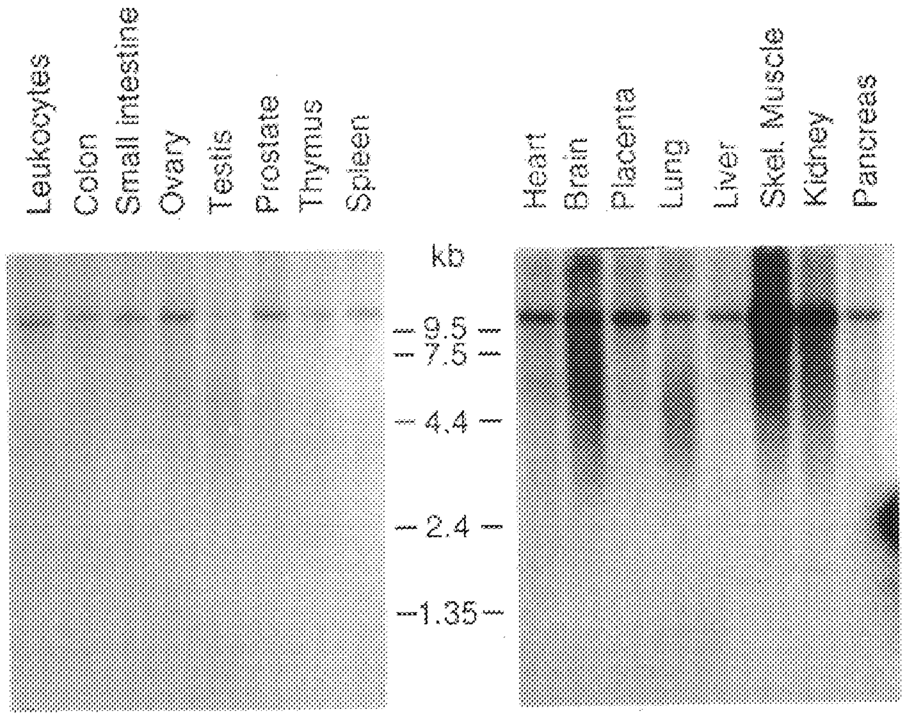
FIG. 14. Northern blot analysis of the SCA1 gene using RNAs from multiple human tissues. The panel on the left is probed with a PCR product from a portion of the coding region (bp 2460 to bp 3432). The panel on the right is hybridized with the 3J cDNA clone from the 3'UTR. An ~11 kb transcript is detected in RNAs from all tissues using both probes as well as the cDNA clones 31-5 and 8-8, both of which contain the CAG repeat (FIG. 13).

Two human fetal brain cDNA libraries were screened using as probes various DNA fragments from the cosmid clone shown to contain the CAG repeat. Five cDNA clones were identified; these included clone 31-5 containing the CAG repeat, and clone 3J which was found not to overlap with 31-5 (FIG. 13). Northern blot analysis revealed that clones 31-5 and 3J identified the same 11-kb transcript detectable in all tissues examined (FIG. 14). Accordingly, the same two human fetal brain cDNA libraries and a human adult cerebellar cDNA library were used for several rounds of screening in order to obtain the full length transcript. As a result, 22 cDNA clones were isolated and characterized by sequence and PCR analyses to assemble a contig spanning the SCA1 transcript. Twelve of the phage clones spanning the cDNA contig are shown in FIG. 13. These clones were sequenced allowing the assembly of the entire sequence of the SCA1 cDNA which spans 10,660 bp (FIG. 15) (SEQ ID NO:9).

Sequence analysis revealed a coding region of 2448 bp starting with a putative ATG initiator codon at base 936 located within a nucleotide sequence that fulfills Kozak's criteria for an initiation codon (M. Kozak, *J. Cell. Biol.,* 108, 229–241 (1989)). An in-frame stop codon is present 57 bp upstream of that ATG in three independent cDNA clones as well as in genomic DNA. Furthermore, both the ATG at the beginning of the coding region and the upstream stop codon have been found in the murine homologue of SCA1 in the murine fetal brain library (Stratagene, La Jolla, Calif.). The SCA1 gene therefore encodes a polypeptide of about 816 amino acids, with an expected size of 87 kD, designated ataxin-1. However, one cannot exclude the possibility that the coding region begins at any of the other ATGs, located downstream of the first methionine, which would result in a smaller protein.

The CAG repeat is located within the coding region 588 bp from the first methionine and encodes a polyglutamine tract. The open reading frame ends with a TAG stop codon at base 3384. Therefore, this transcript has a 5' untranslated region (5'UTR) of 935 bp and a 3' untranslated region (3'UTR) of 7277 bp. The transcript ends with a tail of 57 adenosine residues; a polyadenylation signal, AATAAA, is found 23 nucleotides upstream of the poly(A) tail. Homology searches using both the DNA sequence of the coding region and the predicted protein sequence (lacking the CAG repeat and the polyglutamine tract, respectively) revealed no significant homology with other known proteins in the data base. Analysis of the sequence of ataxin-1 failed to reveal the presence of any strong phosphorylation sites as well as any specific motifs such as DNA binding or RNA binding domains. The putative secondary structure of this protein is compatible with that of a soluble protein as no hydrophobic domains were identified. A DNA sequence data base search revealed an identity between 380 bp in the 3'UTR of the SCA1 transcript and an expressed sequence tag (EST04379) isolated from a human fetal brain cDNA library (M. D. Adams, M.D. et al., *Nature Genet.,* 4, 256–267 (1993)).

V. Organization of the SCA1 Transcript: Evidence for Alternative Splicing in the 5'UTR A. Methods 1. 5'-RACE-PCR First strand cDNA was prepared from 1 mg of poly-(A) $^+$RNA from human adult cerebellum (Clonetech, Palo Alto, Calif.) using the primer 5R (FIG. 15) as described in Example IV. 5'-RACE-PCR was carried out as described in M. A. Frohman in *PCR Protocols. A Guide to Methods and Applications;* M. A. Innis, et al., Eds.; Academic Press: San Diego (1990) using SCA1 primers 5a and X4-1 Table 9) as specific primers. The product was then electrophoresed through a 1.2% agarose gel, blotted onto SureBlot hybridization membrane (Oncor, Gaithersburg, Md.) as described in Example II above, and then, to test the specificity of the product, hybridized to a SCA1 specific probe represented by a PCR product spanning 118 bp between primer 9b in exon 1 and primer X3-1 (Table 9) in exon 3.

TABLE 9

Primer sequences for inverse-PCR

| Exon | Primer 1 | Primer 2 |
|---|---|---|
| 2 | X2-1 (181–164) (SEQ ID NO: 67) GTAGTAGTTTTTGTGAGG | X2-2 (185–203) (SEQ ID NO: 68) CACCAAGCTCCCTGATGGA |
| 3 | X3-1 (246–229) (SEQ ID NO: 69) GCTTGAATGGACCACCCT | X3-2 (277–296) (SEQ ID NO: 70) ATCTCCTCCTCCACTGCCAC |
| 4 | X4-1 (347–329) (SEQ ID NO: 71) AGACTCTTTCACTATGCTC | X4-4 (407–425) (SEQ ID NO: 72) TTCAGCCTGCACGGATGGT |
| 5 | 5a (482–463) (SEQ ID NO: 73) TGGCAGTGGAGAATCTCAGT | 5-2 (519–538) (SEQ ID NO: 74) TGCTGCAAGGAACTGATAGC |
| 6 | 10a (598–580) (SEQ ID NO: 75) AATGGTCTAATTTCTTTGG | 10b (607–625) (SEQ ID NO: 76) GAGAAAGAAATCGACGTGC |
| 7 | 6-1 (714–695) (SEQ ID NO: 77) ACAGGCTCTGGAGGGCTCCT | X5-2 (723–742) (SEQ ID NO: 78) TCCATGGTGAAGTATAGGCT |
| 9 | 9-1 (2919–2900) (SEQ ID NO: 79) AGCAGGATGACCAGCCCTGT | 9-2 (2939–2957) (SEQ ID NO: 80) GCTCTTTGATTTQCCGTGT |

All primers are read in the 5' to the 3' direction. Numbers in parenthesis represent the coordinates of each prirner within the SCA1 cDNA sequence (FIG. 15).

B. Results

Figure 16A:
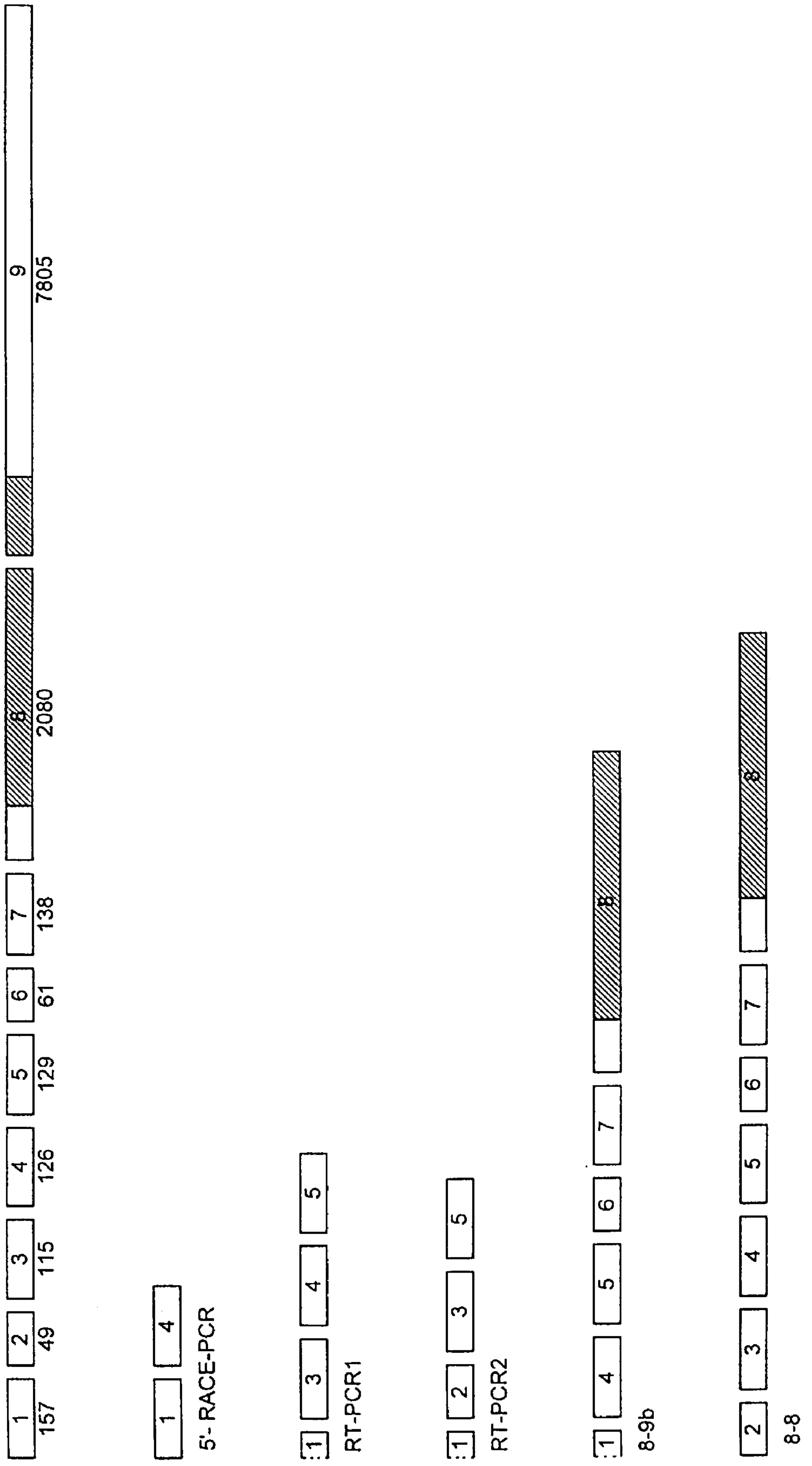
FIGS. 16A and 16B. a. The structure of the SCA1 transcript and the various splice variants. The schematic on top represents the nine exons (not drawn to scale) and their respective sizes. The stippled areas indicate the coding region. The structure of five cDNA clones representing different splice variants of the SCA1 transcript are also shown. Clones 8-8 and 8-9b are phage clones, RT-PCR1 and RT-PCR2 are two clones obtained by RT-PCR carried out on cerebellar poly-(A)+ RNA using the primers 9b and 5R (FIG. 15). Only 30 bp of exon 1 were present in clone 8-9b and RT-PCR products as indicated by the broken line in the rectangles. b. Detection of alternative splicing of the SCA1 transcript in cerebellar poly-(A)+ RNA (CBL RNA). RT-PCR analysis was carried out using two sets of primers: 9b-5R and 5F-5R. PCR products of the expected size were detected in CBL RNA in the presence of reverse transcriptase (+RT) with both pairs of primers. Using the 9b-5R pair at least two larger PCR products were also detected. Using the 5F-5R pair for RT-PCR at annealing T<60°, some faint bands in the same size range as those seen using the 9b-5R primer pair were also seen. 8-8 and 8-9b are the phage clones used as positive controls. The sizes of the relevant bands of the molecular weight marker (FX174 cut with HaeIII) are indicated on the left.

To characterize the genomic region flanking the CAG repeat, the 3.36-kb EcoRI genomic fragment known to contain this repeat was completely sequenced. Alignment of this genomic sequence with the cDNA sequence allowed us to determine that the 3.36-kb EcoRI fragment contains a 2080-bp exon which has 160 bp of 5'UTR, the first potential initiation codon and the first 1920 bp of the coding region. The rest of the coding region lies within the next downstream exon as detected by PCR analysis on genomic DNA. The last coding exon, which maps to a 9-kb EcoRI fragment in genomic DNA also contains 7277 bp of 3'UTR for a total length of 7805 bp (FIG. 16*a*).

Evidence for alternative splicing in the 5'UTR was initially suggested based on the hybridization pattern of the two most 5'cDNA clones, 8-8 and 8-9b (FIG. 13) to Southern blots containing EcoRI-digested genomic DNA from total human DNA and YACs spanning the SCA1 region. At least three strongly hybridizing fragments in addition to the 3.36-kb EcoRI fragment were seen. As neither of the cDNA clones contains an EcoRI site, this result suggested the presence of several exons in the 5'UTR of the SCA1 transcript. Given these data and the unusual length of the 5'UTR, this region was characterized in more detail.

Figure 16B:
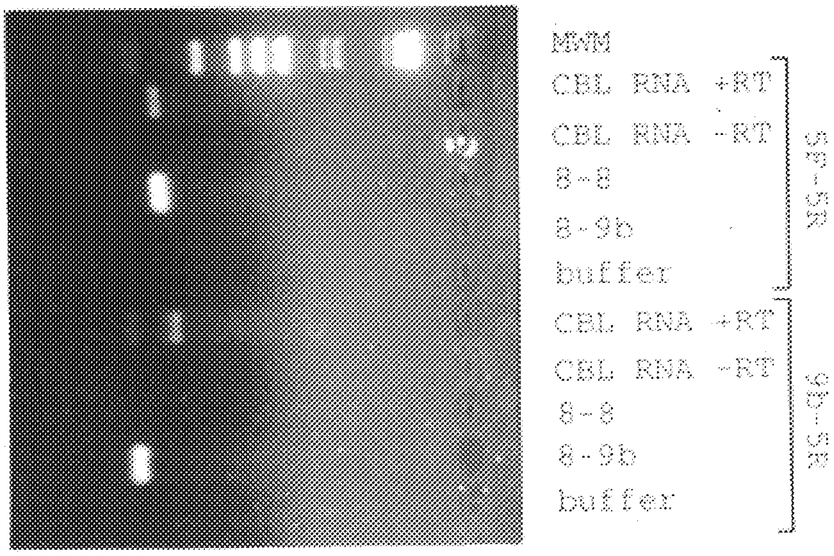

Alignment analysis of the sequence of clones 8-8 and 8-9b revealed the presence of two different 5' sequences diverging at basepair 322. This result was highly suggestive of alternative splicing. In order to test this hypothesis, reverse transcription-PCR (RT-PCR) was performed on mRNA from cerebellar tissue using the primers indicated in FIG. 15. When the primers 9b (specific for 8-9b clone) and 5R (present in both clones) were used in the RT-PCR analysis three products were obtained: one of the expected size (246 bp) and at least two fragments of larger size (FIG. 16*b*). The same result was obtained when RT-PCR was carried out on liver, adrenal, brain and lymphoblast cDNAs. The various RT-PCR products were cloned and sequenced. Sequence analysis of all these products and comparison with the sequence of phage clones 8-8 and 8-9b confirmed that they were the result of alternative splicing. FIG. 16*a* shows the structure of all the cDNA clones which contain the 5' exons of the SCA1 gene and depicts the splice variants. Based on sequence analysis of three cDNA clones and characterization of cerebellar RT-PCR products, five exons (exons 1 through 5) were identified and their borders in the transcript were determined. Exons 2, 3 and 4 are alternatively spliced in the clones examined and in cerebellar tissue, whereas exon 5 was present in all the cDNA clones and RT-PCR products.

Rescreening of cDNA libraries with clones 8-8 and 8-9b as probes did not yield any additional cDNA clones. To identify additional alternatively spliced exons in the 5' UTR and to confirm initial results, 5'-RACE-PCR was carried out on reverse transcribed cerebellar mRNA using primers from the 5' end of exons 5 and 4. A 218-bp product was identified and its specificity was confirmed by Southern analysis using an internal PCR product as probe. Sequence analysis of the 5'-RACE-PCR product, furthermore, confirmed the alternative splicing of two exons (2 and 3) and allowed the identification of an additional 127 bp at the 5' end of this gene (FIG. 16*a*).

VI. Identification of Intron-Exon Boundaries and Determination of the Genomic Structure of SCA1

A. Methods

1. Identification of Intron-Exon Boundaries

The boundaries of exons 2–9 were identified by inverse-PCR.To carry out inverse-PCR, YAC agarose plugs were digested to completion as described in M. C. Wapenaar, et al., *Hum. Mol. Genet.,* 2, 947–952 (1993) using frequent-cutter restriction enzymes such as Sau3al, TaqI, HaeIII and MspI purchased from Boehringer Mannheim Biochemicals (Indianapolis, Ind.) and used as recommended by the manufacturer. The plugs were then digested with β agarase I (USB, Cleveland, Ohio) following the manufacturer's recommendations and subsequently phenol-chloroform (Boehringer Mannheim Biochemicals, Indianapolis, Ind.) extracted, precipitated with ethanol and resuspended in 12 ml of TE (TE: 10 mM Tris-HC1, 1 mM EDTA) pH 8. Fifty ng of DNA from each digest was then circularized according to the published protocol of J. Groden et al., *Cell,* 66, 589–600 (1991). Diverging PCR primers were designed within the cDNA and used on the circularized product under the amplification conditions described in J. Groden et al., *Cell,* 66, 589–600 (1991). PCR products were then subcloned and sequenced as described in Example II, above.

Inverse-PCR identified all intron/exon boundaries except the boundary of exon 1. Accordingly, a 9-kb EcoRI genomic fragment found to contain exon 1 was subcloned from a cosmid derived from YAC 227B1. (Example II). This subclone was subsequently partially sequenced to identify the boundary of exon 1.

2. Mapping of cDNA Clones to the YACs and Cosmids.

Southern blots containing EcoRI-digested DNAs from YACs spanning the SCA1 critical region as well as Southern blots containing DNAs from the YACs digested with rare-cutter enzymes (see previous section) were hybridized, using the standard protocol described in H. Y. Zoghbi et al., *Am. J. Hum. Genet.,* 42, 877–883 (1988), to various SCA1 cDNA clones and to all the genomic fragments containing the intron-exon boundaries. Briefly, restriction fragments were separated by electrophoresis on 0.7% agarose gels, denatured and transferred to Nytran (Schliecher and Schuell, Keene, NH) filters. Probes were $_{32}$P-labeled using the oligohexamer labeling method (A. P. Feinberg et al, *Anal. Biochem.,* 132, 6–13 (1983)). After hybridization the filters were washed and autoradiography was performed, as described in Zoghbi et al., *Am. J. Hum. Genet.,* 42, 877–883 (1988).

B. Results

Complete sequencing of the 3.36-kb EcoRI fragment provided the intron-exon boundaries for the 2080-bp exon containing most of the coding region (FIG. 17). In order to determine the actual number of exons and to obtain all of the intron-exon boundaries, an inverse-PCR strategy was adopted using two overlapping YAC clones, 227B1 and 149H3, known not to contain any rearrangements (see Example II). A total of nine exons, seven of which are in the 5'UTR, were identified and splice junctions for exons 1 through 9 were subcloned and sequenced (FIG. 17). The schematic on top of FIG. 16*a* shows the nine exons and their respective sizes. In the 5' untranslated region, alternative splicing involves exons 2, 3 and 4, but not exons 5, 6 and 7 in over 5 phage cDNA clones analyzed. The putative exon 1 encompasses 157 bp and hybridizes very strongly to an EcoRI fragment derived from hamster genomic DNA.

To study the genomic organization of the SCA1 gene, ten cDNA clones as well as genomic fragments containing the splice junctions for all the exons were mapped by Southern analysis and localized on a long range restriction map of four overlapping YAC clones spanning the SCA1 critical region (FIG. 18). This analysis revealed that the gene spans at least 450 kb of genomic DNA and that the putative first exon maps to a genomic fragment containing a hypomethylated CpG island. Detailed restriction analysis of the intron between the two coding exons (8 and 9) revealed that this intron is approximately 4.5-kb in length. The sizes of the remaining introns were estimated from the long range restriction map and by PCR analysis and ranged from 650 bp (intron 2) to nearly 200 kb (intron 7) (FIG. 18).

VII. Expression of the SCA1 mRNA in SCA1 Patients

Figure 19:
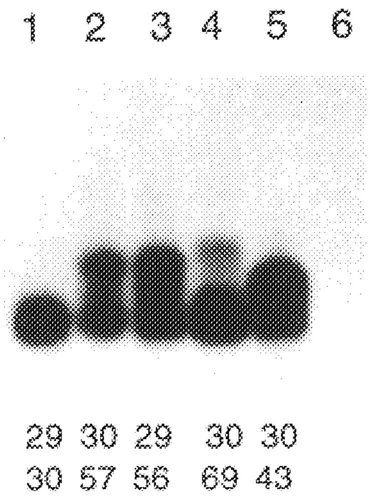
FIG. 19. Analysis of expression of the expanded SCA1 allele. RT-PCR was carried out on lymphoblast poly-$(A)^+$ RNA from one unaffected individual (lane 1) and four SCA1 patients (lanes 2 through 5) using primers Rep1 and Rep2. This analysis shows that both the normal and the expanded SCA1 alleles re transcribed. The number of the repeat units for each allele is indicated below each lane; lane 6 is the RT minus control.

As a first step toward understanding the mechanism by which the expansion of a trinucleotide CAG repeat leads to neurodegeneration in SCA1, the level of transcription of SCA1 from the expanded alleles in patients was investigated. RT-PCR was carried out with primers Rep1 and Rep 2 which flank the CAG repeat as described in Example V using lymphoblastoid mRNAs from SCA1 patients with repeat sizes ranging from 43 to 69. This analysis revealed that mRNA was expressed from both the normal allele and the expanded allele (FIG. 19).

VIII. Cloning of Portions of the SCA1 Gene into the pMAL™-2 Vector

DNA from the SCA1 gene was cloned into the pMAL™-c2 vector (New England Biolabs, Beverly, Mass.), which produces a chimeric protein consisting the maltose-binding protein fused to the N-terminus of the protein of interest (ataxin-1) in a linkage that can subsequently be conveniently cleaved. To obtain DNA for cloning, SCA1 DNA was amplified and isolated clone 31-5 (FIG. 13) using standard PCR techniques. The manufacturer's instructions were followed in designing the appropriate oligonucleotide primers (pMAL™ vector Package Insert, 1992 New England Biolabs, revised Apr. 4, 1992). In each case an EcoRI linker site was designed into the 5' primer and a HindIII linker site was designed into the 3' primer to facilitate cloning. Three different amplification products were obtained. In one, DNA was isolated utilizing two 20-mer PCR primers COD and RCOD (Table 10) that hybridized to the 5' and 3' ends of the coding regions, such that the stretch of DNA being amplified contained residues presumed to encode the entire sequence of ataxin-1, beginning with Met1 and ending with Lys 817 (FIG. 15) (SEQ ID NO:8) (SEQ ID NO:9). The amplified product was than cloned into the EcoRI/HindIII site in the polylinker region of in pMAL™-c2 following instructions provided by the manufacturer. Two other constructs were made in the same way using PCR to isolate shorter segments of DNA. In both cases the same 3' end primer was used, but different 5' primers were employed (Table 10). One 5' primer (3COD) was designed such that the amplified product began at Met277 (the fourth methionine in the coding region), the other 5' primer (8COD) such that the amplified product began at Met548. pMAL™-c2 was transformed into competent cells containing a lacZΔM15 allele for α-complementation and cultured as recommended by the manufacturer.

TABLE 10

Primers for Cloning Into pMal Vector

| Primer Name | Nucleotide Sequence |
|---|---|
| COD | TGT GAA TTC ATG AAA TCC AAC CAA GAG CG (SEQ ID NO: 81) |
| 3COD | TGT GAA TTC ATG ATG CCA CAC ACG CTC AC (SEQ ID NO: 82) |
| 8COD | TGT GAA TTC ATG GTG CAG GCC CAG ATC (SEQ ID NO: 83) |
| RCOD | TTC GAA GCT TCT ACT TGC CTA CAT TAG AC (SEQ ID NO: 84) |

IX. Expression of Ataxin-1, Design of Antigenic Peptides and Production of Antibodies The fusion protein expressed by the constructs in Example VII were purified as directed by the manufacturer using affinity chromatography (pMAL™ vector Package Insert, 1992 New England Biolabs, revised Apr. 4, 1992). The purified protein was electrophoresed using 8% SDS polyacrylamide electrophoresis and electroeluted. The best expression (about 27 mg from 1 L of cells) was obtained from the shortest construct, but all constructs produced measurable levels of protein of a size consistent with their respective cloned gene product.

Antibody response in rabbits was initiated using the multiple antigenic peptide strategy of V. Mehra et al., *Proc. Natl. Acad. Sci. USA,* 83, 7013–7017 (1986). In addition to the three electroeluted cloned gene products described in the preceding paragraph, three synthetic peptides were used as well. The synthetic peptides used were Peptide A (amino acids 4 through 18), Peptide B (amino acids 162 through 176) and Peptide C (amino acids 774 through 788). These peptides were chosen such that they showed little or no homology with other known short amino acid stretches in proteins and also such that they contained proline, which makes it more likely that these fragments are located on the surface of the protein, thus making it more likely that antibodies to the fragments will react with the whole protein as well.

Immunoglobulin (IgG) from rabbit blood was purified, and antibody/antigen results were analyzed using Western blots as described in Gershoni et al., *Anal. Bioch.,* 131, 1–15 (1983). IgG from rabbits injected with the cloned gene products and the synthetic sequences were found to hybridize to their respective antigens. The anti-sera from rabbits immunized with the 8COD-RCOD gene product (i.e., the ataxin-1 fragment spanning residues 548 through 817) hybridized with a protein of the expected size in brain tissue extracts from mouse, rats, and humans. A similar size protein has also been detected using lymphoblasts. This hybridization is blocked by preincubation with the polypeptide antigen, and not blocked by unrelated antigens. In particular, antibodies raised against Peptide C are blocked by either Peptide C or the short gene product.

X. Molecular and Clinical Correlations in Spinocerebellar Ataxia Type 1 (SCA1)

A. Materials and Methods

1. Family Material

Members representing 87 kindreds with dominantly inherited ataxia were evaluated. Nine kindreds of diverse ethnic background (Caucasian American, African American, South African, Siberian Iakut) were already known to have SCA1 based on linkage to the HLA locus and to D6S89 on chromosome 6p. Genotypic analysis of the SCA1 CAG repeat was carried out on all nine kindreds to determine if all known SCA1 families had the same mutational mechanism involving repeat expansion. Most of the study participants were personally examined. The affected status was always confirmed by a neurologist, but the age of onset was based on historical information from the patient and/or other family members. Severity of disease was measured by the age at death minus the age of onset. Detailed characterization of the repeat variability was carried out for all nine kindreds. To identify additional kindreds with a CAG expansion at the SCA1 locus, affected individuals from 78 newly identified families with dominantly inherited ataxia were clinically examined. Blood was collected from at least one affected individual from each of these kindreds and screened by DNA analysis for the presence of a CAG repeat size within the expanded range ($\geqq$42 repeats). Although there was no evidence that these 78 individuals are related, there is a chance that some of the affected patients come from the same families.

To assess the distribution of CAG repeat sizes on normal chromosomes further, the number of CAG repeats was determined for 304 normal chromosomes from unrelated individuals of various ethnic backgrounds.

2. Molecular Studies

Blood samples were used to establish lymphoblastoid cell lines by Epstein-Barr virus transformation. Genomic DNA was isolated either directly from venous blood or from lymphoblastoid cell lines. Blood samples were collected from these patients over an 8-year period, during which time 29 patients died. PCR reactions were performed using the Rep1 (TTGACCTTTACACCTGCAT) (SEQ ID NO:85) and Rep2 (CAACATGGGCAGTCTGAG) (SEQ ID NO:27) primers. Fifty nanograms of genomic DNA was mixed with 5 pmol of each primer in a total volume of 20 $\mu$l containing 1.25 mM $MgCl_2$, 250 uM dNTPs, 50 mM KC1, 2% formamide, 10 mM Tris-HCl pH 8.3 and 1 unit ampliTaq (Perkin-Elmer/Cetus). The Rep1 primer was labelled at the 5' end with [$\gamma$-$^{32}$P]ATP. Samples were denatured at 94° C. for 4 minutes, followed by 30 cycles of denaturation (94° C., 1 minute), annealing (55° C., 1 minute) and extension (72° C., 2 minutes). Six $\mu$l of each PCR reaction was mixed with 4 $\mu$l formamide loading buffer, denatured at 90° C. for 2 minutes, and electrophoresed through a 6% polyacrylamide/7.65 M urea DNA sequencing gel. Allele sizes were determined by comparing migration relative to an M13 sequencing ladder.

3. Statistical Analyses

The relationship between age of onset and CAG repeat number on both the affected and the normal chromosomes of patients was evaluated through linear regression analyses. Similarly, the relationship between repeat length and duration of disease was quantified. Ages of onset were used directly in these analyses, but also following logarithmic and square root transformation. Although the latter transformation provided the best approximation to a normal distribution, results obtained were consistent between analyses before and after transformation. Analysis of variance was performed to detect differences among the families in the mean age of onset, after correction for the effect of the CAG repeat number on age of onset. In addition, the sex of the transmitting parent was included as a possible explanatory variable for variations in age of onset. All regression and variance analyses were carried out with the SPSS package of computer programs, versions 4.0.1.

B. Results

1. Family Studies

All affected individuals from the nine known SCA1 kindreds had an expanded trinucleotide repeat on one of their alleles. No repeat expansions were observed among eight kindreds previously shown by linkage analyses not to be SCA1. These eight kindreds were examined for the SCA1 gene expansion to confirm the linkage results.

Among the 70 other dominant ataxia families analyzed, three (4%) were found to have an expanded CAG repeat on one of the SCA1 alleles. Of all of the dominant kindreds studied, 12 of 87 (14%) have an expanded CAG repeat at the SCA1 locus. While the sample size is relatively small, and both estimates are arguably biased to exclude or select for SCA1 kindreds, expanded CAG repeat tracts within the SCA1 gene clearly account for only a small fraction of this complex group of diseases. The distribution of the CAG repeat number from normal controls and from ataxic individuals that did not have an expansion were similar (data not shown). These data argue against the involvement of the CAG repeat at the SCA1 locus in these families. However, it is still possible that some of these small families have other mutations at the SCA1 locus.

The typical clinical findings in the genetically proven SCA1 kindreds were gait and limb ataxia, dysarthria, pyramidal tract signs (spasticity, hyperreflexia, extensor plantar responses) and variable degrees of occulomotor findings which include one or more of the following: nystagmus, slow saccades, and opthalmoparesis. In the later stages of the disease course, bulbar findings consistent with dysfunction of cranial nerves IX, X, and XII became evident. Also, dystonic posturing and involuntary movements including choreoathetosis became apparent in the later stages of the disease. Motor weakness, amyotrophy, and mild sensory deficits manifested as propioceptive loss were also detected. Although ataxia, dysarthria and cranial nerve dysfunction were consistently present in every SCA1 affected individual, considerable intrafamilial variability was noted with regard to all of the other clinical features. Juvenile onset (≦18 years) was observed in four kindreds. Of interest is the finding that juvenile onset cases typically inherited the disease gene from an affected father. Several of the kindreds that did not have an expanded SCA1 CAG repeat, displayed the same clinical findings as those observed in SCA1 kindreds confirming the inherent difficulty in clinically classifying this group of disorders. While it is possible that some of these kindreds have other mutations at the SCA1 locus, the disease locus (loci) for eight of these families has also been excluded from the SCA1 region by linkage analyses.

2. Repeat Analysis on Normal and SCA1 Chromosomes

Figure 20:
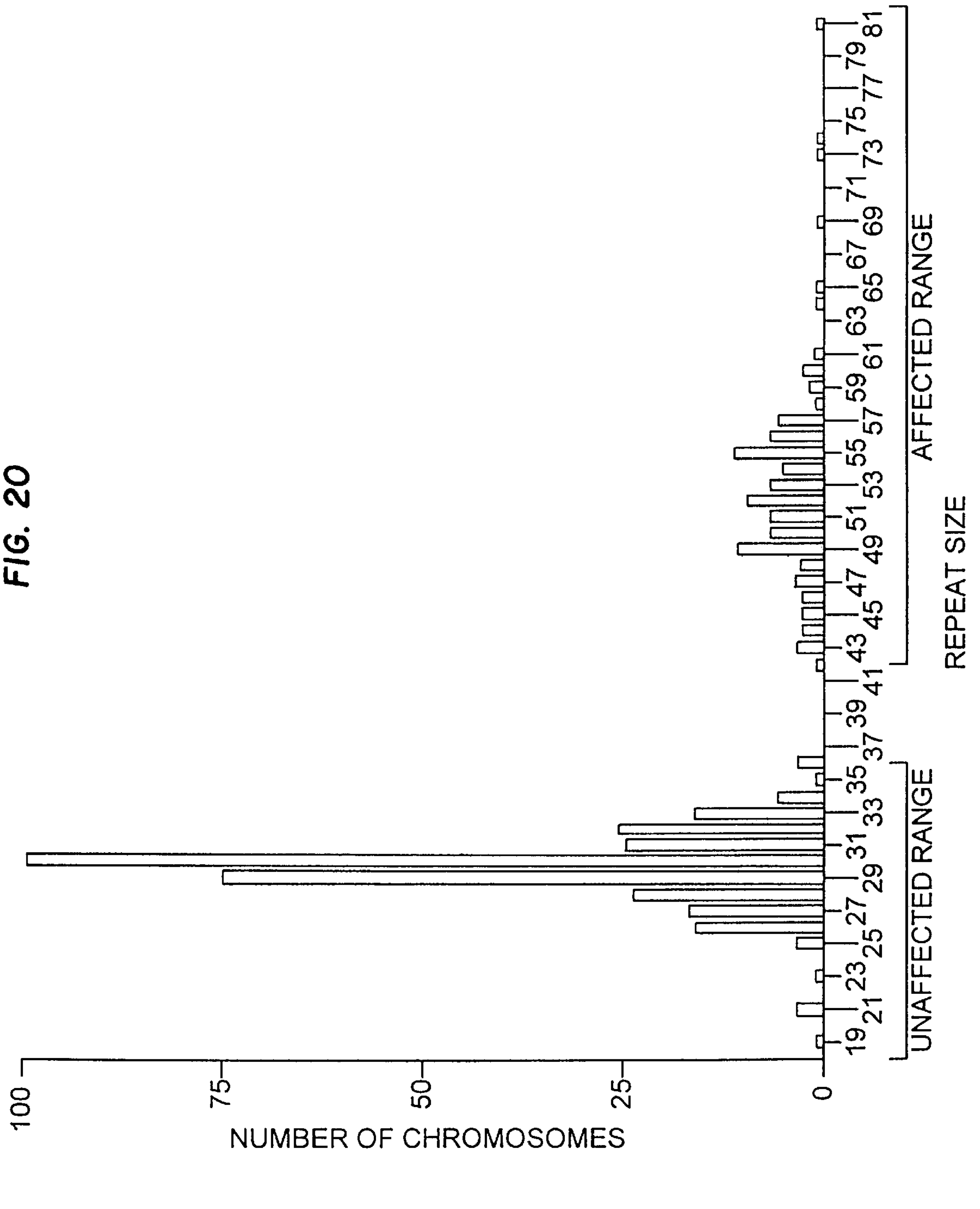
FIG. 20. Distributions of CAG repeat lengths from unaffected control individuals and from SCA1 alleles. Normal alleles range in size from 19 to 36 repeat units while disease alleles contain from 42 to 81 repeats.

FIG. 20 shows the size distribution of the CAG repeats on 304 chromosomes from unaffected control individuals who are at risk for ataxia, and 113 expanded alleles from individuals affected with the disease. The normal alleles range in size from 19 to 36 CAG repeat units. Over 95% of the normal alleles contain from 25 to 33 CAG repeat units, the majority (65%) of which contain 28 to 30 repeats. The mean repeat size on normal chromosomes for the African Americans, Caucasian, and South African populations are very similar with 29.1, 29.8, and 29.4 CAG repeat units, respectively. Combined heterozygostiy for the CAG repeat at the SCA1 locus was 0.809 for the populations examined, giving an overall polymorphism information content (P.I.C.) value of 0.787. No change in CAG repeat length was observed for 135 meioses of SCA1 alleles containing CAG repeat tracts within the normal range, i.e., all were inherited in a Mendelian fashion. In contrast, 41 of the 62 meioses involving expanded SCA1 alleles changed in repeat size. The rate of repeat instability for female meioses is 60% while the instability observed for males was 82%.

The number of CAG repeats found on SCA1 chromosomes from 113 affected individuals was always greater than the number of repeats on normal chromosomes, ranging from 42 to 81 with a means of 52.6 (FIG. 20).

All patents, patent documents, and publications cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method for identifying individuals at risk for developing spinocerebellar ataxia type 1 comprising the step of:

analyzing the CAG repeat region of a spinocerebellar ataxia type 1 gene wherein individuals at risk for developing spinocerebellar ataxia type 1 have greater than 36 CAG repeats in the CAG repeat region.

2. The method of claim 1 wherein individuals at risk for developing spinocerebellar ataxia type 1 have greater than 42 CAG repeats in the CAG repeat region.

3. The method of claim 1 wherein the analyzing step comprises the steps of:

performing a polymerase chain reaction with oligonucleotide primers capable of amplifying the CAG repeat region located within the spinocerebellar ataxia type 1 gene; and detecting amplified DNA fragments containing the CAG repeat region.

4. The method of claim 1 comprising the additional step of:

sequencing the CAG repeat region.

5. The method of claim 3 wherein the oligonucleotide primers are selected from the group consisting of: CCGGAGCCCTGCTGAGGT (SEQ ID NO:8), CCAGACGCCGGGACAC (SEQ ID NO:9), AACTGGAAATGTGGACGTAC (SEQ ID NO:10), CAACATGGGCAGTCTGAG (SEQ ID NO:1), CCACCACTCCATCCCAGC (SEQ ID NO:12), TGCTGGGCTGGTGGGGGG (SEQ ID NO:13), CTCTCGGCTTTCTTGGTG (SEQ ID NO:14), and GTACGTCCACATTTCCAGTT (SEQ ID NO:15).

6. A method for determining whether an individual is at risk for developing spinocerebellar ataxia type 1 comprising the step of:

analyzing the CAG repeat region of a spinocerebellar ataxia type 1 gene wherein individuals who are not at risk for developing spinocerebellar ataxia type 1 have less than or equal to 36 CAG repeats in the CAG repeat region and wherein the CAG repeat region contains no more than about 3 CAT trinucleotide repeats.

7. An isolated recombinant vector comprising bases 1026 to 1614 and bases 1614 to 3384 of SEQ ID NO:8 operatively linked to hetrologous vector sequences.

8. The isolated recombinant vector according to claim 7 wherein the vector is capable of expressing a polypeptide comprising amino acids 1 to 196 of SEQ ID NO:9 followed by a polyglutamine repeat region.

9. Cells containing the vector of claim 8.

10. An isolated nucleic acid fragment encoding the polypeptide for spinocerebellar ataxia type 1, wherein the polypeptide comprises amino acids 1 to 196 of SEQ ID NO:9 followed by a polyglutamine repeat region.

* * * * *

UNITED STATES PATENT AND TRADEMARK OFFICE

CERTIFICATE OF CORRECTION

PATENT NO. : 5,834,183
APPLICATION NO. : 08/267803
DATED : November 10, 1998
INVENTOR(S) : Orr et al.

It is certified that error appears in the above-identified patent and that said Letters Patent is hereby corrected as shown below:

Column 33, line 14, delete "B134B3", and insert --B172B3--;

Column 33, line 21, delete "aattctggagaggatgt" and insert --aattctggagagaggatgt--;

Column 33, line 35, delete "(6S339)", and insert --(D6S339)--;

Column 33, line 39, delete "55° C.";

Column 93, the sequence at SEQ ID NO:52 (~line 17), delete "aattctggagaggatgt" and insert --aattctggagagaggatgt--.

Column 105, line 49, delete "SEQ ID NO:8" and insert --SEQ ID NO:26--;

Column 105, line 50, delete "SEQ ID NO:9" and insert --SEQ ID NO:27--;

Column 105, line 51, delete "SEQ ID NO:10" and insert --SEQ ID NO:28--;

Column 105, line 52, delete "SEQ ID NO:1" and insert --SEQ ID NO:29--;

Column 105, line 53, delete "(SEQ ID NO:1)", and insert --(SEQ ID NO:11)--;

Column 106, line 25, delete "SEQ ID NO:12" and insert --SEQ ID NO:30--;

Column 106, line 26, delete "SEQ ID NO:13" and insert --SEQ ID NO:31--;

Column 106, line 27, delete "SEQ ID NO:14" and insert --SEQ ID NO:32--;

UNITED STATES PATENT AND TRADEMARK OFFICE

CERTIFICATE OF CORRECTION

PATENT NO. : 5,834,183
APPLICATION NO. : 08/267803
DATED : November 10, 1998
INVENTOR(S) : Orr et al.

It is certified that error appears in the above-identified patent and that said Letters Patent is hereby corrected as shown below:

Column 106, line 28, delete “SEQ ID NO:15” and insert --SEQ ID NO:33--.

Signed and Sealed this

Second Day of October, 2007

JON W. DUDAS
*Director of the United States Patent and Trademark Office*

SEQUENCE LISTING ( 1 ) GENERAL INFORMATION:

( i i i ) NUMBER OF SEQUENCES: 85

( 2 ) INFORMATION FOR SEQ ID NO:1:

( i ) SEQUENCE CHARACTERISTICS:
( A ) LENGTH: 3366 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:1:

```
TTTTGAAACT TGCAGAGAAC AGGATTATTT CTGGCGGCCT CTGCTGAGTT GGCGTGTGTG   60
TGTGTGTTTG TGTGTGTGTG TATTAGGGAG AGGAAATCGT AGGTCCAGTG TGGACCCAGA  120
GCTAAGGGGA ATCTTGGAGA GTAGTGGCTC TGGCAGATGA GGATTCAGAA ATCGAGTGCA  180
AGGACTGTTC TGGACTTTCA CTGCTAACCT GCTTTTTCTC AGTGCCTGGC TCTGAGGGCA  240
GGGTCCAGCT GGTGTCATGC TCTCCAAGGG CTTCATTTTA TGTTCCAGCC AGGCAAAGGA  300
GAGGTGAGAA ATGGAACCAA CATTTCTGAA AAGGAAATTT AAGAACTGCA TCATCTGCCC  360
TTGAAGAAGA AAAGGAGAAA AAAAAACAGG AGAGAGGGTA TTGAGAACAT CTTAGGGGAG  420
TTGTTAACTC CATTAAAAAA TATATGTGTT ACAGTGTTCA CTTGCCCAGT GTCTTCATAA  480
TCTTCCTTTA TAATGTGCAG CTGCCACGGC TAGTGTTTTT GTTTTTGTTG TTGTTGTTTT  540
GTTTCGTTTT TGGAGACAGA GTGTCGCTCT GTTGCCCAGG CTGGAGTACA ATGGTGCAAT  600
CTCGGCTCAC TGCAACCTCT GCCTCCTGGG TTCAAGCAAT TCTCCTGCCT CAGCCTCTCA  660
```

-continued

```
AGTAGCTGGG ACTACAGCCG TGTGCCAGCT AATGTTACAC CAGGCTAAAT TTGTTTTTTA   720
TTTTTTATTT TTGGTAGAGA CGGGGTTTCA CCATGTTAGC CAGGATGGTC TTAATCTCCT   780
GACCTCGTGA TCTGCCTGCC TCGGCCTCCC AAAGTGTTGG CTAGTGTTTT CTCTGCTTCA   840
GTGCTTGGGG TATGATTGGG TTATGGGAGT TCACACCGAG TCCAGGGCCT AGTCTTAATC   900
TTGCCAAAGA TGTTCTTTCC CCGGTGCTCA TGTTCTGATG TCCTTTCCCT CCTTCCCTTT   960
CTCCTCCCTT TCCTTTTCCC TTTGTCACTG CCCTCTTCCC TTTCCCAGCA TCCAGAGCTG  1020
CTGTTGGCGG ATTGTACCCA CGGGGAGATG ATTCCTCATG AAGAGCCTGG ATCCCCTACA  1080
GAAATCAAAT GTGACTTTCC GTTTATCAGA CTAAAATCAG AGCCATCCAG AACAGTGAAA  1140
CAGTCACCGT GGAGGGGGGA CGGCGAAAAA TGAAATCCAA CCAAGAGCGG AGCAACGAAT  1200
GCCTGCCTCC CAAGAAGCGC GAGATCCCCG CCACCAGCCG GTCCTCGGAG GAGAAGGCCC  1260
CTACCCTGAC CCAGCGACAA CCACCGGGTG GAGGGCACAG CATTGGCTCC CGGGCAACCC  1320
TGGTGGCCGG GGCCACGGGG GCGGGAGGCA TGGGCCGGCA GGGACCTCGG TGGAGCTTGG  1380
TTTACAACAG GGAATAGGTT TACACAAAGC ATTGTCCACA GGGCTGGACT ACTCCCCGCC  1440
CAGCGCTCCC AGGTCTGTCC CCGTGGCCAC CACGCTGCCT GCCGCGTACG CCACCCCGCA  1500
GCCAGGGACC CCGGTGTCCC CCGTGCAGTA CGCTCACCTG CCGCACACCT TCCAGTTCAT  1560
TGGGTCCTCC CAATACAGTG GAACCTATGC CAGCTTCATC CCATCACAGC TGATCCCCCC  1620
AACCGCCAAC CCCGTCACCA GTGCAGTGGC CTCGGCGCAG GGGCCACCAC TCCATCCCAG  1680
CGCTCCCAGC TGGAGGCCTA TTCCACTCTG CTGGCCAACA TGGGCAGTCT GAGCCAGACG  1740
CCGGGACACA AGGCTGAGCA GCAGCAGCAG CAGCAGCAGC AGCAGCAGCA GCAGCATCAG  1800
CATCAGCAGC AGCAGCAGCA GCAGCAGCAG CAGCAGCAGC AGCAGCAGCA CCTCAGCAGG  1860
GCTCCGGGGC TCATCACCCC GGGTCCCCCC CAACCAGCCC AGCAGAACCA GTACGTCCAC  1920
ATTTCCAGTT CTCCGCAGAA CACCGGCCGC ACCGCCTCTC CTCCGGCCAT CCCCGTCCAC  1980
CTCCACCCCC ACCAGACGAT GATCCCACAC ACGCTCACCC TGGGGCCCCC CTCCCAGGTC  2040
GTCATGCAAT ACGCCGACTC CGGCAGCCAC TTTGTCCCTC GGGAGGCCAC CAAGAAAGCC  2100
GAGAGCAGCC GGCTGCAGCA GGCCATCCAG GCCAAGGAGG TCCTGAACGG TGAGATGGAG  2160
AAGAGCCGGC GGTACGGGGC CCCGTCCTCA GCCGACCTGG GCCTGGGCAA GGCAGGCGGC  2220
AAGTCGGTTC CTCACCCGTA CGAGTCCAGG CACGTGGTGG TCCACCCGAG CCCCTCAGAC  2280
TACAGCAGTC GTGATCCTTC GGGGGTCCGG GCCTCTGTGA TGGTCCTGCC CAACAGCAAC  2340
ACGCCCGCAG CTGACCTGGA GGTGCAACAG GCCACTCATC GTGAAGCCTC CCCTTCTACC  2400
CTCAACGACA AAAGTGGCCT GCATTTAGGG AAGCCTGGCC ACCGGTCCTA CGCGCTCTCA  2460
CCCCACACGG TCATTCAGAC CACACACAGT GCTTCAGAGC CACTCCCGGT GGACTGCCAG  2520
CCACGGCCTT CTACGCAGGG ACTCAACCCC CTGTCATCGG CTACCTGAGC GGCCAGCAGC  2580
AAGCAATCAC CTACGCCGGC AGCCTGCCCC AGCACCTGGT GATCCCCGGC ACACAGCCCC  2640
TGCTCATCCC GGTCGGCAGC ACTGACATGG AAGCGTCGGG GGCAGCCCCG GCCATAGTCA  2700
CGTCATCCCC CCAGTTTGCT GCAGTGCCTC ACACGTTCGT CACCACCGCC CTTCCCAAGA  2760
GCGAGAACTT CAACCCTGAG GCCCTGGTCA CCCAGGCCGC CTACCCAGCC ATGGTGCAGG  2820
CCCAGATCCA CCTGCCTGTG GTGCAGTCCG TGGCCTCCCC GGCGGCGGCT CCCCCTACGC  2880
TGCCTCCCTA CTTCATGAAA GGCTCCATCA TCCAGTTGGC CAACGGGGAG CTAAAGAAGG  2940
TGGAAGACTT AAAACAGAAG ATTTCATCCA GAGTGCAGAG ATAAGCAACG ACCTGAAGAT  3000
CGACTCCAGC ACCGTAGAGA GGATTGAAGA CAGCCATAGC CCGGGCGTGG CCGTGATACA  3060
```

-continued

GTTCGCCGTC GGGGAGCACC GAGCCCAGGT AACGTTAGCC AGGGTGGCAC AGGGATGGGA 3120

CACCATACCG TGATGCCATC ATCATCTCCT GGCAAGACGA ATTGCTTCTA TGAGGCAGGA 3180

TTAAGGGTTC TCGGGTACAC CTAGACCTTA GACTCGGCCT TTCCCAACTG CGTTCTCTAG 3240

AAAAAATAAG CCCCATTTCC CCGTGATCTC TGCTGTGTGT AATGAATTAA CCTCCATGCA 3300

TGGAGAGTGG GGCTAGTTAT GGAGTCCTTG AGACAATCCA GAAACTCACC ACTCTCGTTA 3360

TTTTTT 3366

( 2 ) INFORMATION FOR SEQ ID NO:2:

( i ) SEQUENCE CHARACTERISTICS:
( A ) LENGTH: 195 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:2:

CAGCAGCAGC AGCAGCAGCA GCAGCAGCAG CAGCAGCAGC AGCAGCAGCA GCAGCAGCAG 60

CAGCAGCAGC AGCAGCAGCA GCAGCAGCAG CAGCAGCAGC AGCAGCAGCA GCAGCAGCAG 120

CAGCAGCAGC AGCAGCAGCA GCAGCAGCAG CAGCAGCAGC AGCAGCAGCA CCTCAGCAGG 180

GCTCCGGGGC TCATC 195

( 2 ) INFORMATION FOR SEQ ID NO:3:

( i ) SEQUENCE CHARACTERISTICS:
( A ) LENGTH: 234 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:3:

CAGCAGCAGC AGCAGCAGCA GCAGCAGCAG CAGCAGCAGC AGCAGCAGCA GCAGCAGCAG 60

CAGCAGCAGC AGCAGCAGCA GCAGCAGCAG CAGCAGCAGC AGCAGCAGCA GCAGCAGCAG 120

CAGCAGCAGC AGCAGCAGCA GCAGCAGCAG CAGCAGCAGC AGCAGCAGCA GCAGCAGCAG 180

CAGCAGCAGC AGCAGCAGCA GCAGCAGCAC CTCAGCAGGG CTCCGGGGCT CATC 234

( 2 ) INFORMATION FOR SEQ ID NO:4:

( i ) SEQUENCE CHARACTERISTICS:
( A ) LENGTH: 168 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:4:

CAGCAGCAGC AGCAGCAGCA GCAGCAGCAG CAGCAGCAGC AGCAGCAGCA GCAGCAGCAG 60

CAGCAGCAGC AGCAGCAGCA GCAGCAGCAG CAGCAGCAGC AGCAGCAGCA GCAGCAGCAG 120

CAGCAGCAGC AGCAGCAGCA GCACCTCAGC AGGGCTCCGG GGCTCATC 168

( 2 ) INFORMATION FOR SEQ ID NO:5:

( i ) SEQUENCE CHARACTERISTICS:
( A ) LENGTH: 171 base pairs
( B ) TYPE: nucleic acid
( C ) STRANDEDNESS: single ( D ) TOPOLOGY: linear ( i i ) MOLECULE TYPE: DNA ( x i ) SEQUENCE DESCRIPTION: SEQ ID NO:5:

CAGCAGCAGC AGCAGCAGCA GCAGCAGCAG CAGCAGCAGC AGCAGCAGCA GCAGCAGCAG 60

CAGCAGCAGC AGCAGCAGCA GCAGCAGCAG CAGCAGCAGC AGCAGCAGCA GCAGCAGCAG 120

CAGCAGCAGC AGCAGCAGCA GCAGCACCTC AGCAGGGCTC CGGGGCTCAT C 171

( 2 ) INFORMATION FOR SEQ ID NO:6:

( i ) SEQUENCE CHARACTERISTICS:
( A ) LENGTH: 154 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:6:

TGAGCAGCAG CAGCAGCAGC AGCAGCAGCA GCAGCAGCAG CAGCAGCAGC AGCAGCAGCA 60

GCAGCAGCAG CAGCAGCAGC AGCAGCAGCA GCAGCAGCAG CAGCAGCAGC AGCAGCAGCA 120

GCAGCAGCAG CAGCAGCAGC AGCAGCAGCA GCAG 154

( 2 ) INFORMATION FOR SEQ ID NO:7:

( i ) SEQUENCE CHARACTERISTICS:
( A ) LENGTH: 506 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:7:

GATCCCCCCA ACCGCCAACC CCGTCACCAG TGCAGTGGCC TCGGCGCAGG GGCCACCACT 60

CCATCCCAGC CCTCCCAGCT GGAGGCCTAT TCCACTCTGC TGGCCAACAT GGGCAGTCTG 120

AGCCAGACGC CGGGACACAA GGCTGAGCAG CAGCAGCAGC AGCAGCAGCA GCAGCAGCAG 180

CAGCATCAGC ATCAGCAGCA GCAGCAGCAG CAGCAGCAGC AGCAGCAGCA CCAGCAGCAC 240

CTCAGCAGGG CTCCGGGGCT CATCACCCCG GGTCCCCCCC ACCAGCCCAG CAGAACCAGT 300

ACGTCCACAT TTCCAGTTCT CCGCAGAACA CCGGCCGCAC CGCCTCTCCT CCGGCCATCC 360

CCGTCCACCT CCACCCCCAC CAGACGATGA TCCCACACAC GCTCACCCTG GGGCCCCCCT 420

CCCAGGTCGT CATGCAATAC GCCGACTCCG GCAGCCACTT TGTCCCTCGG GAGGCCACCA 480

AGAAAGCCGA GAGCAGCCGG CTGCAG 506

( 2 ) INFORMATION FOR SEQ ID NO:8:

( i ) SEQUENCE CHARACTERISTICS:
( A ) LENGTH: 10660 base pairs
( B ) TYPE: nucleic acid
( C ) STRANDEDNESS: single
( D ) TOPOLOGY: linear ( i i ) MOLECULE TYPE: DNA ( i x ) FEATURE:
( A ) NAME/KEY: CDS
( B ) LOCATION: 936..3384

( x i ) SEQUENCE DESCRIPTION: SEQ ID NO:8:

CTACTACAGT GGCGGACGTA CAGGACCTGT TTCACTGCAG GGGGATCCAA AACAAGCCCC 60

-continued

GTGGAGCAAC AGCCAGAGCA ACAGCAGCTG CAAGACATTG TTTCTCTCCC TCTGCCCCCC 120

CTTCCCCACG CAACCCCAGA TCCATTTACA CTTTACAGTT TTACCTCACA AAAACTACTA 180

CAAGCACCAA GCTCCCTGAT GGAAAGGAGC ATCGTGCATC AAGTCACCAG GGTGGTCCAT 240

TCAAGCTGCA GATTTGTTTG TCATCCTTGT ACAGCAATCT CCTCCTCCAC TGCCACTACA 300

GGGAAGTGCA TCACATGTCA GCATACTGGA GCATAGTGAA AGAGTCTATT TTGAAGCTTC 360

AAACTTAGTG CTGCTGCAGA CCAGGAACAA GAGAGAAAGA GTGGATTTCA GCCTGCACGG 420

ATGGTCTTGA AACACAAATG GTTTTTGGTC TAGGCGTTTT ACACTGAGAT TCTCCACTGC 480

CACCCTTTCT ACTCAAGCAA AATCTTCGTG AAAAGATCTG CTGCAAGGAA CTGATAGCTT 540

ATGGTTCTCC ATTGTGATGA AAGCACATGG TACAGTTTTC CAAAGAAATT AGACCATTTT 600

CTTCGTGAGA AAGAAATCGA CGTGCTGTTT TCATAGGGTA TTTCTCACTT CTCTGTGAAA 660

GGAAGAAAGA ACACGCCTGA GCCCAAGAGC CCTCAGGAGC CCTCCAGAGC CTGTGGGAAG 720

TCTCCATGGT GAAGTATAGG CTGAGGCTAC CTGTGAACAG TACGCAGTGA ATGTTCATCC 780

AGAGCTGCTG TTGGCGGATT GTACCCACGG GGAGATGATT CCTCATGAAG AGCCTGGATC 840

CCCTACAGAA ATCAAATGTG ACTTTCCGTT TATCAGACTA AAATCAGAGC CATCCAGACA 900

GTGAAACAGT CACCGTGGAG GGGGGACGGC GAAAA ATG AAA TCC AAC CAA GAG 953
Met Lys Ser Asn Gln Glu
1 5

CGG AGC AAC GAA TGC CTG CCT CCC AAG AAG CGC GAG ATC CCC GCC ACC 1001
Arg Ser Asn Glu Cys Leu Pro Pro Lys Lys Arg Glu Ile Pro Ala Thr
10 15 20

AGC CGG TCC TCC GAG GAG AAG GCC CCT ACC CTG CCC AGC GAC AAC CAC 1049
Ser Arg Ser Ser Glu Glu Lys Ala Pro Thr Leu Pro Ser Asp Asn His
25 30 35

CGG GTG GAG GGC ACA GCA TGG CTC CCG GGC AAC CCT GGT GGC CGG GGC 1097
Arg Val Glu Gly Thr Ala Trp Leu Pro Gly Asn Pro Gly Gly Arg Gly
40 45 50

CAC GGG GGC GGG AGG CAT GGG CCG GCA GGG ACC TCG GTG GAG CTT GGT 1145
His Gly Gly Gly Arg His Gly Pro Ala Gly Thr Ser Val Glu Leu Gly
55 60 65 70

TTA CAA CAG GGA ATA GGT TTA CAC AAA GCA TTG TCC ACA GGG CTG GAC 1193
Leu Gln Gln Gly Ile Gly Leu His Lys Ala Leu Ser Thr Gly Leu Asp
75 80 85

TAC TCC CCG CCC AGC GCT CCC AGG TCT GTC CCC GTG GCC ACC ACG CTG 1241
Tyr Ser Pro Pro Ser Ala Pro Arg Ser Val Pro Val Ala Thr Thr Leu
90 95 100

CCT GCC GCG TAC GCC ACC CCG CAG CCA GGG ACC CCG GTG TCC CCC GTG 1289
Pro Ala Ala Tyr Ala Thr Pro Gln Pro Gly Thr Pro Val Ser Pro Val
105 110 115

CAG TAC GCT CAC CTG CCG CAC ACC TTC CAG TTC ATT GGG TCC TCC CAA 1337
Gln Tyr Ala His Leu Pro His Thr Phe Gln Phe Ile Gly Ser Ser Gln
120 125 130

TAC AGT GGA ACC TAT GCC AGC TTC ATC CCA TCA CAG CTG ATC CCC CCA 1385
Tyr Ser Gly Thr Tyr Ala Ser Phe Ile Pro Ser Gln Leu Ile Pro Pro
135 140 145 150

ACC GCC AAC CCC GTC ACC AGT GCA GTG GCC TCG GCC GCA GGG GCC ACC 1433
Thr Ala Asn Pro Val Thr Ser Ala Val Ala Ser Ala Ala Gly Ala Thr
155 160 165

ACT CCA TCC CAG CGC TCC CAG CTG GAG GCC TAT TCC ACT CTG CTG GCC 1481
Thr Pro Ser Gln Arg Ser Gln Leu Glu Ala Tyr Ser Thr Leu Leu Ala
170 175 180

AAC ATG GGC AGT CTG AGC CAG ACG CCG GGA CAC AAG GCT GAG CAG CAG 1529
Asn Met Gly Ser Leu Ser Gln Thr Pro Gly His Lys Ala Glu Gln Gln
185 190 195

-continued

```
CAG CAG CAG CAG CAG CAG CAG CAG CAG CAG CAT CAG CAT CAG CAG CAG     1577
Gln Gln Gln Gln Gln Gln Gln Gln Gln Gln His Gln His Gln Gln Gln
    200                 205                 210

CAG CAG CAG CAG CAG CAG CAG CAG CAG CAG CAG CAG CAC CTC AGC AGG     1625
Gln Gln Gln Gln Gln Gln Gln Gln Gln Gln Gln Gln His Leu Ser Arg
215                 220                 225                 230

GCT CCG GGG CTC ATC ACC CCG GGG TCC CCC CCA CCA GCC CAG CAG AAC     1673
Ala Pro Gly Leu Ile Thr Pro Gly Ser Pro Pro Pro Ala Gln Gln Asn
                235                 240                 245

CAG TAC GTC CAC ATT TCC AGT TCT CCG CAG AAC ACC GGC CGC ACC GCC     1721
Gln Tyr Val His Ile Ser Ser Ser Pro Gln Asn Thr Gly Arg Thr Ala
            250                 255                 260

TCT CCT CCG GCC ATC CCC GTC CAC CTC CAC CCC CAC CAG ACG ATG ATC     1769
Ser Pro Pro Ala Ile Pro Val His Leu His Pro His Gln Thr Met Ile
        265                 270                 275

CCA CAC ACG CTC ACC CTG GGG CCC CCC TCC CAG GTC GTC ATG CAA TAC     1817
Pro His Thr Leu Thr Leu Gly Pro Pro Ser Gln Val Val Met Gln Tyr
    280                 285                 290

GCC GAC TCC GGC AGC CAC TTT GTC CCT CGG GAG GCC ACC AAG AAA GCT     1865
Ala Asp Ser Gly Ser His Phe Val Pro Arg Glu Ala Thr Lys Lys Ala
295                 300                 305                 310

GAG AGC AGC CGG CTG CAG CAG GCC ATC CAG GCC AAG GAG GTC CTG AAC     1913
Glu Ser Ser Arg Leu Gln Gln Ala Ile Gln Ala Lys Glu Val Leu Asn
                315                 320                 325

GGT GAG ATG GAG AAG AGC CGG CGG TAC GGG GCC CCG TCC TCA GCC GAC     1961
Gly Glu Met Glu Lys Ser Arg Arg Tyr Gly Ala Pro Ser Ser Ala Asp
            330                 335                 340

CTG GGC CTG GGC AAG GCA GGC GGC AAG TCG GTT CCT CAC CCG TAC GAG     2009
Leu Gly Leu Gly Lys Ala Gly Gly Lys Ser Val Pro His Pro Tyr Glu
        345                 350                 355

TCC AGG CAC GTG GTG GTC CAC CCG AGC CCC TCA GAC TAC AGC AGT CGT     2057
Ser Arg His Val Val Val His Pro Ser Pro Ser Asp Tyr Ser Ser Arg
    360                 365                 370

GAT CCT TCG GGG GTC CGG GCC TCT GTG ATG GTC CTG CCC AAC AGC AAC     2105
Asp Pro Ser Gly Val Arg Ala Ser Val Met Val Leu Pro Asn Ser Asn
375                 380                 385                 390

ACG CCC GCA GCT GAC CTG GAG GTG CAA CAG GCC ACT CAT CGT GAA GCC     2153
Thr Pro Ala Ala Asp Leu Glu Val Gln Gln Ala Thr His Arg Glu Ala
                395                 400                 405

TCC CCT TCT ACC CTC AAC GAC AAA AGT GGC CTG CAT TTA GGG AAG CCT     2201
Ser Pro Ser Thr Leu Asn Asp Lys Ser Gly Leu His Leu Gly Lys Pro
            410                 415                 420

GGC CAC CGG TCC TAC GCG CTC TCA CCC CAC ACG GTC ATT CAG ACC ACA     2249
Gly His Arg Ser Tyr Ala Leu Ser Pro His Thr Val Ile Gln Thr Thr
        425                 430                 435

CAC AGT GCT TCA GAG CCA CTC CCG GTG GGA CTG CCA GCC ACG GCC TTC     2297
His Ser Ala Ser Glu Pro Leu Pro Val Gly Leu Pro Ala Thr Ala Phe
    440                 445                 450

TAC GCA GGG ACT CAA CCC CCT GTC ATC GGC TAC CTG AGC GGC CAG CAG     2345
Tyr Ala Gly Thr Gln Pro Pro Val Ile Gly Tyr Leu Ser Gly Gln Gln
455                 460                 465                 470

CAA GCA ATC ACC TAC GCC GGC AGC CTG CCC CAG CAC CTG GTG ATC CCC     2393
Gln Ala Ile Thr Tyr Ala Gly Ser Leu Pro Gln His Leu Val Ile Pro
                475                 480                 485

GGC ACA CAG CCC CTG CTC ATC CCG GTC GGC AGC ACT GAC ATG GAA GCG     2441
Gly Thr Gln Pro Leu Leu Ile Pro Val Gly Ser Thr Asp Met Glu Ala
            490                 495                 500

TCG GGG GCA GCC CCG GCC ATA GTC ACG TCA TCC CCC CAG TTT GCT GCA     2489
Ser Gly Ala Ala Pro Ala Ile Val Thr Ser Ser Pro Gln Phe Ala Ala
        505                 510                 515
```

-continued

GTG CCT CAC ACG TTC GTC ACC ACC GCC CTT CCC AAG AGC GAG AAC TTC 2537
Val Pro His Thr Phe Val Thr Thr Ala Leu Pro Lys Ser Glu Asn Phe
520 525 530

AAC CCT GAG GCC CTG GTC ACC CAG GCC GCC TAC CCA GCC ATG GTG CAG 2585
Asn Pro Glu Ala Leu Val Thr Gln Ala Ala Tyr Pro Ala Met Val Gln
535 540 545 550

GCC CAG ATC CAC CTG CCT GTG GTG CAG TCC GTG GCC TCC CCG GCG GCG 2633
Ala Gln Ile His Leu Pro Val Val Gln Ser Val Ala Ser Pro Ala Ala
555 560 565

GCT CCC CCT ACG CTG CCT CCC TAC TTC ATG AAA GGC TCC ATC ATC CAG 2681
Ala Pro Pro Thr Leu Pro Pro Tyr Phe Met Lys Gly Ser Ile Ile Gln
570 575 580

TTG GCC AAC GGG GAG CTA AAG AAG GTG GAA GAC TTA AAA ACA GAA GAT 2729
Leu Ala Asn Gly Glu Leu Lys Lys Val Glu Asp Leu Lys Thr Glu Asp
585 590 595

TTC ATC CAG AGT GCA GAG ATA AGC AAC GAC CTG AAG ATC GAC TCC AGC 2777
Phe Ile Gln Ser Ala Glu Ile Ser Asn Asp Leu Lys Ile Asp Ser Ser
600 605 610

ACC GTA GAG AGG ATT GAA GAC AGC CAT AGC CCG GGC GTG GCC GTG ATA 2825
Thr Val Glu Arg Ile Glu Asp Ser His Ser Pro Gly Val Ala Val Ile
615 620 625 630

CAG TTC GCC GTC GGG GAG CAC CGA GCC CAG GTC AGC GTT GAA GTT TTG 2873
Gln Phe Ala Val Gly Glu His Arg Ala Gln Val Ser Val Glu Val Leu
635 640 645

GTA GAG TAT CCT TTT TTT GTG TTT GGA CAG GGC TGG TCA TCC TGC TGT 2921
Val Glu Tyr Pro Phe Phe Val Phe Gly Gln Gly Trp Ser Ser Cys Cys
650 655 660

CCG GAG AGA ACC AGC CAG CTC TTT GAT TTG CCG TGT TCC AAA CTC TCA 2969
Pro Glu Arg Thr Ser Gln Leu Phe Asp Leu Pro Cys Ser Lys Leu Ser
665 670 675

GTT GGG GAT GTC TGC ATC TCG CTT ACC CTC AAG AAC CTG AAG AAC GGC 3017
Val Gly Asp Val Cys Ile Ser Leu Thr Leu Lys Asn Leu Lys Asn Gly
680 685 690

TCT GTT AAA AAG GGC CAG CCC GTG GAT CCC GCC AGC GTC CTG CTG AAG 3065
Ser Val Lys Lys Gly Gln Pro Val Asp Pro Ala Ser Val Leu Leu Lys
695 700 705 710

CAC TCA AAG GCC GAC GGC CTG GCG GGC AGC AGA CAC AGG TAT GCC GAG 3113
His Ser Lys Ala Asp Gly Leu Ala Gly Ser Arg His Arg Tyr Ala Glu
715 720 725

CAG GAA AAC GGA ATC AAC CAG GGG AGT GCC CAG ATG CTC TCT GAG AAT 3161
Gln Glu Asn Gly Ile Asn Gln Gly Ser Ala Gln Met Leu Ser Glu Asn
730 735 740

GGC GAA CTG AAG TTT CCA GAG AAA ATG GGA TTG CCT GCA GCG CCC TTC 3209
Gly Glu Leu Lys Phe Pro Glu Lys Met Gly Leu Pro Ala Ala Pro Phe
745 750 755

CTC ACC AAA ATA GAA CCC AGC AAG CCC GCG GCA ACG AGG AAG AGG AGG 3257
Leu Thr Lys Ile Glu Pro Ser Lys Pro Ala Ala Thr Arg Lys Arg Arg
760 765 770

TGG TCG GCG CCA GAG AGC CGC AAA CTG GAG AAG TCA GAA GAC GAA CCA 3305
Trp Ser Ala Pro Glu Ser Arg Lys Leu Glu Lys Ser Glu Asp Glu Pro
775 780 785 790

CCT TTG ACT CTT CCT AAG CCT TCT CTA ATT CCT CAG GAG GTT AAG ATT 3353
Pro Leu Thr Leu Pro Lys Pro Ser Leu Ile Pro Gln Glu Val Lys Ile
795 800 805

TGC ATT GAA GGC CGG TCT AAT GTA GGC AAG T AGAGGCAGCG TGGGGGAAAG 3404
Cys Ile Glu Gly Arg Ser Asn Val Gly Lys
810 815

GAAACGTGGC TCTCCCTTAT CATTTGTATC CAGATTACTG TACTGTAGGC TAAAATAACA 3464

CAGTATTTAC ATGTTATCTT CTTAATTTTA GGTTTCTGTT CTAACCTTGT CATTAGAGTT 3524

-continued

ACAGCAGGTG TGTCGCAGGA GACTGGTGCA TATGCTTTTT CCACGAGTGT CTGTCAGTGA 3584

GCGGGCGGGA GGAAGGGCAC AGCAGGAGCG GTCAGGGCTC CAGGCATCCC CGGGGAAGAA 3644

AGGAACGGGG CTTCACAGTG CCTGCCTTCT CTAGCGGCAC AGAAGCAGCC GGGGGCGCTG 3704

ACTCCCGCTA GTGTCAGGAG AAAAGTCCCG TGGGAAGAGT CCTGCAGGGG TGCAGGGTTG 3764

CACGCATGTG GGGGTGCACA GGCGCTGTGG CGGCGAGTGA GGGTCTCTTT TTCTCTGCCT 3824

CCCTCTGCCT CACTCTCTTG CTATCGGCAT GGGCCGGGGG GGTTCAGAGC AGTGTCCTCC 3884

TGGGGTTCCC ACGTGCAAAA TCAACATCAG GAACCCAGCT TCAGGGCATC GCGGAGACGC 3944

GTCAGATGGC AGATTTGGAA AGTTAACCAT TTAAAAGAAC ATTTTTCTCT CCAACATATT 4004

TTACAATAAA AGCAACTTTT AATTGTATAG ATATATATTT CCCCCTATGG GGCCTGACTG 4064

CACTGATATA TATTTTTTTT AAAGAGCAAC TGCCACATGC GGGATTTCAT TTCTGCTTTT 4124

TACTAGTGCA GCGATGTCAC CAGGGTGTTG TGGTGGACAG GGAAGCCCCT GCTGTCATGG 4184

CCCCACATGG GGTAAGGGGG GTTGGGGGTG GGGGAGAGGG AGAGAGCGAA CACCCACGCT 4244

GGTTTCTGTG CAGTGTTAGG AAAACCAATC AGGTTATTGC ATTGACTTCA CTCCCAAGAG 4304

GTAGATGCAA ACTGCCCTTC AGTGAGAGCA ACAGAAGCTC TTCACGTTGA GTTTGCGAAA 4364

TCTTTTTGTC TTTGAACTCT AGTACTGTTT ATAGTTCATG ACTATGGACA ACTCGGGTGC 4424

CACTTTTTTT TTTTTCAGAT TCCAGTGTGA CATGAGGAAT TAGATTTTGA AGATGAGCAT 4484

ATATTACTAT CTTTAAGCAT TTAAAAATAC TGTTCACACT TTATTACCAA GCATCTTGGT 4544

CTCTCATTCA ACAAGTACTG TATCTCACTT TAAACTCTTT GGGGAAAAAA CAAAAACAAA 4604

AAAAACTAAG TTGCTTTCTT TTTTTCAACA CTGTAACTAC ATTTCAGCTC TGCAGAATTG 4664

CTGAAGAGCA AGATATTGAA AGTTTCAATG TGGTTTAAAG GGATGAATGT GAATTATGAA 4724

CTAGTATGTG ACAATAAATG ACCACCAAGT ACTACCTGAC GGGAGGCACT TTTCACTTTG 4784

ATGTCTGAGA ATCAGTTCAA GGCATATGCA GAGTTGGCAG AGAAACTGAG AGAAAAGGGA 4844

TGGAGAAGAG AATACTCATT TTTGTCCAGT GTTTTTCTTT TTAAGATGAA CTTTTAAAGA 4904

ACCTTGCGAT TTGCACATAT TGAGTTTATA ACTTGTGTGA TATTCCTGCA GTTTTTATCC 4964

AATAACATTG TGGGAAAGGT TTGGGGGACT GAACGAGCAT AAATAAATGT AGCAAAATTT 5024

CTTTCTAACC TGCCTAAACT CTAGGCCATT TTATAAGGTT ATGTTCCTTT GAAAATTCAT 5084

TTTGGTCTTT TTACCACATC TGTCACAAAA AGCCAGGTCT TAGCGGGCTC TTAGAAACTC 5144

TGAGAATTTT CTTCAGATTC ATTGAGAGAG TTTTCCATAA AGACATTTAT ATATGTGAGC 5204

AAGATTTTTT TTAAACAATT ACTTTATTAT TGTTGTTATT AATGTTATTT TCAGAATGGC 5264

TTTTTTTTTC TATTCAAAAT CAAATCGAGA TTTAATGTTT GGTACAAACC CAGAAAGGGT 5324

ATTTCATAGT TTTTAAACCT TTCATTCCCA GAGATCCGAA ATATCATTTG TGGGTTTTGA 5384

ATGCATCTTT AAAGTGCTTT AAAAAAAAGT TTTATAAGTA GGGAGAAATT TTTAAATATT 5444

CTTACTTGGA TGGCTGCAAC TAAACTGAAC AAATACCTGA CTTTTCTTTT ACCCCATTGA 5504

AAATAGTACT TTCTTCGTTT CACAAATTAA AAAAAAAATC TGGTATCAAC CCACATTTTG 5564

GCTGTCTAGT ATTCATTTAC ATTTAGGGTT CACCAGGACT AATGATTTTT ATAAACCGTT 5624

TTCTGGGGTG TACCAAAAAC ATTTGAATAG GTTTAGAATA GCTAGAATAG TTCCTTGACT 5684

TTCCTCGAAT TTCATTACCC TCTCAGCATG CTTGCAGAGA GCTGGGTGGG CTCATTCTTG 5744

CAGTCATACT GCTTATTTAG TGCTGTATTT TTTAAACGTT TCTGTTCAGA GAACTTGCTT 5804

AATCTTCCAT ATATTCTGCT CAGGGCACTT GCAATTATTA GGTTTTGTTT TTCTTTTTGT 5864

TTTTTAGCCT TTGATGGTAA GAGGAATACG GGCTGCCACA TAGACTTTGT TCTCATTAAT 5924

-continued

```
ATCACTATTT ACAACTCATG TGGACTCAGA AAAACACACA CCACCTTTTG GCTTACTTCG 5984
AGTATTGAAT TGACTGGATC CACTAAACCA ACACTAAGAT GGGAAAACAC ACATGGTTTG 6044
GAGCAATAGG AACATCATCA TAATTTTTGT GGTTCTATTT CAGGTATAGG AATTATAAAA 6104
TAATTGGTTC TTTCTAAACA CTTGTCCCAT TTCATTCTCT TGCTTTTTTA GCATGTGCAA 6164
TACTTTCTGT GCCAATAGAG TCTGACCAGT GTGCTATATA GTTAAAGCTC ATTCCCTTTT 6224
GGCTTTTTCC TTGTTTGGTT GATCTTCCCC ATTCTGGCCA GAGCAGGGCT GGAGGGAAGG 6284
AGCCAGGAGG GAGAGAGCCT CCCACCTTTC CCCTGCTGCG GATGCTGAGT GCTGGGGCGG 6344
GGAGCCTTCA GGAGCCCCGT GCGTCTGCCG CCACGTTGCA GAAAGAGCCA GCCAAGGAGA 6404
CCCGGGGGAG GAACCGCAGT GTCCCCTGTC ACCACACGGA ATAGTGAATG TGGAGTGTGG 6464
AGAGGAAGGA GGCAGATTCA TTTCTAAGAC GCACTCTGGA GCCATGTAGC CTGGAGTCAA 6524
CCCATTTTCC ACGGTCTTTT CTGCAAGTGG GCAGGCCCCT CCTCGGGGTC TGTGTCCTTG 6584
AGACTTGGAG CCCTGCCTCT GAGCCTGGAC GGGAAGTGTG GCCTGTTGTG TGTGTGCGTT 6644
CTGAGCGTGT TGGCCAGTGG CTGTGGAGGG GACCACCTGC CACCCACGGT CACCACTCCC 6704
TTGTGGCAGC TTTCTCTTCA AATAGGAAGA ACGCACAGAG GGCAGGAGCC TCCTGTTTGC 6764
AGACGTTGGC GGGCCCCGAG GCTCCCAGAG CAGCCTCTGT CACCGCTTCT GTGTAGCAAA 6824
CATTAACGAT GACAGGGGTA GAAATTCTTC GGTGCCGTTC AGCTTACAAG GATCAGCCAT 6884
GTGCCTCTGT ACTATGTCCA CTTTGCAATA TTTACCGACA GCCGTCTTTT GTTCTTTCTT 6944
TCCTGTTTTC CATTTTTAAA CTAGTAACAG CAGGCCTTTT GCGTTTACAA TGGAACACAA 7004
TCACCAAGAA ATTAGTCAGG GCGAAAAGAA AAAAATAATA CTATTAATAA GAAACCAACA 7064
AACAAGAACC TCTCTTTCTA GGGATTTCTA AATATATAAA ATGACTGTTC CTTAGAATGT 7124
TTAACTTAAG AATTATTTCA GTTTGTCTGG GCCACACTGG GGCAGAGGGG GGAGGGAGGG 7184
ATACAGAGAT GGATGCCACT TACCTCAGAT CTTTTAAAGT GGAAATCCAA ATTGAATTTT 7244
CATTTGGACT TTCAGGATAA TTTTCTATGT TGGTCAACTT TTCGTTTTCC CTAACTCACC 7304
CAGTTTAGTT TGGGATGATT TGATTTCTGT TGTTGTTGAT CCCATTTCTA ACTTGGAATT 7364
GTGAGCCTCT ATGTTTTCTG TTAGGTGAGT GTGTTGGGTT TTTTCCCCCC ACCAGGAAGT 7424
GGCAGCATCC CTCCTTCTCC CCTAAAGGGA CTCTGCGGAA CCTTTCACAC CTCTTTCTCA 7484
GGGACGGGGC AGGTGTGTGT GTGGTACACT GACGTGTCCA GAAGCAGCAC TTTGACTGCT 7544
CTGGAGTAGG GTTGTACAAT TTCAAGGAAT GTTTGGATTT CCTGCATCTT GTGGATTACT 7604
CCTTAGATAC CGCATAGATT GCAATATAAT GCTGCATGTT CAAGATGAAC AGTAGCTCCT 7664
AGTAATCATA AAATCCACTC TTTGCACAGT TTGATCTTTA CTGAAATATG TTGCCAAAAT 7724
TTATTTTTGT TGTTGTAGCT CTGGATTTTG TTTTGTTTTG TTTTTTAAGG AAACGATTGA 7784
CAATACCCTT TAACATCTGT GACTACTAAG GAAACCTATT TCTTTCATAG AGAGAAAAAT 7844
CTCCAATGCT TTTGAAGACA CTAATACCGT GCTATTTCAG ATATGGGTGA GGAAGCAGAG 7904
CTCTCGGTAC CGAAGGCCGG GCTTCTTGAG CTGTGTTGGT TGTCATGGCT ACTGTTTCAT 7964
GAACCACAAG CAGCTCAACA GACTGGTCTG TTGCCTTCTG AAACCCTTTG CACTTCAATT 8024
TGCACCAGGT GAAAACAGGG CCAGCAGACT CCATGGCCCA ATTCGGTTTC TTCGGTGGTG 8084
ATGTGAAAGG AGAGAATTAC ACTTTTTTTT TTTTTAAGTG GCGTGGAGGC CTTTGCTTCC 8144
ACATTTGTTT TTAACCCAGA ATTTCTGAAA TAGAGAATTT AAGAACACAT CAAGTAATAA 8204
ATATACAGAG AATATACTTT TTTATAAAGC ACATGCATCT GCTATTGTGT TGGGTTGGTT 8264
TCCTCTCTTT TCCACGGACA GTGTTGTGTT TCTGGCATAG GGAAACTCCA AACAACTTGC 8324
```

-continued

```
ACACCTCTAC TCCGGAGCTG AGATTTCTTT TACATAGATG ACCTCGCTTC AAATACGTTA  8384
CCTTACTGAT GATAGGATCT TTTCTTGTAG CACTATACCT TGTGGGAATT TTTTTTTAAA  8444
TGTACACCTG ATTTGAGAAG CTGAAGAAAA CAAAATTTTG AAGCACTCAC TTTGAGGAGT  8504
ACAGGTAATG TTTTAAAAAA TTGCACAAAA GAAAAATGAA TGTCGAAATG ATTCATTCAG  8564
TGTTTGAAAG ATATGGCTCT GTTGAAACAA TGAGTTTCAT ACTTTGTTTG TAAAAAAAAA  8624
AAGCAGAGAA GGGTTGAAAG TTACATGTTT TTTTGTATAT AGAAATTTGT CATGTCTAAA  8684
TGATCAGATT TGTATGGTTA TGGCCTGGAA GAATTACTAC GTAAAAGGCT CTTAAACTAT  8744
ACCTATGCTT ATTGTTATTT TTGTTACATA TAGCCCTCGT CTGAGGGAGG GGAACTCGGT  8804
ATTCTGCGAT TTGAGAATAC TGTTCATTCC TATGCTGAAA GTACTTCTCT GAGCTCCCTT  8864
CTTAGTCTAA ACTCTTAAGC CATTGCAACT TCTTTTTCTT CAGAGATGAT GTTTGACATT  8924
TTCAGCACTT CCTGTTCCTA TAAACCCAAA GAATATAATC TTGAACACGA AGTGTTTGTA  8984
ACAAGGGATC CAGGCTACCA ATCAAACAGG ACTCATTATG GGGACAAAAA AAAAAAAAAT  9044
TATTTCACCT TCTTTCCCCC CACACCTCAT TTAAATGGGG GGAGTAAAAA CATGATTTCA  9104
ATGTAAATGC CTCATTTTAT TTTAGTTTTA TTTTGATTTT TATTTAATAT AAAGAGGCCA  9164
GAATAAATAC GGAGCATCTT CTCAGAATAG TATTCCTGTC CAAAAATCAA GCCGGACAGT  9224
GGAAACTGGA CAGCTGTGGG GATATTAAGC ACCCCCACTT ACAATTCTTA AATTCAGAAT  9284
CTCGTCCCCT CCCTTCTCGT TGAAGGCAAC TGTTCTGGTA GCTAACTTTC TCCTGTGTAA  9344
TGGCGGGAGG GAACACCGGC TTCAGTTTTT CATGTCCCCA TGACTTGCAT ACAAATGGTT  9404
CAACTGTATT AAAATTAAGT GCATTTGGCC AATAGGTAGT ATCTATACAA TAACAACAAT  9464
CTCTAAGAAT TTCCATAACT TTTCTTATCT GAAAGGACTC AAGTCTTCCA CTGCAGATAC  9524
ATTGGAGGCT TCACCCACGT TTTCTTTCCC TTTAGTTTGT TTGCTGTCTG GATGGCCAAT  9584
GAGCCTGTCT CCTTTTCTGT GGCCAATCTG AAGGCCTTCG TTGGAAGTGT TGTTCACAGT  9644
AATCCTTACC AAGATAACAT ACTGTCCTCC AGAATACCAA GTATTAGGTG ACACTAGCTC  9704
AAGCTGTTGT CTTCAGAGCA GTTACCAAGA AGCTCGGTGC ACAGGTTTTC TCTGGTTCTT  9764
ACAGGAACCA CCTACTCTTT CAGTTTTCTG GCCCAGGAGT GGGGTAAATC CTTTAGTTAG  9824
TGCATTTGAA CTTGGTACCT GTGCATTCAG TTCTGTGAAT ACTGCCCTTT TTGGCGGGGT  9884
TTCCTCATCT CCCCAGCCTG AACTGCTCAA CTCTAAACCC AAATTAGTGT CAGCCGAAAG  9944
GAGGTTTCAA GATAGTCCTG TCAGTATTTG TGGTGACCTT CAGATTAGAC AGTCTTCATT 10004
TCCAGCCAGT GGAGTCCTGG CTCCAGAGCC ATCTCTGAGA CTCCGTACTA CTGGATGTTT 10064
TAATATCAGA TCATTACCCA CCATATGCCT CCCACAGGCC AAGGGAAAAC AGACACCAGA 10124
ACTTGGGTTG AGGGCACTAC CAGACTGACA TGGCCAGTAC AGAGGAGAAC TAGGGAAGGA 10184
ATGATGTTTT GCACCTTATT GAAAAGAAAA TTTTAAGTGC ATACATAATA GTTAAGAGCT 10244
TTTATTGTGA CAGGAGAACT TTTTTCCATA TGCGTGCATA CTCTCTGTAA TTCCAGTGTA 10304
AAATATTGTA CTTGCACTAG CTTTTTTAAA CAAATATTAA AAAATGGAAG AATTCATATT 10364
CTATTTTCTA ATCGTGGTGT GTCTATTTGT AGGATACACT CGAGTCTGTT TATTGAATTT 10424
TATGGTCCCT TTCTTTGATG GTGCTTGCAG GTTTTCTAGG TAGAAATTAT TTCATTATTA 10484
TAATAAAACA ATGTTTGATT CAAAATTTGA ACAAAATTGT TTTAAATAAA TTGTCTGTAT 10544
ACCAGTACAA GTTTATTGTT TCAGTATACT CGTACTAATA AAATAACAGT GCCAATTGCA 10604
AAAAAAAAAA AAAAAAAAAA AAAAAAAAAA AAAAAAAAAA AAAAAAAAAA AAAAAA      10660
```

( 2 ) INFORMATION FOR SEQ ID NO:9:

( i ) SEQUENCE CHARACTERISTICS:
( A ) LENGTH: 816 amino acids
( B ) TYPE: amino acid
( D ) TOPOLOGY: linear ( i i ) MOLECULE TYPE: protein ( x i ) SEQUENCE DESCRIPTION: SEQ ID NO:9:

Met Lys Ser Asn Gln Glu Arg Ser Asn Glu Cys Leu Pro Pro Lys Lys
1 5 10 15

Arg Glu Ile Pro Ala Thr Ser Arg Ser Ser Glu Glu Lys Ala Pro Thr
20 25 30

Leu Pro Ser Asp Asn His Arg Val Glu Gly Thr Ala Trp Leu Pro Gly
35 40 45

Asn Pro Gly Gly Arg Gly His Gly Gly Gly Arg His Gly Pro Ala Gly
50 55 60

Thr Ser Val Glu Leu Gly Leu Gln Gln Gly Ile Gly Leu His Lys Ala
65 70 75 80

Leu Ser Thr Gly Leu Asp Tyr Ser Pro Pro Ser Ala Pro Arg Ser Val
85 90 95

Pro Val Ala Thr Thr Leu Pro Ala Ala Tyr Ala Thr Pro Gln Pro Gly
100 105 110

Thr Pro Val Ser Pro Val Gln Tyr Ala His Leu Pro His Thr Phe Gln
115 120 125

Phe Ile Gly Ser Ser Gln Tyr Ser Gly Thr Tyr Ala Ser Phe Ile Pro
130 135 140

Ser Gln Leu Ile Pro Pro Thr Ala Asn Pro Val Thr Ser Ala Val Ala
145 150 155 160

Ser Ala Ala Gly Ala Thr Thr Pro Ser Gln Arg Ser Gln Leu Glu Ala
165 170 175

Tyr Ser Thr Leu Leu Ala Asn Met Gly Ser Leu Ser Gln Thr Pro Gly
180 185 190

His Lys Ala Glu Gln Gln Gln Gln Gln Gln Gln Gln Gln Gln Gln Gln
195 200 205

His Gln His Gln Gln Gln Gln Gln Gln Gln Gln Gln Gln Gln Gln Gln
210 215 220

Gln Gln His Leu Ser Arg Ala Pro Gly Leu Ile Thr Pro Gly Ser Pro
225 230 235 240

Pro Pro Ala Gln Gln Asn Gln Tyr Val His Ile Ser Ser Ser Pro Gln
245 250 255

Asn Thr Gly Arg Thr Ala Ser Pro Pro Ala Ile Pro Val His Leu His
260 265 270

Pro His Gln Thr Met Ile Pro His Thr Leu Thr Leu Gly Pro Pro Ser
275 280 285

Gln Val Val Met Gln Tyr Ala Asp Ser Gly Ser His Phe Val Pro Arg
290 295 300

Glu Ala Thr Lys Lys Ala Glu Ser Ser Arg Leu Gln Gln Ala Ile Gln
305 310 315 320

Ala Lys Glu Val Leu Asn Gly Glu Met Glu Lys Ser Arg Arg Tyr Gly
325 330 335

Ala Pro Ser Ser Ala Asp Leu Gly Leu Gly Lys Ala Gly Gly Lys Ser
340 345 350

Val Pro His Pro Tyr Glu Ser Arg His Val Val Val His Pro Ser Pro
355 360 365

-continued

Ser Asp Tyr Ser Ser Arg Asp Pro Ser Gly Val Arg Ala Ser Val Met
370 375 380

Val Leu Pro Asn Ser Asn Thr Pro Ala Ala Asp Leu Glu Val Gln Gln
385 390 395 400

Ala Thr His Arg Glu Ala Ser Pro Ser Thr Leu Asn Asp Lys Ser Gly
405 410 415

Leu His Leu Gly Lys Pro Gly His Arg Ser Tyr Ala Leu Ser Pro His
420 425 430

Thr Val Ile Gln Thr Thr His Ser Ala Ser Glu Pro Leu Pro Val Gly
435 440 445

Leu Pro Ala Thr Ala Phe Tyr Ala Gly Thr Gln Pro Pro Val Ile Gly
450 455 460

Tyr Leu Ser Gly Gln Gln Gln Ala Ile Thr Tyr Ala Gly Ser Leu Pro
465 470 475 480

Gln His Leu Val Ile Pro Gly Thr Gln Pro Leu Leu Ile Pro Val Gly
485 490 495

Ser Thr Asp Met Glu Ala Ser Gly Ala Ala Pro Ala Ile Val Thr Ser
500 505 510

Ser Pro Gln Phe Ala Ala Val Pro His Thr Phe Val Thr Thr Ala Leu
515 520 525

Pro Lys Ser Glu Asn Phe Asn Pro Glu Ala Leu Val Thr Gln Ala Ala
530 535 540

Tyr Pro Ala Met Val Gln Ala Gln Ile His Leu Pro Val Val Gln Ser
545 550 555 560

Val Ala Ser Pro Ala Ala Ala Pro Pro Thr Leu Pro Pro Tyr Phe Met
565 570 575

Lys Gly Ser Ile Ile Gln Leu Ala Asn Gly Glu Leu Lys Lys Val Glu
580 585 590

Asp Leu Lys Thr Glu Asp Phe Ile Gln Ser Ala Glu Ile Ser Asn Asp
595 600 605

Leu Lys Ile Asp Ser Ser Thr Val Glu Arg Ile Glu Asp Ser His Ser
610 615 620

Pro Gly Val Ala Val Ile Gln Phe Ala Val Gly Glu His Arg Ala Gln
625 630 635 640

Val Ser Val Glu Val Leu Val Glu Tyr Pro Phe Phe Val Phe Gly Gln
645 650 655

Gly Trp Ser Ser Cys Cys Pro Glu Arg Thr Ser Gln Leu Phe Asp Leu
660 665 670

Pro Cys Ser Lys Leu Ser Val Gly Asp Val Cys Ile Ser Leu Thr Leu
675 680 685

Lys Asn Leu Lys Asn Gly Ser Val Lys Lys Gly Gln Pro Val Asp Pro
690 695 700

Ala Ser Val Leu Leu Lys His Ser Lys Ala Asp Gly Leu Ala Gly Ser
705 710 715 720

Arg His Arg Tyr Ala Glu Gln Glu Asn Gly Ile Asn Gln Gly Ser Ala
725 730 735

Gln Met Leu Ser Glu Asn Gly Glu Leu Lys Phe Pro Glu Lys Met Gly
740 745 750

Leu Pro Ala Ala Pro Phe Leu Thr Lys Ile Glu Pro Ser Lys Pro Ala
755 760 765

Ala Thr Arg Lys Arg Arg Trp Ser Ala Pro Glu Ser Arg Lys Leu Glu
770 775 780

Lys Ser Glu Asp Glu Pro Pro Leu Thr Leu Pro Lys Pro Ser Leu Ile
785 790 795 800

-continued

Pro Gln Glu Val Lys Ile Cys Ile Glu Gly Arg Ser Asn Val Gly Lys
805 810 815

(2) INFORMATION FOR SEQ ID NO:10:

(i) SEQUENCE CHARACTERISTICS:
(A) LENGTH: 14 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:10:

TTTACAGTAA GTGA 14

(2) INFORMATION FOR SEQ ID NO:11:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:11:

GTTTCTATGC ATAGGTTTTA CC 22

(2) INFORMATION FOR SEQ ID NO:12:

(i) SEQUENCE CHARACTERISTICS:
(A) LENGTH: 14 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:12:

GGAAAGGTAT ATGG 14

(2) INFORMATION FOR SEQ ID NO:13:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:13:

CTCGACCATT GCAGGAGCAT CG 22

(2) INFORMATION FOR SEQ ID NO:14:

(i) SEQUENCE CHARACTERISTICS:
(A) LENGTH: 14 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:14:

TGTCAGGTGA GAGT 14

( 2 ) INFORMATION FOR SEQ ID NO:15:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:15:

TTGTTTGACT GCAGCATACT GG 22

( 2 ) INFORMATION FOR SEQ ID NO:16:

( i ) SEQUENCE CHARACTERISTICS:
( A ) LENGTH: 14 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:16:

TTTTTGGTAA GTCA 14

( 2 ) INFORMATION FOR SEQ ID NO:17:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:17:

TTTTATAATT ACAGGTCTAG GC 22

( 2 ) INFORMATION FOR SEQ ID NO:18:

( i ) SEQUENCE CHARACTERISTICS:
( A ) LENGTH: 14 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:18:

GTACAGGTAA ACAT 14

( 2 ) INFORMATION FOR SEQ ID NO:19:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:19:

TTTTTCTATT CCAGTTTTCC AA 22

( 2 ) INFORMATION FOR SEQ ID NO:20:

( i ) SEQUENCE CHARACTERISTICS:
( A ) LENGTH: 14 base pairs
( B ) TYPE: nucleic acid -continued ( C ) STRANDEDNESS: single
( D ) TOPOLOGY: linear ( i i ) MOLECULE TYPE: DNA ( x i ) SEQUENCE DESCRIPTION: SEQ ID NO:20:

C A T A G G G T G A G T G A 1 4

( 2 ) INFORMATION FOR SEQ ID NO:21:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:21:

T A T T T C C A T G C T A G G T A T T T C T 2 2

( 2 ) INFORMATION FOR SEQ ID NO:22:

( i ) SEQUENCE CHARACTERISTICS:
( A ) LENGTH: 14 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:22:

A A T G T T G T A A G T T A 1 4

( 2 ) INFORMATION FOR SEQ ID NO:23:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:23:

C T T C C C T T T C C C A G C A T C C A G A 2 2

( 2 ) INFORMATION FOR SEQ ID NO:24:

( i ) SEQUENCE CHARACTERISTICS:
( A ) LENGTH: 14 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:24:

G C C C A G G T A A C G T T 1 4

( 2 ) INFORMATION FOR SEQ ID NO:25:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA -continued ( x i ) SEQUENCE DESCRIPTION: SEQ ID NO:25:

C C C T G T T T C C A C A G G T C A G C G T 2 2

( 2 ) INFORMATION FOR SEQ ID NO:26:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:26:

C C G G A G C C C T G C T G A G G T 1 8

( 2 ) INFORMATION FOR SEQ ID NO:27:

( i ) SEQUENCE CHARACTERISTICS:
( A ) LENGTH: 16 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:27:

C C A G A C G C C G G G A C A C 1 6

( 2 ) INFORMATION FOR SEQ ID NO:28:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:28:

A A C T G G A A A T G T G G A C G T A C 2 0

( 2 ) INFORMATION FOR SEQ ID NO:29:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:29:

C A A C A T G G G C A G T C T G A G 1 8

( 2 ) INFORMATION FOR SEQ ID NO:30:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:30:

C C A C C A C T C C A T C C C A G C 1 8

( 2 ) INFORMATION FOR SEQ ID NO:31:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:31:

T G C T G G G C T G G T G G G G G G 1 8

( 2 ) INFORMATION FOR SEQ ID NO:32:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:32:

C T C T C G G C T T T C T T G G T G 1 8

( 2 ) INFORMATION FOR SEQ ID NO:33:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:33:

G T A C G T C C A C A T T T C C A G T T 2 0

( 2 ) INFORMATION FOR SEQ ID NO:34:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:34:

A G G A G T G A G C C A C C G C A C C C A G C C 2 4

( 2 ) INFORMATION FOR SEQ ID NO:35:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:35:

C C C G G A T C C T G T G T G T G T G T G T G T G T G 2 7

( 2 ) INFORMATION FOR SEQ ID NO:36:

( i ) SEQUENCE CHARACTERISTICS:
( A ) LENGTH: 27 base pairs
( B ) TYPE: nucleic acid ( C ) STRANDEDNESS: single
( D ) TOPOLOGY: linear ( i i ) MOLECULE TYPE: DNA ( x i ) SEQUENCE DESCRIPTION: SEQ ID NO:36:

CCCGGATCCA CACACACACA CACACAC 27

( 2 ) INFORMATION FOR SEQ ID NO:37:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:37:

AAGTCAGCCT CTACTCTTTG TTGA 24

( 2 ) INFORMATION FOR SEQ ID NO:38:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:38:

CTTGGAGCAG TCTGTAGGGA G 21

( 2 ) INFORMATION FOR SEQ ID NO:39:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:39:

TGAAGTGATG TGCTCTGTTC 20

( 2 ) INFORMATION FOR SEQ ID NO:40:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:40:

AAAGGGGTAG AGGAAATGAG 20

( 2 ) INFORMATION FOR SEQ ID NO:41:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:41:

AGGAGAGGGG TCATGAGTTG 20

( 2 ) INFORMATION FOR SEQ ID NO:42:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:42:

GGCTCATGAA TACATTACAT GAAG 24

( 2 ) INFORMATION FOR SEQ ID NO:43:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:43:

CTCATTCACC TTAGAGACAA ATGGATAG 28

( 2 ) INFORMATION FOR SEQ ID NO:44:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:44:

ATGGTATAGG GATTTTCCAA ACCTG 25

( 2 ) INFORMATION FOR SEQ ID NO:45:

( i ) SEQUENCE CHARACTERISTICS:
( A ) LENGTH: 54 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:45:

CACACACACA CACACACACA CACACACACA CATACACACA CACACACACA CACA 54

( 2 ) INFORMATION FOR SEQ ID NO:46:

( i ) SEQUENCE CHARACTERISTICS:
( A ) LENGTH: 32 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:46:

GAGAATGACA GAGAGAGAGA GAGAGAGAGA GA 32

-continued ( 2 ) INFORMATION FOR SEQ ID NO:47:

( i ) SEQUENCE CHARACTERISTICS:
( A ) LENGTH: 66 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:47:

GAGAAAGAGA GAGAGAGAGT GAGTGTGTGT GTGTGTGTGT GTGTGTGTGT GTGTATGTGT 60

GTGTGT 66

( 2 ) INFORMATION FOR SEQ ID NO:48:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:48:

CTTGTTCATC TGCCTTGTGC 20

( 2 ) INFORMATION FOR SEQ ID NO:49:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:49:

ACCTAAGCGA CTGCCTAAAC 20

( 2 ) INFORMATION FOR SEQ ID NO:50:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:50:

TTAAGGAAGT GTTCACATCA GGG 23

( 2 ) INFORMATION FOR SEQ ID NO:51:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:51:

AATTGTGCTT ATGTCACTGG G 21

( 2 ) INFORMATION FOR SEQ ID NO:52:

( i ) SEQUENCE CHARACTERISTICS:

( A ) LENGTH: 17 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:52:

A A T T C T G G A G A G G A T G T 1 7

( 2 ) INFORMATION FOR SEQ ID NO:53:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:53:

T G G T T C T T T T T T T G G T A G 1 8

( 2 ) INFORMATION FOR SEQ ID NO:54:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:54:

C A T C G T G T T G T G T G G T G A A G 2 0

( 2 ) INFORMATION FOR SEQ ID NO:55:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:55:

C T C A G A C G C T A A A C T C A A G G 2 0

( 2 ) INFORMATION FOR SEQ ID NO:56:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:56:

A T G A T C C G T G G T A G T G G C 1 8

( 2 ) INFORMATION FOR SEQ ID NO:57:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:57:

A G G A C C T G T T A C T G A C G C C 1 9

( 2 ) INFORMATION FOR SEQ ID NO:58:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:58:

C T C A T C T G T T G A A T G G G G A T 2 0

( 2 ) INFORMATION FOR SEQ ID NO:59:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:59:

C T T A A A T G C T A T G C C T T C C G 2 0

( 2 ) INFORMATION FOR SEQ ID NO:60:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:60:

T G C A A A T C C C T C A G T T C A C T 2 0

( 2 ) INFORMATION FOR SEQ ID NO:61:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:61:

T G C T T G A C T T T G C C A T G T T C 2 0

( 2 ) INFORMATION FOR SEQ ID NO:62:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:62:

A T A C C C A T A C G G A T T T G A G G 2 0

( 2 ) INFORMATION FOR SEQ ID NO:63:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:63:

GCAACACTAT CAGGCTAAGA ATG 23

( 2 ) INFORMATION FOR SEQ ID NO:64:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:64:

CAAATACCAG CAACTCACCA GC 22

( 2 ) INFORMATION FOR SEQ ID NO:65:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:65:

GGTTCCTTCA GCATCCTACA TTC 23

( 2 ) INFORMATION FOR SEQ ID NO:66:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:66:

GCTGCTGCTG CTGCTGCTGC T 21

( 2 ) INFORMATION FOR SEQ ID NO:67:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:67:

GTAGTAGTTT TTGTGAGG 18

( 2 ) INFORMATION FOR SEQ ID NO:68:

( i ) SEQUENCE CHARACTERISTICS:

-continued ( A ) LENGTH: 19 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:68:

CACCAAGCTC CCTGATGGA 19

( 2 ) INFORMATION FOR SEQ ID NO:69:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:69:

GCTTGAATGG ACCACCCT 18

( 2 ) INFORMATION FOR SEQ ID NO:70:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:70:

ATCTCCTCCT CCACTGCCAC 20

( 2 ) INFORMATION FOR SEQ ID NO:71:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:71:

AGACTCTTTC ACTATGCTC 19

( 2 ) INFORMATION FOR SEQ ID NO:72:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:72:

TTCAGCCTGC ACGGATGGT 19

( 2 ) INFORMATION FOR SEQ ID NO:73:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:73:

TGGCAGTGGA GAATCTCAGT 20

( 2 ) INFORMATION FOR SEQ ID NO:74:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:74:

TGCTGCAAGG AACTGATAGC 20

( 2 ) INFORMATION FOR SEQ ID NO:75:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:75:

AATGGTCTAA TTTCTTTGG 19

( 2 ) INFORMATION FOR SEQ ID NO:76:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:76:

GAGAAAGAAA TCGACGTGC 19

( 2 ) INFORMATION FOR SEQ ID NO:77:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:77:

ACAGGCTCTG GAGGGCTCCT 20

( 2 ) INFORMATION FOR SEQ ID NO:78:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:78:

TCCATGGTGA AGTATAGGCT 20

( 2 ) INFORMATION FOR SEQ ID NO:79:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:79:

A G C A G G A T G A   C C A G C C C T G T   2 0

( 2 ) INFORMATION FOR SEQ ID NO:80:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:80:

G C T C T T T G A T   T T G C C G T G T   1 9

( 2 ) INFORMATION FOR SEQ ID NO:81:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:81:

T G T G A A T T C A   T G A A A T C C A A   C C A A G A G C G   2 9

( 2 ) INFORMATION FOR SEQ ID NO:82:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:82:

T G T G A A T T C A   T G A T C C C A C A   C A C G C T C A C   2 9

( 2 ) INFORMATION FOR SEQ ID NO:83:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:83:

T G T G A A T T C A   T G G T G C A G G C   C C A G A T C   2 7

( 2 ) INFORMATION FOR SEQ ID NO:84:

( i ) SEQUENCE CHARACTERISTICS:

-continued ( A ) LENGTH: 29 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:84:

TTCGAAGCTT CTACTTGCCT ACATTAGAC 29

( 2 ) INFORMATION FOR SEQ ID NO:85:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:85:

TTGACCTTTA CACCTGCAT 19